US012697380B2

(12) United States Patent
Zhang et al.

(10) Patent No.: US 12,697,380 B2
(45) Date of Patent: Aug. 4, 2026

(54) ATTENUATED VIRUS OF FLAVIVIRUS VIRUS AND USE THEREOF

(71) Applicant: Zhejiang Free Trade Zone Hongan Base Biotechnology Co., Ltd., Zhoushan (CN)

(72) Inventors: Bo Zhang, Wuhan (CN); Hanqing Ye, Wuhan (CN); Yanan Zhang, Wuhan (CN); Na Li, Wuhan (CN); Qiuyan Zhang, Wuhan (CN); Chenglin Deng, Wuhan (CN); Shaopeng Yuan, Wuhan (CN); Shunli Zhan, Wuhan (CN); Lei Gao, Wuhan (CN)

(73) Assignee: ZHEJIANG FREE TRADE ZONE HONGAN BASE BIOTECHNOLOGY CO., LTD., Zhoushan (CN)

( * ) Notice: Subject to any disclaimer, the term of this patent is extended or adjusted under 35 U.S.C. 154(b) by 520 days.

(21) Appl. No.: 18/268,661

(22) PCT Filed: Dec. 21, 2021

(86) PCT No.: PCT/CN2021/140236
§ 371 (c)(1),
(2) Date: Jun. 21, 2023

(87) PCT Pub. No.: WO2022/135425
PCT Pub. Date: Jun. 30, 2022

(65) Prior Publication Data
US 2024/0042004 A1 Feb. 8, 2024

(30) Foreign Application Priority Data
Dec. 22, 2020 (CN) .......................... 202011528256.1

(51) Int. Cl.
*A61K 39/12* (2006.01)
*A61P 31/14* (2006.01)
*C12N 7/04* (2006.01)
*A61K 39/00* (2006.01)

(52) U.S. Cl.
CPC .............. *A61K 39/12* (2013.01); *A61P 31/14* (2018.01); *C12N 7/04* (2013.01); *A61K 2039/5254* (2013.01)

(58) Field of Classification Search
None
See application file for complete search history.

(56) References Cited

U.S. PATENT DOCUMENTS

2020/0197505 A1 6/2020 Shi et al.

FOREIGN PATENT DOCUMENTS

| CN | 103088049 A | 5/2013 | |
|---|---|---|---|
| CN | 106574253 A | 4/2017 | |
| CN | 107201370 A | 9/2017 | |
| CN | 111334482 A | 6/2020 | |
| CN | 113186171 A | 7/2021 | |
| WO | 2005049815 A1 | 6/2005 | |
| WO | WO-2018152158 A1 * | 8/2018 | ............. A61K 39/12 |
| WO | 2020051080 A1 | 3/2020 | |

OTHER PUBLICATIONS

Zhang Qiuyan, et al., Construction of replication-defective flavivirus and study on the production mechanism of subgenomic flavivirus RNA, 2019, pp. 1-118.
Joseph E. Blaney Jr., et al., Dengue virus type 3 vaccine candidates generated by introduction of deletions in the 3' untranslated region (3'-UTR) or by exchange of the DENV-3 3'-UTR with that of DENV-4, Vaccine, 2008, pp. 817-828, vol. 26 No. 6.
Justin A. Roby, et al., Noncoding Subgenomic Flavivirus RNA: Multiple Functions in West Nile Virus Pathogenesis and Modulation of Host Responses, Viruses, 2014, pp. 404-427, vol. 6 No. 2.
Qiu-Yan Zhang, et al., Short Direct Repeats in the 3' Untranslated Region Are Involved in Subgenomic Flaviviral RNA Production, Journal of Virology, 2020, pp. 1-14, vol. 94 Issue 6, e01175-19.
Natalie D. Collins, et al., Using Next Generation Sequencing to Study the Genetic Diversity of Candidate Live Attenuated Zika Vaccines, Vaccines, 2020, pp. 1-9, vol. 8 No. 2, 161.
Sergio M. Villordo, et al., Genome cyclization as strategy for flavivirus RNA replication, Virus Research, 2009, pp. 230-239, vol. 139 No.2.

* cited by examiner

*Primary Examiner* — Shanon A. Foley
*Assistant Examiner* — Myron G Hill
(74) *Attorney, Agent, or Firm* — Bayramoglu Law Offices LLC

(57) ABSTRACT

Provided are an attenuated virus of a flavivirus virus and the use thereof. The attenuated virus comprises a polyadenylic acid (poly(A)) sequence, wherein the polyadenylic acid (poly(A)) is used for replacing a part of the nucleotide sequence of a 3' untranslated region (3'UTR) of the flavivirus virus, so that the 3' untranslated region (3'UTR) of the attenuated virus obtained after the part of the nucleotide sequence of the flavivirus virus is replaced at least retains a 3'-end stem loop region (3'SL). The attenuated virus can be used for preparing safe and effective attenuated vaccine strains.

20 Claims, 6 Drawing Sheets

Specification includes a Sequence Listing.

ATTENUATED VIRUS OF FLAVIVIRUS VIRUS AND USE THEREOF

CROSS REFERENCE TO THE RELATED APPLICATIONS

This application is the national phase entry of International Application No. PCT/CN2021/140236, filed on Dec. 21, 2021, which is based upon and claims priority to Chinese Patent Application No. 202011528256.1, filed on Dec. 22, 2020, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBZD019_Sequence_Listing.txt, created on 06/21/2023, and is 84,404 bytes in size.

TECHNICAL FIELD

The present disclosure belongs to the field of biotechnology, and in particular relates to an attenuated virus of a flavivirus virus and use thereof.

BACKGROUND

The flaviviruses belong to a flaviviridae family and contain more than 70 viruses, most of which are spread by mosquitoes or ticks. Among these viruses, Japanese encephalitis virus (JEV), tick-borne encephalitis virus (TBEV), yellow fever virus (YFV), West Nile virus (WNV), St. Louis encephalitis virus (SLEV), Murray Valley encephalitis virus (MVEV), dengue virus (DENV) and zika virus (ZIKV) are important human pathogens causing high morbidity and mortality worldwide. Severe flavivirus infection diseases include hemorrhagic fevers (YFV and DENV), encephalitis, and neurological sequelae (JEV, TBEV, WNV, SLEV, and MVEV), which can lead to death, with mortality from JEV, YFV, TBEV, and DENV ranging from 5% to 30%.

As shown by the World Health Organization, DENV is currently epidemic in more than 100 countries, causing 20,000 deaths each year; JEV is epidemic in Southeast Asia and the Western Pacific, with 68,000 cases reported annually; WNV broke out in New York in 1999, causing 9,862 infected cases and 264 deaths (CDC statistics), and rapidly spread from North America to Central America and finally to South America, where the epidemic area is still expanding; and following a small epidemic in Yap, Micronesia and Gabon in 2007, an unexpected large-scale outbreak of ZIKV happened in Latin America in 2016, and such ZIKV infection was associated with severe neurological disorders (Guillain-Barre syndrome) and neonatal head malformations, and thus was declared a "Public Health Emergency of Global Concern". In 2016, about 4 million cases of ZIKV infections were recorded in the United States alone. Since then, ZIKV has spread rapidly to French Polynesia, South America, Africa, Asia and other regions. As a result, flavivirus infections have become one of the major public health problems facing the world.

At present, there are no effective antiviral drugs and specific treatments against flavivirus infections, and there are only three flavivirus vaccines for human prophylaxis. Therefore, the development of novel and more effective flavivirus vaccines is of great strategic significance for the prevention of flavivirus infections in China and even the world. Among many types of vaccines, live attenuated vaccines have been focused on vaccine research and development because of their strong immunogenicity, as well as the characteristics that a single immunization can induce humoral and cellular immune responses, and induce more comprehensive and durable immune protection.

A flavivirus genome is a single-stranded positive-sense RNA with a total length of about 11,000 bases, consisting of a 5' untranslated region (5'UTR), a 3' untranslated region (3'UTR), and a long open reading frame in the middle. Although the 5' end of the genome has a 7-methylguanosine cap (m$^7$GpppAmp Cap) structure similar to mRNA, the 3' end of the genome does not have a polyadenosine tail poly(A) and instead contains a conserved 5'-CU$_{OH}$-3' sequence. The untranslated region (UTR) of the flavivirus genome contains conserved RNA sequences that form highly complex secondary and tertiary structures, which play a multifaceted role in virus replication, translation, propagation, and pathogenicity (Viruses. 2014 Jan. 27; 6(2): 404-27).

The 5'UTR has a length of about 100 bases and contains: i) a conserved stem loops (SL) structure, in which SL-A is a promoter element for RNA synthesis, which binds to NS5-RdRp (Genes Dev. 2006 Aug. 15; 20(16): 2238-49) and initiates the synthesis of negative-stranded RNA; and ii) cyclization sequences upstream of an initiation codon AUG (5'upstream of AUG region (5'UAR), 5' cyclization sequences (5'CS) and 5' downstream of AUG region (5'DAR)), which mediate long-range RNA-RNA interactions (Virus Res. 2009 February; 139(2): 230-9). The 3'UTR is long, about 400-700 bases, forming a plurality of conserved RNA secondary structures, which play an important role in the replication, pathogenicity and propagation of viruses. 3'UTR may be structurally divided into i) a stem loop region (SL); ii) a dumbbell region (DB); and iii) a short hairpin 3' stem loop region (sHP-3'SL). sHP-3'SL is a most conserved RNA secondary structure in flaviviruses, and its complementary cyclization sequences 3'CS, 3'UAR and 3'DAR are complementarily paired with corresponding 5'CS, 5'UAR and 5'DAR, resulting in genomic cyclization that is a necessary cis-action for RNA replication initiation. The stem loop region (SL) and the dumbbell region (DB), as enhancers in the genome replication process, are not very conserved in flaviviruses, and their sizes and structures vary as different viruses. Although the stem loop region (SL) and the dumbbell region (DB) play unnecessary roles in genome replication, a number of studies based on the weakening or enhancement of virulence due to different degrees of deletion or point mutation in SL and DB regions have shown that the stem loop region (SL) and the dumbbell region (DB) play important roles in regulating virus virulence, host immune response, host adaptation and the like. Therefore, the stem loop region (SL) and the dumbbell region (DB) have become two important targets for designing attenuated vaccines.

Taking overall consideration of these factors, alternative attenuated vaccine candidates of flaviviruses with improved efficacy and safety profiles are required.

SUMMARY OF THE INVENTION

According to the present disclosure, an attenuated poly (A) virus strain of a flavivirus virus is constructed by replacing all or a part of a nucleotide sequence of a 5'-end stem loop region (SL), all or a part of a nucleotide sequence of a cyclization sequence region (CS), and/or all or a part of a nucleotide sequence of a dumbbell region (DB) in a 3' untranslated region (3'UTR) with a poly(A) sequence; and the attenuated poly(A) virus strain has been well documented as an attenuated vaccine candidate strain of a wild-type virus through extensive in vivo studies. This virus provides the basis for a vaccine that is used safely.

One object of the present disclosure is to provide an attenuated flavivirus virus having attenuated properties while still having good immunogenicity. The attenuated flavivirus virus comprises a polyadenylic acid (poly(A)) sequence, wherein the poly(A) sequence is used for replacing a part of nucleotide sequence of a 3' untranslated region (3'UTR) of the flavivirus virus, so that the 3' untranslated region (3'UTR) of the attenuated flavivirus virus obtained in response to the part of the nucleotide sequence of the flavivirus virus being replaced at least retains a 3'-end stem loop region (3'SL).

Another object of the present disclosure is to provide a DNA, which can be transcribed to produce an RNA genome of the attenuated flavivirus virus as described above.

Another object of the present disclosure is to provide a cell, which comprises the attenuated flavivirus virus or the DNA as described above.

Another object of the present disclosure is to a vaccine, which comprises the attenuated flavivirus virus, the DNA and/or the cell as described above.

Another object of the present disclosure is to provide a pharmaceutical composition, which comprises the attenuated flavivirus virus, the DNA, the cell and/or the vaccine as described above, and a pharmaceutically acceptable vector.

Another object of the present disclosure is to provide a method for preparing the attenuated flavivirus virus as described above, the method comprising substituting all or a part of nucleotide sequence of a 3' untranslated region (3'UTR) of a wild-type virus with a polyadenylic acid (poly(A)) sequence.

Another object of the present disclosure is to provide use of the attenuated flavivirus virus, the DNA and/or the cell as described above in the preparation of an attenuated flavivirus virus vaccine.

Another object of the present disclosure is to provide use of the attenuated flavivirus virus, the DNA, the cell, the vaccine and/or the pharmaceutical composition as described above in the preparation of a medicament for treating or preventing diseases caused by a flavivirus virus.

Another object of the present disclosure is to provide a method for stimulating an immune response to a flavivirus virus, the method comprising immunological administration of the attenuated flavivirus virus, the DNA, the cell, the vaccine and/or the pharmaceutical composition.

DETAILED DESCRIPTION OF THE INVENTION

I. Definition

Figure 1:
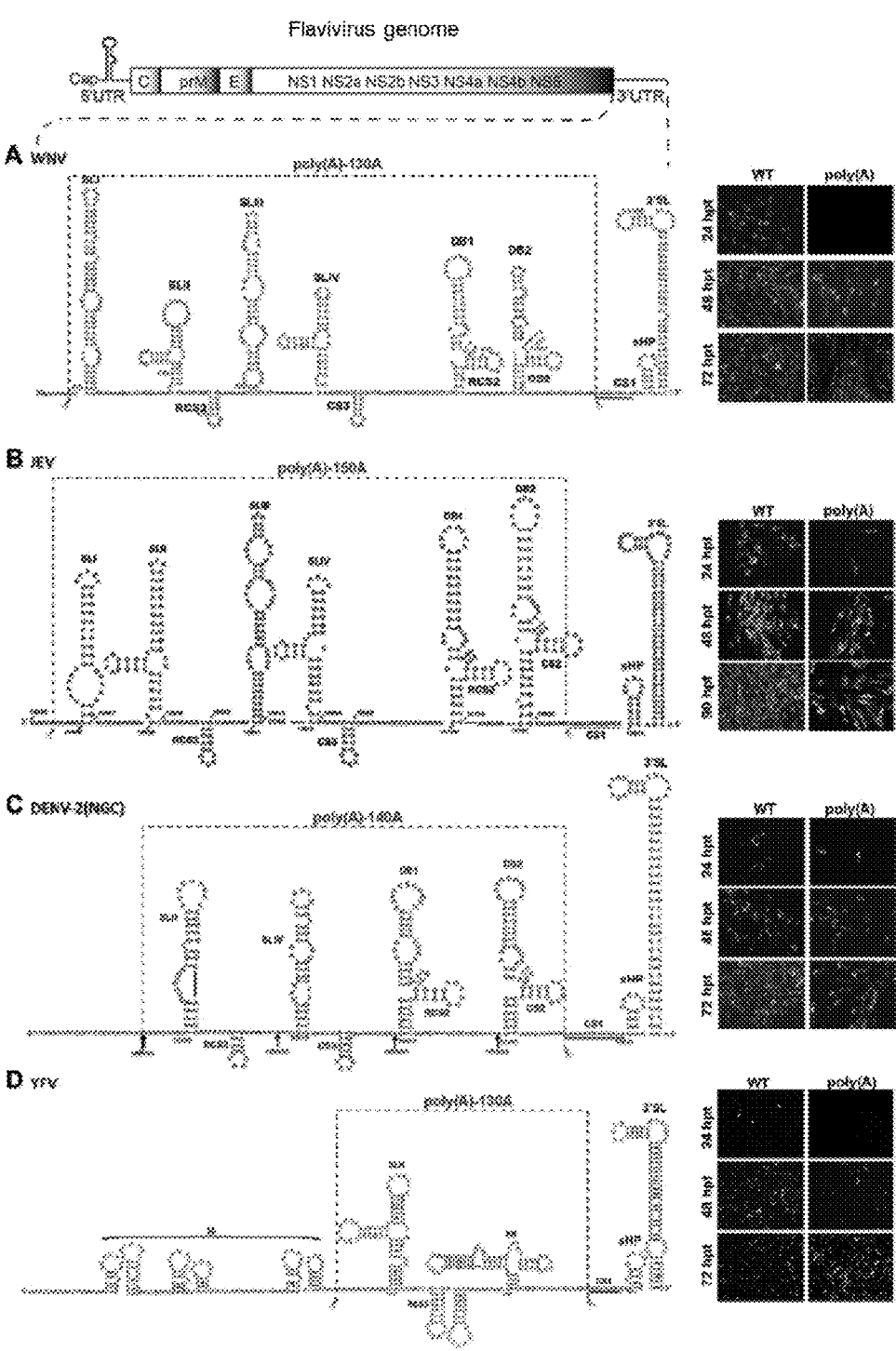
FIG. 1 shows schematic diagrams of clone construction of attenuated flavivirus strains in which 3'UTR is replaced with a poly(A) sequence, and virus rescue, wherein: A: WNV-poly(A) clone construction and virus rescue IFA validation; B: JEV-poly(A) clone construction and virus rescue IFA validation; C: DENV-2(NGC)-poly(A) clone construction and virus rescue IFA validation; and D: YFV-poly(A) clone construction and virus rescue IFA validation.

In the present disclosure, unless otherwise defined, all scientific and technical terms as used herein have the meaning as commonly understood by a person skilled in the art. In addition, terms related to proteins, nucleic acid chemistry, molecular biology, cell and tissue culture, microbiology and immunology, and laboratory operating steps as used herein are terms and conventional steps widely used in the respective fields. Meanwhile, in order to better understand the present disclosure, definitions and explanations of related terms are provided below.

As used herein and unless otherwise stated, the term "about" or "approximately" means a range within plus or minus 10% of a given value or range. In cases where an integer is required, this term means an integer within a range plus or minus 10% of a given value or range, or a nearest integer obtained by rounding this range up or down.

As used herein, the flavivirus viruses may include, but are not limited to: Japanese encephalitis virus (JEV), West Nile virus (WNV), tick-borne encephalitis virus (TBEV), yellow fever virus (YFV), dengue virus (DENV), zika virus (ZIKV), St. Louis encephalitis virus (SLEV), Murray Valley encephalitis virus (MVEV), Omsk hemorrhagic fever virus and Kyasanur Forest Disease Virus or any related flavivirus.

As used herein, a 5'-end stem loop region (SL), a dumbbell region (DB), a repetitive cyclization sequence region 3 (RCS3), a cyclization sequence region 3 (CS3), a repetitive cyclization region 2 (RCS2), a cyclization sequence region 2 (CS2), a cyclization sequence region 1 (CS1), and a short hairpin-3' stem loop region (sHP-3'SL) behind the cyclization sequence region 1 in a 3' untranslated region of a flavivirus are the terms in the respective fields. In other studies, the stem loop region (SL) is also referred to as a variable region (VR).

As used herein, the term "live attenuated virus" or "attenuated virus" refers to a virus that has been altered from a primitive parent virus or a wild-type virus in such a manner that its abilities to infect a host, replicate within the host, package, reinfect the host, or combine are attenuated. In general, such attenuation may happen in several or all hosts of the virus, or only in one or more hosts of the virus. Thus, the attenuation of the live attenuated virus (that is, its abilities to infect a host, replicate within the host, package, reinfect the host, or combine are attenuated) is usually associated with one or more hosts of the virus, wherein the live attenuated virus is not significantly or measurably attenuated in one or more other hosts of the virus. The live attenuated virus disclosed herein is usually genetically altered, or may be referred to as being mutated, a mutant, being genetically engineered, a recombinant, or a combination thereof.

As used herein, the term "live attenuated vaccine" or "attenuated vaccine" refers to a pharmaceutical composition comprising a live attenuated pathogen, such as a virus. The pharmaceutical composition comprises at least one immunoactive component, which induces an immune response against the virus in a subject, protects the subject from death or possible death due to the virus, or both, and optionally may include additional components of the immune activity of one or more enhanced active components. A vaccine may additionally include other components typical of the pharmaceutical composition. At least one immunoactive component is one or more live attenuated viruses described herein.

As used herein, the term "virus rescue" refers to a process of introducing in vitro constructs containing virus sequences into appropriate cells to produce invasive or infectious viruses. "Recombinant virus" refers to a genetically engineered virus produced by a recombinant DNA technology, in which a virus sequence is artificially subjected to any genetic manipulations such as deletion, insertion, inversion, and replacement to distinguish this virus from naturally occurring viruses.

As used herein, the term "recombinant RNA virus" refers to the virus described herein comprising a heterologous RNA.

As used herein, the term "wild-type" in the case of viruses refers to a type of virus that is epidemic and naturally propagated and breaks outs as a typical disease. In other embodiments, in the case of viruses, the term "wild type" refers to a parent virus.

As used herein, the term "multiplicity of injection" or "MOI" is an average number of infectious virus particles per infected cell. MOI is calculated by dividing the number of infectious virus particles added (added ml×PFU/ml) by the number of cells added (added ml×cells/ml).

II. Detailed Description of Embodiments

In one aspect, the present disclosure provides an attenuated flavivirus virus, which comprises a polyadenylic acid (poly(A)) sequence, wherein the polyadenylic acid (poly (A)) sequence is used for replacing a part of nucleotide sequence of a 3' untranslated region (3'UTR) of the flavivirus virus, so that the 3' untranslated region (3'UTR) of the attenuated flavivirus virus obtained in response to the part of the nucleotide sequence of the flavivirus virus being replaced at least retains a 3'-end stem loop region (3'SL).

According to the attenuated flavivirus virus in the previous aspect, the part of nucleotide sequence comprises all or a part of a nucleotide sequence of a 5'-end stem loop region (5' SL), all or a part of a nucleotide sequence of a cyclization sequence region (CS), and/or all or a part of a nucleotide sequence of a dumbbell region (DB) in the 3' untranslated region (3'UTR).

In some embodiments of the present disclosure, after the part of nucleotide sequence is replaced by the polyadenylic acid (poly(A)) sequence, the 3' untranslated region (3'UTR) of the attenuated flavivirus virus retains at least a cyclization sequence region 1 (CS1) and a short hairpin 3' stem loop region (sHP-3'SL) behind the cyclization sequence region 1 in the 3' untranslated region.

In some preferred embodiments of the present disclosure, the 5'-end stem loop region (5'SL) in the 3' untranslated region (3'UTR) is selected from a stem loop region I (SLI), a stem loop region II (SLII), a stem loop region III (SLIII) and a stem loop region IV (SLIV).

In some preferred embodiments of the present disclosure, the cyclization sequence region (CS) is selected from a cyclization sequence region 1 (CS1), a cyclization sequence region 2 (CS2), a cyclization sequence region 3 (CS3), a repetitive cyclization sequence region 2 (RCS2) and a repetitive cyclization sequence region 3 (RCS3).

In some preferred embodiments of the present disclosure, the dumbbell region (DB) is selected from a dumbbell region 1 (DB1) and a dumbbell region 2 (DB2).

According to the attenuated flavivirus virus in any of the previous aspects, the polyadenylic acid (poly(A)) sequence comprises 10-200 adenylates.

In some preferred embodiments of the present disclosure, the polyadenylic acid (poly(A)) sequence comprises 50-180, 100-160 adenylates; more preferably, 130-150 adenylates, preferably 130 or 150 adenylates.

In some preferred embodiments of the present disclosure, the flavivirus virus is selected from the group consisting of Japanese encephalitis virus (JEV), West Nile virus (WNV), tick-borne encephalitis virus (TBEV), yellow fever virus (YFV), dengue virus (DENV), zika virus (ZIKV), St. Louis encephalitis virus (SLEV), Murray Valley encephalitis virus (MVEV), Omsk hemorrhagic fever virus and Kyasanur Forest Disease virus.

In some preferred embodiments of the present disclosure, the attenuated flavivirus virus has a plaque titer of $5\times10^4$–$5\times10^6$ PFU/ml.

In some preferred embodiments of the present disclosure, the attenuated flavivirus virus is 10-100 times less virulent than a parent wild-type virus.

In some preferred embodiments of the present disclosure, the attenuated flavivirus virus is obtained by means of rescue on baby hamster kidney cells BHK-21 and/or amplification on African green monkey kidney Vero cells.

In some preferred embodiments of the present disclosure, the dengue virus is selected from 1-type, 2-type, 3-type and 4-type dengue viruses.

In some preferred embodiments of the present disclosure, the attenuated flavivirus virus is an attenuated West Nile virus. In some preferred embodiments of the present disclosure, the attenuated West Nile virus comprises a nucleotide sequence having 80% or more identity with a nucleotide sequence shown in SEQ ID NO. 1, preferably a nucleotide sequence having more than 85%, 90%, 95%, 96%, 97%, 98%, 99% identity with the nucleotide sequence shown in SEQ ID NO. 1, more preferably a nucleotide sequence having 98% or 99% or more identity with the nucleotide sequence shown in SEQ ID NO. 1. In a specific embodiment of the present disclosure, the nucleotide sequence of the attenuated West Nile virus is shown in SEQ ID NO. 1.

In some preferred embodiments of the present disclosure, the attenuated flavivirus virus is an attenuated Japanese encephalitis virus. In some preferred embodiments of the present disclosure, the attenuated Japanese encephalitis virus comprises a nucleotide sequence having 80% or more identity with a nucleotide sequence shown in SEQ ID NO. 2, preferably a nucleotide sequence having more than 85%, 90%, 95%, 96%, 97%, 98%, 99% identity with the nucleotide sequence shown in SEQ ID NO. 2, more preferably a nucleotide sequence having 98% or 99% or more identity with the nucleotide sequence shown in SEQ ID NO. 2; more preferably, the nucleotide sequence of the attenuated Japanese encephalitis virus is SEQ ID NO. 2. In a specific embodiment of the present disclosure, the nucleotide sequence of the attenuated Japanese encephalitis virus is shown in SEQ ID NO. 2.

In some preferred embodiments of the present disclosure, the attenuated flavivirus virus is an attenuated dengue virus. In some preferred embodiments of the present disclosure, the attenuated dengue virus comprises a nucleotide sequence having 80% or more identity with a nucleotide sequence shown in SEQ ID NO. 3, preferably a nucleotide sequence having more than 85%, 90%, 95%, 96%, 97%, 98%, 99% identity with the nucleotide sequence shown in SEQ ID NO. 3, more preferably a nucleotide sequence having 98% or 99% or more identity with the nucleotide sequence shown in SEQ ID NO. 3; more preferably, the nucleotide sequence of the attenuated dengue virus is SEQ ID NO. 3. In a specific embodiment of the present disclosure, the nucleotide sequence of the attenuated dengue virus is shown in SEQ ID NO. 3.

In some preferred embodiments of the present disclosure, the attenuated flavivirus virus is an attenuated yellow fever virus. In some preferred embodiment of the present disclosure, the attenuated yellow fever virus comprises a nucleotide sequence having 80% or more identity with a nucleotide sequence shown in SEQ ID NO. 4, preferably a nucleotide sequence having more than 85%, 90%, 95%, 96%, 97%, 98%, 99% identity with the nucleotide sequence shown in SEQ ID NO. 4, more preferably a nucleotide sequence having 98% or 99% or more identity with the nucleotide sequence shown in SEQ ID NO. 4; more preferably, the nucleotide sequence of the attenuated yellow fever virus is SEQ ID NO. 4. In a specific embodiment of the present disclosure, the nucleotide sequence of the attenuated yellow fever virus is shown in SEQ ID NO. 4.

In some preferred embodiments of the present disclosure, the attenuated flavivirus virus is an attenuated zika virus. In some preferred embodiments of the present disclosure, the attenuated zika virus comprises a nucleotide sequence having 80% or more identity with a nucleotide sequence shown in SEQ ID NO. 5, preferably a nucleotide sequence having more than 85%, 90%, 95%, 96%, 97%, 98%, 99% identity with the nucleotide sequence shown in SEQ ID NO. 5, more preferably a nucleotide sequence having 98% or 99% or more identity with the nucleotide sequence shown in SEQ ID NO. 5; more preferably, the nucleotide sequence of the attenuated zika virus is SEQ ID NO. 5. In a specific embodiment of the present disclosure, the nucleotide sequence of the attenuated zika virus is shown in SEQ ID NO. 5.

In some preferred embodiments of the present disclosure, the attenuated flavivirus virus is an attenuated tick-borne encephalitis virus. In some preferred embodiments of the present disclosure, the attenuated tick-borne encephalitis virus comprises a nucleotide sequence having 80% or more identity with a nucleotide sequence shown in ID NO. 6, preferably a nucleotide sequence having more than 85%, 90%, 95%, 96%, 97%, 98%, 99% identity with the nucleotide sequence shown in SEQ ID NO. 6, more preferably a nucleotide sequence having 98% or 99% or more identity with the nucleotide sequence shown in SEQ ID NO. 6; more preferably, the nucleotide sequence of the attenuated tick-borne encephalitis virus is SEQ ID NO. 6. In a specific embodiment of the present disclosure, the nucleotide sequence of the attenuated tick-borne encephalitis virus is shown in SEQ ID NO. 6.

In one preferred embodiment of the present disclosure, the part of nucleotide sequence comprises a 5'-end stem loop region I (SLI), a stem loop region II (SLII), a repetitive cyclization sequence region 3 (RCS3), a stem loop region III (SLIII), a stem loop region IV (SLIV), and a cyclization sequence region 3 (CS3), and after the part of nucleotide sequence is replaced by the polyadenylic acid (poly(A)) sequence, the 3' untranslated region (3'UTR) of the attenuated flavivirus virus retains a dumbbell region 1 (DB1), a repetitive cyclization sequence region 2 (RCS2), a dumbbell region 2 (DB2), a cyclization sequence region 2 (CS2), a cyclization sequence region 1 (CS1) and a short hairpin-3' stem loop region (sHP-3'SL) behind the cyclization sequence region 1 in the 3' untranslated region.

In one preferred embodiment of the present disclosure, the part of nucleotide sequence comprises a dumbbell region 1 (DB1), a repetitive cyclization sequence region 2 (RCS2), a dumbbell region 2 (DB2), a cyclization sequence region 2 (CS2), and a cyclization sequence region 1 (CS1), and after the part of nucleotide sequence is replaced by the polyadenylic acid (poly(A)) sequence, the 3' untranslated region (3'UTR) of the attenuated flavivirus virus retains a 5'-end stem loop region I (SLI), a stem loop region II (SLII), a repetitive cyclization sequence region 3 (RCS3), a stem loop region III (SLIII), a stem loop region IV (SLIV), a cyclization sequence region 3 (CS3), and a short hairpin-3' stem loop region (sHP-3'SL) in the 3' untranslated region.

In one preferred embodiment of the present disclosure, the part of nucleotide sequence comprises a 5'-end stem loop region I (SLI), a stem loop region II (SLII), a repetitive cyclization sequence region 3 (RCS3), a stem loop region III (SLIII), a stem loop region IV (SLIV), a cyclization sequence region 3 (CS3), a dumbbell region 1 (DB1), a repetitive cyclization sequence region 2 (RCS2), a dumbbell region 2 (DB2), and a cyclization sequence region 2 (CS2), and after the part of nucleotide sequence is replaced by the polyadenylic acid (poly(A)) sequence, the 3' untranslated region (3'UTR) of the attenuated flavivirus virus retains a cyclization sequence region 1 (CS1) and a short hairpin-3' stem loop region (sHP-3'SL) behind the cyclization sequence region 1 in the 3' untranslated region.

In one preferred embodiment of the present disclosure, the part of nucleotide sequence comprises a 5'-end stem loop region II (SLII), a repetitive cyclization sequence region 3 (RCS3), a stem loop region IV (SLIV), a cyclization sequence region 3 (CS3), a dumbbell region 1 (DB1), a repetitive cyclization sequence region 2 (RCS2), a dumbbell region 2 (DB2), and a cyclization sequence region 2 (CS2), and after the part of nucleotide sequence is replaced by the poly(A) sequence, the 3' untranslated region (3'UTR) of the attenuated flavivirus virus retains a cyclization sequence region 1 (CS1) and a short hairpin 3' stem loop region (sHP-3'SL) behind the cyclization sequence region 1 in the 3' untranslated region.

In one preferred embodiment of the present disclosure, the part of nucleotide sequence comprises a 5'-end stem loop region I (SLII), a repetitive cyclization sequence region 3 (RCS3), a dumbbell region (DB), a repetitive cyclization sequence region 2 (RCS2), a dumbbell region 2 (DB2), and a cyclization sequence region 2 (CS2), and after the part of nucleotide sequence is replaced by the polyadenylic acid (poly(A)) sequence, the 3' untranslated region (3'UTR) of the attenuated flavivirus virus retains 5'-end stem loop region (SL), a cyclization sequence region 1 (CS1) and a short hairpin-3' stem loop region (sHP-3'SL) behind the cyclization sequence region 1 in the 3' untranslated region.

In an aspect, the present disclosure provides a DNA, which can be transcribed to produce an RNA genome of the attenuated flavivirus virus.

In some embodiments of the present disclosure, the DNA is an infectious clone of an attenuated strain of the flavivirus virus.

In some preferred embodiments of the present disclosure, the infectious clone is a plasmid.

In an aspect, the present disclosure provides a cell, which comprises the attenuated flavivirus virus or the DNA.

In an aspect, the present disclosure provides a vaccine, which comprises the attenuated flavivirus virus, the DNA and/or the cell.

In an aspect, the present disclosure provides a pharmaceutical composition, which comprises the attenuated flavivirus virus, the DNA, the cell and/or the vaccine, and a pharmaceutically acceptable vector.

In an aspect, the present disclosure provides a method for preparing the attenuated flavivirus virus, the method comprising substituting all or a part of nucleotide sequence of a 3' untranslated region (3'UTR) of a wild-type virus with a polyadenylic acid (poly(A)) sequence.

In some preferred embodiments of the present disclosure, the attenuated flavivirus virus is obtained by means of rescue on baby hamster kidney cells BHK-21 and/or amplification on African green monkey kidney Vero cells.

In an aspect, the present disclosure provides use of the attenuated flavivirus virus, the DNA, and the cell in the preparation of an attenuated flavivirus virus vaccine.

In one preferred embodiment of the present disclosure, the use is use of the attenuated West Nile virus in the preparation of an attenuated West Nile virus vaccine.

In one preferred embodiment of the present disclosure, the use is use of the attenuated Japanese encephalitis virus in the preparation of an attenuated Japanese encephalitis virus vaccine.

In one preferred embodiment of the present disclosure, the use is use of the attenuated dengue virus in the preparation of an attenuated dengue virus vaccine.

In one preferred embodiment of the present disclosure, the use is use of the attenuated yellow fever virus in the preparation of an attenuated yellow fever virus vaccine.

In one preferred embodiment of the present disclosure, the use is use of the attenuated zika virus in the preparation of an attenuated zika virus vaccine.

In an aspect, the present disclosure provides use of the attenuated flavivirus virus, the DNA, the cell, the vaccine and/or the pharmaceutical composition in the preparation of a medicament for treating or preventing diseases caused by a flavivirus virus.

In one preferred embodiment of the present disclosure, the use is use of the attenuated West Nile virus in the preparation of a medicament for treating or preventing diseases caused by the West Nile virus.

In one preferred embodiment of the present disclosure, the use is use of the attenuated Japanese encephalitis virus in the preparation of a medicament for treating or preventing diseases caused by the Japanese encephalitis virus.

In one preferred embodiment of the present disclosure, the use is use of the attenuated dengue virus in the preparation of a medicament for treating or preventing diseases caused by the dengue virus.

In one preferred embodiment of the present disclosure, the use is use of the attenuated yellow fever virus in the preparation of a medicament for treating or preventing diseases caused by the yellow fever virus.

In one preferred embodiment of the present disclosure, the use is use of the attenuated zika virus in the preparation of a medicament for treating or preventing diseases caused by the zika virus.

In one aspect, the present disclosure provides a method for stimulating an immune response to a flavivirus virus, the method comprising immunological administration of the attenuated flavivirus virus, the DNA, the cell, the vaccine and/or the pharmaceutical composition.

An embodiment herein provides administration of a composition to a subject in a biocompatible form suitable for in vivo administration. "Biocompatible form suitable for in vivo administration" refers to a form of an active agent to be administered (e.g., a medicament in an embodiment), wherein a therapeutic effect of the active agent exceeds any toxic effect. The administration of a therapeutic composition in a therapeutically effective amount is defined as an effective amount in the dose and time period necessary to achieve a desired result. For example, the therapeutically active amount of a compound can vary with factors such as an individual's disease status, age, sex, and weight, as well as the ability of an antibody to elicit a desired response in an individual. A dosage regimen can be adjusted to provide an optimal response to treatment.

In one embodiment, a compound (e.g., a live attenuated virus in an embodiment) may be administered conveniently, e.g., by subcutaneous administration, intravenous administration, oral administration, inhalation, intradermal application, transdermal application, intravaginal application, topical administration, intranasal administration or rectal application. Depending on the route of administration, the active compound may be included in a protective buffer (e.g., albumin and trehalose, poloxamer 407/trehalose/albumin (FTA)). In one embodiment, the composition may be administered orally. In another embodiment, the composition may be administered intravenously. In one embodiment, the composition may be administered intranasally, for example, inhalation. In another embodiment, the composition may be administered intradermally using a needle-free system (e.g., Pharmajet®) or other intradermal application systems.

In certain embodiments, live attenuated virus vaccines (e.g., a West Nile virus vaccine) may be administered to children or young adults in the form of stable formulations (e.g., albumin and trehalose; FTA, or other formulations used to stabilize the live attenuated viruses). As used herein, a "pharmaceutically acceptable vector" may also include diluents, such as saline and an aqueous buffer solution. It may be necessary to combine a live attenuated virus formulation with a material that prevents its inactivation, or to apply the compound together with a material that prevents its inactivation. In certain embodiments, one or more formulations of a live attenuated West Nile virus may be administered subcutaneously or intradermally to a subject in an initial dose followed by a booster dose. Dispersants may also be prepared in glycerol, liquid polyethylene glycol and a mixture thereof, and in oil. Under normal storage and use conditions, these formulations may contain preservatives to prevent microbial growth or other stabilization formulations (e.g., for stabilizing live attenuated flaviviruses or other stable formulations).

Pharmaceutical compositions suitable for injectable use may be administered by means known in the art. For example, sterile aqueous solutions (in the case of water solubility) or dispersions and sterile powders for the immediate preparation of sterile injectable solutions or dispersions can be used. In some embodiments, the composition may be sterile and may be a fluid with ease of injectability. Pharmaceutically acceptable vectors may be solvents or dispersion media containing, for example, water, ethanol, polyols (e.g., glycerol, propylene glycol and liquid polyethylene glycol) and suitable mixtures thereof. For example, appropriate flowability may be maintained by using a coating material such as lecithin, by maintaining the desired particle size in the case of dispersions, and by using surfactants. Prevention of microorganisms can be achieved by adding various antibacterial agents or antifungal agents or other reagents.

In some embodiments, when formulated, a solution may be administered in compatibility with a dose formulation and administrated in a therapeutically effective amount. According to these embodiments, the formulation may be easily administered in a variety of dosage forms, such as the type of the injectable solution described above.

In certain embodiments, a single dose or multiple doses of attenuated flavivirus (e.g., West Nile virus) formulation may also be administered to a subject. In some embodiments, the subject may be treated with a single dose of formulation. In other embodiments, the subject may be treated with at least two doses of live attenuated West Nile virus formulations. In certain embodiments, the subject may be administered with an attenuated West Nile virus composition on day 0, and with a booster dose within about 3 months of the first dose. In certain embodiments, the subject is an unimmunized subject who has never been exposed to a West Nile virus (seronegative). In other embodiments, the subject may have been previously exposed to the West Nile virus and/or West Nile virus infection (seropositive). According to these embodiments, the seronegative subject may be treated on Day 0 and then accept a booster dose within 6 months, 5 months, 4 months, 3 months or less of the first dose in order to produce an enhanced immune response to the West Nile virus. In certain embodiments, the child may be a child from about 2 years old to about 17 years old. In other embodiments, the child may be 2 to 17 years old.

In another embodiment, a nasal solution or spray, aerosol or inhaler may be used to deliver a live attenuated flavivirus (e.g., a West Nile virus) virus formulation to the subject. Some formulations may contain excipients, e.g., pharmaceutical grade mannitol, lactose, starch, magnesium stearate, sodium saccharin, cellulose, and magnesium carbonate. A pharmaceutical composition may be prepared from a vector that protects active ingredients from rapid elimination from the body, e.g., releases a formulation or coating material on time. Such vectors may include controlled-release formulations such as, but not limited to, delivery systems for microencapsulation and biodegradable biocompatible polymers such as vinyl ethyleneacetate, polyanhydride, polyglycolic acid, polyorthoesters, polylactic acid and other known substances.

In certain embodiments, the dose range of the live attenuated flavivirus (e.g., West Nile virus) may be about 102 to about $10^6$ PFU initially administered and optionally, followed by at least a second administration within 30 days or up to 12 months thereafter as needed.

In certain embodiments, the pharmaceutical composition disclosed herein may be administered to the subject in one or more doses. In some embodiments, an immunogenic composition disclosed herein may be administered to the subject in a single dose or two or more within a predetermined period of time, including, but not limited to, within about 6 months, within about 120 days, within about 90 days, within about 80 days, within about 70 days, within about 60 days, within about 50 days, about 40 days, about 30 days, about 20 days, about 10 days, about 5 days or less, or administered to the subject within hours or minutes on the same day or simultaneously administered in the same or different anatomical locations. In some embodiments, the pharmaceutical compositions disclosed herein may be administered within about 90 days of each other, within about 60 days of each other, within about 30 days of each other, and within about less than 30 days of each other. In some embodiments, the composition disclosed herein may be administered to a subject subcutaneously or intradermally. Applications in two or more anatomical sites may include any combination of applications, including by the same pattern in two or more anatomical sites or by two different modes of separate anatomical sites. According to these embodiments, two or more anatomical sites may include different limbs or different areas of the body. In certain embodiments, two doses of vaccine composition may be continuously introduced into the subject on Day 0 in the same or multiple anatomical locations, e.g., to provide protection against all flavivirus (e.g., West Nile virus) sero-types (e.g., cross-protection). In other embodiments, the pharmaceutical composition may include a combination of a live attenuated West Nile virus with other other immuno-genic reagents against other flaviviruses (e.g., Zika virus, Japanese encephalitis virus, West Nile virus, St. Louis encephalitis virus, yellow fever virus, or other viruses). In certain embodiments, a vaccine against the West Nile virus disclosed herein may be used to reduce other related virus infections, such as Zika virus infection.

In some embodiments, the pharmaceutical composition disclosed herein may be used to increase an immune response of a target formulation in the subject, which is performed by combining immunogenic compositions against the flavivirus (e.g., West Nile virus) virus in children or young adults administrated with such pharmaceutical compositions against the flavivirus (e.g., West Nile virus) virus with reagents that enhance CD8$^+$T cell responses or other immune responses against the West Nile virus.

Topical application is accomplished by topical application of creams, gels, rinses, etc. containing therapeutically effec-tive amounts of serine protease inhibitor. Transdermal administration is accomplished through the application of creams, douches, gels, etc. that enable the serine protease inhibitor to penetrate the skin and enter the bloodstream. In addition, a permeation pump may be used for application. The necessary dose will vary depending on specific condi-tions being treated, a method of administration, and a rate at which molecules are cleared from the body.

Other embodiments relate to methods for reducing the inactivation of live attenuated viruses, including but not limited to combining one or more live attenuated viruses with compositions capable of reducing the inactivation of the live attenuated viruses (e.g., flavivirus). These compo-sitions may include, but are not limited to, one or more protein reagents; one or more sugar or polyol reagents; and optionally one or more EO-PO block copolymers, wherein the compositions may reduce the inactivation of the acti-vated attenuated viruses or stabilize the activated attenuated viruses.

In certain embodiments, the compositions covered herein may be partially or completely dehydrated or hydrated. In other embodiments, a stable protein reagent comprising the pharmaceutical or non-pharmaceutical composition used herein may include, but is not limited to, whey protein, human serum albumin, recombinant human serum albumin (rHSA), bovine serum albumin (BSA), other serum albumin or albumin gene family members. Sugar or polyol reagents may include, but are not limited to, monosaccharides, disac-charides, sugar alcohols, trehalose, sucrose, maltose, iso-maltose, cellobiose, gentiobiose, laminaribose, xylobiose, mannobiose, lactose, fructose, sorbitol, mannitol, lactitol, xylitol, erythritol, raffinose, amylase, cyclodextrin, chitosan, or cellulose. In certain embodiments, surfactants may include, but are not limited to, nonionic surfactants, such as an alkyl poly(ethylene oxide), poly(ethylene oxide) and poly(propylene oxide) copolymer (EO-PO block copoly-mer), poly(vinyl pyrrolidone), alkyl polyglycoside (e.g., sucrose monostearate, lauryl diglucoside or sorbitan monolaureate, capryl glucoside and decyl maltoside), fatty alcohol (cetyl alcohol or olelyl alcohol or cocamides (cocamide MEA, cocamide DEA and cocamide TEA).

In other embodiments, surfactants may include, but are not limited to, poloxamer 407 (e.g., Pluronic F127®), alter-native poloxamer 407 or poloxamer 335, 338 or 238 other than poloxamer 407, or other EO-PO block copolymers having similar properties to F127®.

In some embodiments, a vaccine composition may include, but is not limited to, one or more protein reagents, which are serum albumin; one or more trehalose sugars; and one or more surfactant polymer reagents, such as an EO-PO block copolymer, poloxamer 407 or, more specifically, Pluronic F127®.

In other embodiments, formulations for stabilizing live viruses may comprise one or more live flaviviruses, one or more carbohydrate reagents and one or more amino acids or salts, esters or amide derivatives thereof. In other embodi-ments, the formulations used herein stabilizes the activated attenuated flavivirus for commercial use. In some embodi-ments, the composition further comprises a buffer. Accord-ing to these embodiments, the buffer may include, but are not limited to, phosphate-buffered saline (PBS). According to these embodiments, the buffer may include at least one of sodium chloride (NaCl), monosodium phosphate and/or disodium phosphate (Na$_2$HPO$_4$), potassium chloride (KCl) and potassium phosphate (KH$_2$PO$_4$). In some embodiments, the buffer of the composition may comprise sodium chloride having a concentration of 25 mM to 200 mM. In other embodiments, the composition disclosed herein may com-prise other suitable reagents, such as urea and/or MSG.

In some embodiments, live attenuated flaviviruses such as a West Nile virus may be stabilized in formulations, the formulations comprising but not limited to: recombinant HSA having a concentration of 0.1% to 0.2% (w/v); and/or sucrose having a concentration of about 4.0% to about 6.0% (w/v); and/or mannitol having a concentration of about 2% to 4% (w/v); and/or alanine having a concentration of about 8.0 mM to about 22.0 mM; and/or methionine having a concentration of about 1.0 mM to about 5.0 mM; and/or MSG having a concentration of about 8.0 mM to 12.0 mM; and/or urea having a concentration of about 0.1% to about 0.3% (w/v). In certain embodiments, the composition may comprise recombinant HSA, trehalose, mannitol, alanine, methionine, MSG and urea. In other embodiments, the stabilization composition may comprise HSA having a con-centration of about 0.1% to about 0.2% (w/v); trehalose having a concentration of about 4% to about 6% (w/v); mannitol having a concentration of about 2% to about 4% (w/v); alanine having a concentration of 8 mM to 22 mM; methionine having a concentration of 1 mM to 5 mM; MSG having a concentration of 8 mM to 12 mM; urea having a concentration of 0.1% to 0.3% (w/v). Certain formulations for stabilizing live attenuated viruses may include, but are not limited to, recombinant HSA, sucrose, alanine, and urea. According to these embodiments, the HSA concentration may be about 0.1% to about 0.2% (w/v); the sucrose concentration may be about 4% to about 6% (w/v); the alanine concentration may be about 8.0 mM to about 22 mM, and the urea concentration may be about 0.1% to about 0.3% (w/v). Other stabilization formulations may include recombinant HSA, sucrose, methionine, and urea. The recombinant HSA concentration may be about 0.1% to 0.2% (w/v); the sucrose concentration may be about 4.0% to about 6.0% (w/v); the methionine concentration may be about 1.0 mM to about 5.0 mM, and the urea concentration may be about 0.1% to about 0.3% (w/v). In other embodiments, the stabilization formulation may comprise recombinant HSA, sucrose, arginine, and urea, wherein the recombinant HSA concentration may be 0.1% to 0.2% (w/v); the sucrose concentration may be 4% to 6% (w/v); the arginine concentration may be 10 mM to 50 mM; and the urea concentration may be 0.1% to 0.3% (w/v). Other stabilization formulations may include recombinant HSA, trehalose, arginine, and urea, wherein the recombinant HSA concentration is about 0.1% to 0.2% (w/v); the trehalose concentration is about 4% to 6% (w/v); the arginine concentration is about 10 mM to 50 mM; and the urea concentration is about 0.1% to 0.3% (w/v). In other embodiments, the stabilization composition may include recombinant HSA, trehalose, MSG and urea. According to these embodiments, the HSA concentration may be about 0.1% to about 0.2% (w/v); the trehalose concentration may be about 4.0% to about 6.0% (w/v); the MSG concentration may be 8.0 mM to 22 mM, and the urea concentration may be 0.1% to 0.3% (w/v). Some embodiments herein relate to a live attenuated virus composition for partial or complete dehydration caused by transport or other reasons. According to these embodiments, the composition may be dehydrated by 20% or more; 30% or more; 40% or more; 50% or more; 60% or more; 70% or more; 80% or more; or 90% or more. According to these embodiments, prior to administering a pharmaceutically acceptable composition to a subject, a virus vaccine composition may be dehydrated and rehydrated in any known stabilization composition.

In certain embodiments, the subject may be a mammal, such as a human or a veterinarian and/or a domesticated animal or a domestic animal or wild animal. In certain embodiments, the immunogenic composition disclosed herein may be effective in immunizing juvenile subjects, such as human children aged 20 years or younger. Although the prior art related to current dengue virus vaccines/immunogenic compositions (e.g., dengue/yellow fever chimera) used in children has reported low efficacy and/or immunogenicity in children aged 9 years or younger, immunogenic compositions disclosed herein can produce effective immune responses in children aged about 1 to about 17 years or about 1 to about 9 years or older. Compared with the prior art, the immunogenic composition disclosed herein exhibits excellent efficacy and immunogenicity.

In certain embodiments, immunogenic compositions against flaviviruses (e.g., West Nile virus) may include one or more of the followings: an attenuated West Nile virus having a concentration of about $1.0 \times 10^3$ to about $5 \times 10^5$ PFU; a live West Nile virus having a concentration of about $1.0 \times 10^3$ to about $5 \times 10^5$ PFU; an attenuated West Nile virus having a concentration of about $5.0 \times 10^3$ to about $5 \times 10^5$ PFU; and/or an attenuated West Nile virus having a concentration of about $1.0 \times 10^4$ to about $5 \times 10^6$ PFU. In some embodiments, the subject treated by the composition and method disclosed herein may be treated 2 times a year, annually, 18 months, or a similar regimen, depending on, for example, a location and travel plan of the subject. In certain embodiments, immunogenic compositions against the West Nile virus may include one or more of the followings: an attenuated West Nile virus having a concentration of about $2.0 \times 10^4$ PFU; a live West Nile virus having a concentration of about $5.0 \times 10^3$ PFU; an attenuated West Nile virus having a concentration of about $1 \times 10^5$ PFU; and/or an attenuated West Nile virus having a concentration of about $3.0 \times 10^5$ PFU.

Compared with the prior art, the present invention has the following advantages and effects.

1. A reverse genetics technology used in the present disclosure to construct attenuated flavivirus viruses (such as an attenuated West Nile virus strain WNV-poly(A)) has the advantages of advanced maturity, convenience, simplicity, and controllable positioning.

2. The attenuated flavivirus virus (e.g., WNV-poly(A)) provided in the present disclosure can be cultivated and amplified in Vero to obtain a high-titer virus, which is simple to obtain, thereby facilitating the production of subsequent vaccines and saving the cost.

3. The attenuated flavivirus virus (e.g., WNV-poly(A)) provided in the present disclosure maintains the sequence deletion of SL and DB regions and the stability of a -poly(A) sequence during continuous passage of 3'UTR, thereby achieving good genetic stability.

4. The attenuated flavivirus virus (e.g., WNV-poly(A)) provided by the present disclosure which infects C57BL/6 mice at high dose does not cause any illness, has been shown to be sufficiently attenuated in mice, and is thus high in security. A single immunization of $10^4$-$10^7$ PFU of WNV-poly(A) can enable the mice to produce high levels of WNV-specific IgG antibodies and neutralizing antibodies, which can provide complete immune protection for the mice after being challenged at a high lethal dose of WT WNV.

5. The attenuated flavivirus virus (e.g., WNV-poly(A)) provided by the present disclosure is immunized at low dose ($10^4$ PFU) or high dose ($10^7$ PFU) in a C57BL/6 mouse model to maintain a high humoral immune response for a long time, the level of neutralizing antibodies remains stable, and complete immune protection is still provided to the mice after being challenged at a high lethal dose of WT WNV.

The above results show that the general preparation method of the attenuated flavivirus strain provided in the present disclosure can be used to prepare safe and effective attenuated vaccine strains, which have good application prospects and important strategic significance for China and the world to deal with the potential threat of flavivirus.

The experimental methods of plasmid linearization, RNA in vitro transcription, transfection, viral titer determination, etc. mentioned in this section are routinely used in the art unless otherwise specified. The followings are only several specific embodiments of the present disclosure. Obviously, the present disclosure is not limited to the following embodiments, and may have many variations. Therefore, modifications or improvements made by those skilled in the art on the basis of the present disclosure should fall within the protection scope of the present disclosure.

Example 1: Construction of Attenuated Flavivirus Strain Clone and Virus Rescue

1. Construction of Attenuated Flavivirus Strain

A schematic diagram of the construction of an attenuated flavivirus strain is shown in FIG. 1.

Using a plasmid DNA from an infectious clone of a wild-type (WT) West Nile virus (WNV) strain as a framework, an attenuated strain plasma of the WNV-poly (A) virus is obtained by deleting sequences from SLI to CS2 in a 3' untranslated region (3'UTR) of WNV (including a 5'-end stem loop region I (SLI), a stem loop region II (SLII), a repetitive cyclization region 3 (RCS3), a stem loop region III (SLIII), a stem loop region IV (SLIV), a cyclization sequence region 3 (CS3), a dumbbell region 1 (DB1), a repetitive cyclization region 2 (RCS2), a dumbbell region (DB2), and a cyclization sequence region 2 (CS2)), retaining the cyclization sequence region 1 (CS1) and a short hairpin-3' stem loop region (sHP-3'SL) behind the cyclization sequence region 1 in the 3' untranslated region, and inserting a poly(A) sequence (130 adenylates) to a deletion site resulting from deletion of the sequences from SLI to CS2, and a nucleotide sequence of the attenuated strain plasma is shown in SEQ ID NO. 1.

Using a plasmid DNA from an infectious clone of a wild-type (WT) Japanese encephalitis virus strain (JEV) as a framework, an attenuated strain plasma of the JEV-poly (A) virus is obtained by deleting sequences from SLI to CS2 in a 3' untranslated region (3'UTR) of JEW (including SLI, SLII, RCS3, SLIII, SLIV, CS3, DB1, RCS2, DB2 and CS2), retaining a cyclization sequence region 1 (CS1) and a short hairpin-3' stem loop region (sHP-3'SL) behind the cyclization sequence region 1 in the 3' untranslated region, and inserting a poly(A) sequence (150 adenylates) to a deletion site resulting from deletion of the sequences from SLI to CS2, and a nucleotide sequence of the attenuated strain plasma is shown in SEQ ID NO. 2.

Using a plasmid DNA from an infectious clone of a wild-type (WT) dengue virus type-2 New Guinea Island strain (DENV-2 (NGC)) as a framework, an attenuated strain plasma of the DENV-2 (NGC)-poly (A) virus is obtained by deleting sequences from SLII to CS2 in a 3' untranslated region (3'UTR) of DENV-2 (NGC) (including SLII, RCS3, SLIV, CS3, DB1, RCS2, DB2 and CS2), retaining a cyclization sequence region 1 (CS1) and a short hairpin-3' stem loop region (sHP-3'SL) behind the cyclization sequence region 1 in the 3' untranslated region, and inserting a poly(A) sequence (140 adenylates) to a deletion site resulting from deletion of the sequences from SLI to CS2, and a nucleotide sequence of the attenuated strain plasma is shown in SEQ ID NO. 3.

Using a plasmid DNA from an infectious clone of a wild-type (WT) yellow fever virus (YFV) strain as a framework, an attenuated strain plasma of the YFV-poly (A) virus is obtained by deleting sequences from SLII to CS2 in a 3' untranslated region (3'UTR) of YFV (including SLII, RCS3, and DB), retaining a stem loop region (SL), a cyclization sequence region 1 (CS1) and a short hairpin-3' stem loop region (sHP-3'SL) behind the cyclization sequence region 1 in the 3' untranslated region, and inserting a poly(A) sequence (130 adenylates) to a deletion site resulting from deletion of the sequences from SLI to CS2, and a nucleotide sequence of the attenuated strain plasma is shown in SEQ ID NO. 4.

The plasmids of the above strains are all obtained by replacing all or a part of the 5'-end stem loop region (SL) sequence and all of the DB sequence in the 3'UTR region with the poly(A) sequence, retaining at least the cyclization sequence region 1 (CS1) and the short hairpin-3' stem loop region (sHP-3'SL) behind the cyclization sequence region 1 in the 3' untranslated region, thereby obtaining the corresponding poly(A) virus attenuated strain plasmids.

2. In Vitro Transcription of Poly(A) into RNA

The plasmid of the attenuated strain of the poly(A) virus obtained in step 1 is linearized, after complete linearization is identified by 0.8% agarose gel electrophoresis, extracted with phenolic chloroform, and finally added with 11 μL of RNAase-free water to dissolve; and the concentration of DNA is determined using Thermo Scientific NanoDrop 2000 and the quality of DNA is detected by electrophoresis. Taking 1 μg of DNA extracted with phenolic chloroform as a template, an in vitro transcription kit T7 mMESSAGE mMACHINE kit (Ambion) is used, an in vitro transcription is performed according to kit instructions to obtain a recombinant poly(A) RNA, namely a genomic RNA of attenuated strains of WNV-poly(A), JEV-poly(A), DENV-2(NGC)-poly(A) and YFV-poly(A) viruses. The concentration of RNA is determined using Thermo Scientific NanoDrop 2000 and the quality of RNA is detected by electrophoresis with 0.8% freshly prepared agarose gel, and the RNA is stored at −80° C. for later use.

3. Poly(A) Virus Rescue

The experiment is divided into the following two groups:
(1) experimental group: a recombinant poly(A) RNA obtained by in vitro transcription in step 2 is transfected into BHK-21 cells by means of liposome transfection; and
(2) control group: a wild-type virus RNA is transfected into BHK-21 cells by means of liposome transfection as a positive control.

The specific experimental steps are as follows: on the day before transfection, $2 \times 10^5$ BHK-21 cells are inoculated into 35 mm cell culture dishes, with three 10 mm×10 mm coverslips being placed in each dish, such that about 80% of the cells are transfected on the day of transfection; duration transfection, medium in each dish is discarded, and the dish is washed once with 1 ml of Opti-MEM, and added with 1 ml of Opti-MEM (to keep the cells in an infiltrated state); 1 ml of Opti-MEM is added to a 1.5 ml EP tube, added with 4 μl of DMRIE-C (mixed well before use of DMRIE-C) and mixed well upside down, 1 μg of recombinant poly(A) RNA obtained by in vitro transcription is added to the experimental group respectively, and 1 μg of wild-type virus RNA is added into the control group and mixed well upside down; 1 μg of wild-type virus RNA is added to the control group and mixed well upside down; Opti-MEM in the dish is quickly discarded and the mixture is added to the dish softly (do not blow or bit the cells); and after incubation in a 37° C., $CO_2$ incubator for 4 h, the culture is discarded, and 2 mL of DMEM medium containing 2% FBS is added to each dish. A cell status of the experimental group and a cell status of the control group are observed under a microscope, and a glass slide is respectively taken 24, 48 and 72 h after transfection, and the cells are immobilized with a 5% acetone immobilization solution (purchased from Sinopharm Chemical Reagent Company); the cells are immobilized at room temperature for 15 minutes, washed with PBS three times, and stored at 4° C.; when a positive rate of IFA detection is high, supernatants are respectively collected as poly(A) P0-generation viruses of attenuated flaviviruses, that is, four P0-generation attenuated WNV-poly(A), JEV-poly(A), DENV-2(NGC)-poly(A) and YFV-poly(A) strains are obtained and stored at −80° C.

4. Indirect Immunofluorescence (IFA) to Detect Virus Protein Expression of Recombinant Poly(A)

The slide stored at 4° C. in step 3 above is incubated at room temperature to obtain a primary antibody, and the attenuated flavivirus strain antibody is a 1:500-fold diluted 4G2 monoclonal antibody (general flavivirus E protein antibody). The primary antibody is incubated for 1-2 h at room temperature, and rinsed with PBS for 10 times, and a secondary antibody is incubated at room temperature in the dark, wherein the secondary antibody is a 1:125-fold diluted conjugated fluorescein isothiocyanate (FITC) sheep anti-mouse antibody. After 1 h of incubation, the secondary antibody is rinsed with PBS for 10 times, the slide is taken out and marked. At each marker, 95% glycerol is dispensed. The coverslip with is placed on glycerol droplets with the side containing the cells facing downward, and observed under a fluorescence microscope at a 200× magnification (FIG. 1).

The results in FIG. 1 show that the positive rate of each of attenuated WNV-poly(A), JEV-poly(A), DENV-2(NGC)-poly(A) and YFV-poly(A) strains at each time point is lower than that of WT, but with the prolongation of incubation time after transfection, the number of positive cells gradually increases, which is consistent with the trend of WT, indicating that WNV-poly(A), JEV-poly(A), DENV-2(NGC)-poly(A) and YFV-poly(A) all rescue infectious virus particles.

Figure 2:
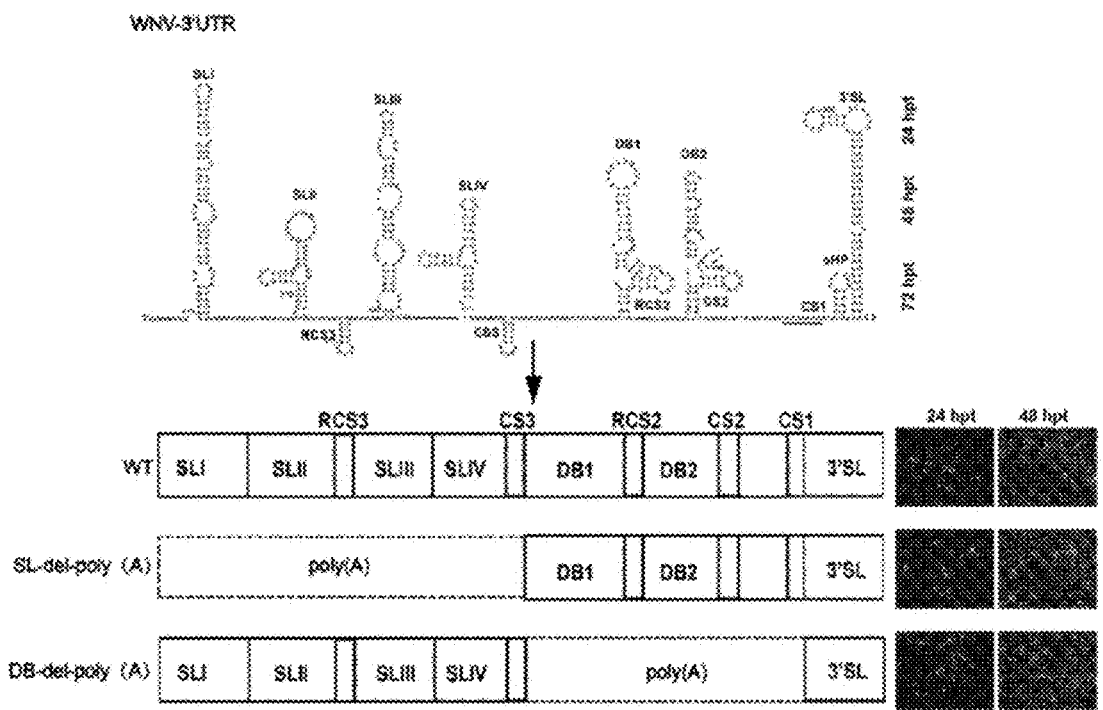
FIG. 2 shows a schematic diagram of clone construction of other attenuated West Nile virus strain, and virus rescue.

Example 2: Construction of Other Attenuated West Nile Virus Strain Clone and Virus Rescue 1. Construction of Other Attenuated West Nile Virus Strain Clone a Schematic Diagram of the Other Attenuated West Nile Virus Strain Clone is Shown in FIG. 2.

Using a plasmid DNA from an infectious clone of a wild-type (WT) West Nile virus (WNV) strain in the example 1 as a framework, an attenuated strain plasma of the West Nile virus SL-del-poly (A) is obtained by deleting sequences from SLI to CS3 in a 3' untranslated region (3'UTR) of MNV (including SLI, SLII, RCS3, SLIII, SLIV, and CS3), retaining a dumbbell region 1 (DB1), a repetitive cyclization sequence region 2 (RCS2), a dumbbell region 2 (DB2), a cyclization sequence region 2 (CS2), a cyclization sequence region 1 (CS1) and a short hairpin-3' stem loop region (sHP-3'SL) behind the cyclization sequence region 1 in the 3' untranslated region, and inserting a poly(A) sequence (130 adenylates) to a deletion site resulting from deletion of the sequences from SLI to CS3 to obtain a plasmid of attenuated strain of West Nile virus SL-del-poly (A) deleted in the stem loop region (SL).

Using a plasmid DNA from an infectious clone of a wild-type (WT) West Nile virus (WNV) strain in the example 1 as a framework, an attenuated strain plasma of the West Nile virus DB-del-poly (A) from which a dumbbell region (DB) is deleted is obtained by deleting sequences from DBI to CS1 in a 3' untranslated region (3'UTR) of MNV (including DB1, RCS2, DB2, CS2 and CS1), retaining a 5'-end stem loop region I (SLI), a stem loop region II (SLII), a repetitive cyclization sequence region 3 (RCS3), a stem loop region III (SLIII), a stem loop region IV (SLIV), a cyclization sequence region 3 (CS3) and a short hairpin-3' stem loop region (sHP-3'SL) in the 3' untranslated region, and inserting a poly(A) sequence (130 adenylates) to a deletion site resulting from deletion of the sequences from DB1 to CS1 to obtain a plasmid of attenuated strain of West Nile virus DB-del-poly(A) deleted in the dumbbell region (DB).

2. In Vitro Transcription of Poly(A) into RNA

The transcription method is described in step 2 of Example 1.

3. Poly(A) Virus Rescue

The rescue method is described in step 3 of Example 1.

4. Indirect Immunofluorescence (IFA) to Detect Virus Protein Expression of Recombinant Poly(A)

The detection method is described in step 4 of Example 1.

The observation results of the fluorescence microscope are shown in FIG. 2. Results in FIG. 2 show that the virus obtained by deleting a part of the nucleotide sequence of the 3' untranslated region (3'UTR) of the flavivirus virus, without missing all 5'SL and DB, and inserting the poly(A) sequence to the deletion site, can also produce toxins.

Example 3: Comparison of Growth Curve of Attenuated Flavivirus Strain and Growth Curve of Wild-Type Virus 1. Virus Titer Determination The titers of the virus are determined by plaque phagocytosis according to the follow specific steps:

$1 \times 10^5$ BHK-21 cells are inoculated in each well of a 24-well cell culture plate, and when the cell confluency reaches 90%, a medium in the wells is discarded; and 100 μl of poly(A) P0-generation virus of an attenuated flavivirus, which is collected with a 10-fold diluted DMEM medium containing 2% FBS in step 3 of Example 1, is added, adsorbed at 37° C. for 1 h, and shaken well every 15 min. After adsorption, the virus liquid of each well is discarded by suction, a DMEM medium containing 2% FBS and a covering of 2% methylcellulose are added, and inoculated in a 37° C., 5% $CO_2$ incubator for 3 days, stained with a staining solution containing 1% crystal violet and 3.7% formaldehyde after the formation of plaques, and treated at room temperature for 30 min; and the staining solution in the wells are taken out, the bottoms of the wells are rinsed with running water and dried, and then the virus titers are obtained by counting and conversion.

Figure 3:
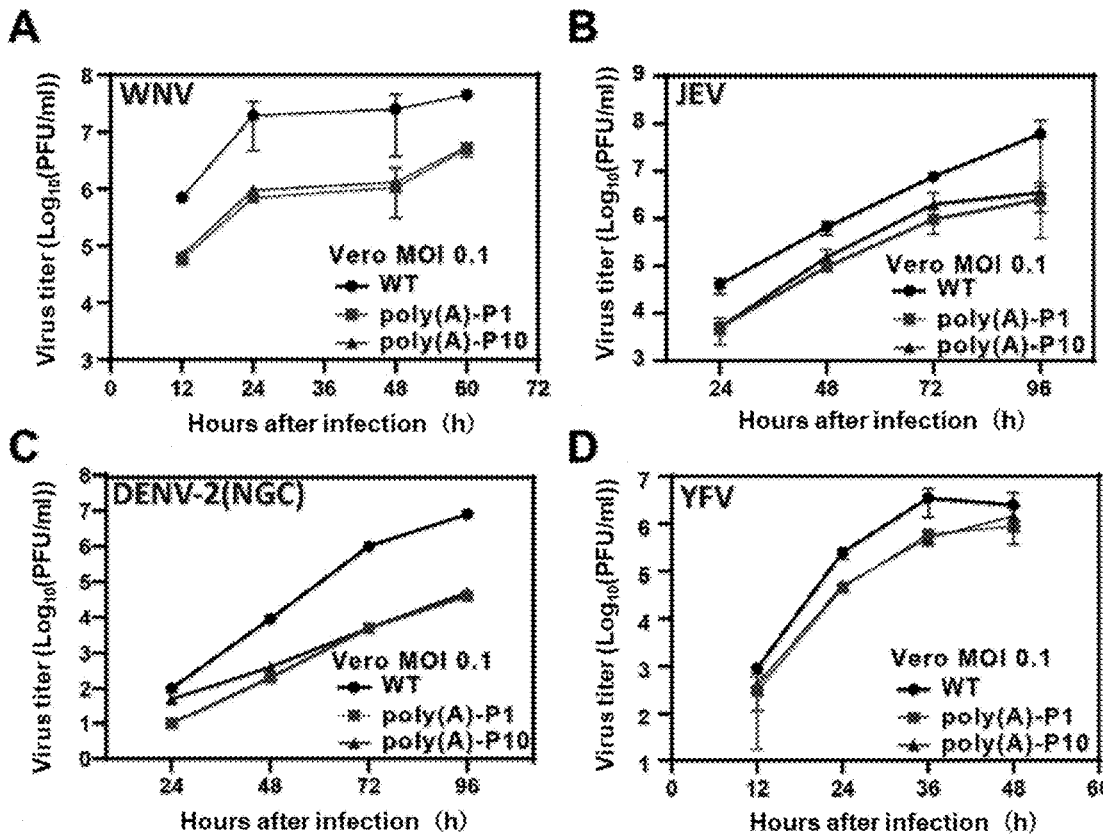
FIG. 3 shows comparisons of a growth curve of an attenuated flavivirus strain in which 3'UTR is replaced with a poly(A) sequence with a growth curve of a wild-type virus, wherein: A: a comparison of a growth curve of a attenuated WNV-poly(A) strain with a growth curve of a corresponding wild-type virus strain; B: a comparison of a growth curve of a JEV-poly(A) strain with the growth curve of the corresponding wild-type virus strain; C: a comparison of a growth curve of a DENV-2(NGC)-poly(A) strain and the growth curve of the corresponding wild-type virus strain; and D: a comparison of a growth curve of a YFV-poly(A) strain with the growth curve of the corresponding wild-type virus strain.

2. Determination of Growth Curves of Viruses $2 \times 10^6$ Vero cells are inoculated in 35 mm cell culture dishes; under the culture conditions at 37° C. and in 5% $CO_2$, when the confluency reaches 60%, the poly(A) P0-generation virus collected in step 3 of Example 1 and the corresponding wild-type (WT) virus are added to each dish according to the multiplicity of infection MOI 0.1, and adsorbed in a 37° C., 5% $CO_2$ incubator for 2 h, and then the virus liquid is discarded; 2 ml of DMEM medium containing 2% fetal bovine serum is added to each well and incubated under the incubation conditions at 37° C. and in 5% $CO_2$; 400 μl of virus supernatant is collected and supplemented with 400 μl of DMEM medium containing 2% fetal bovine serum every 12 h after infection; and the collected viruses are used as virus samples at different time points under the same multiplicity of infection between the poly(A) virus and the corresponding WT virus, and stored at −80° C. The viral titers collected at different time points are determined according to the plaque assay described above and the growth curves are plotted (FIG. 3). The results show that attenuated WNV-poly(A), JEV-poly(A), DENV-2(NGC)-poly(A) and YFV-poly(A) strains have similar growth trends compared with the corresponding WT, while the titers thereof are each 10-100 times lower than that of the wild type.

Figure 4:
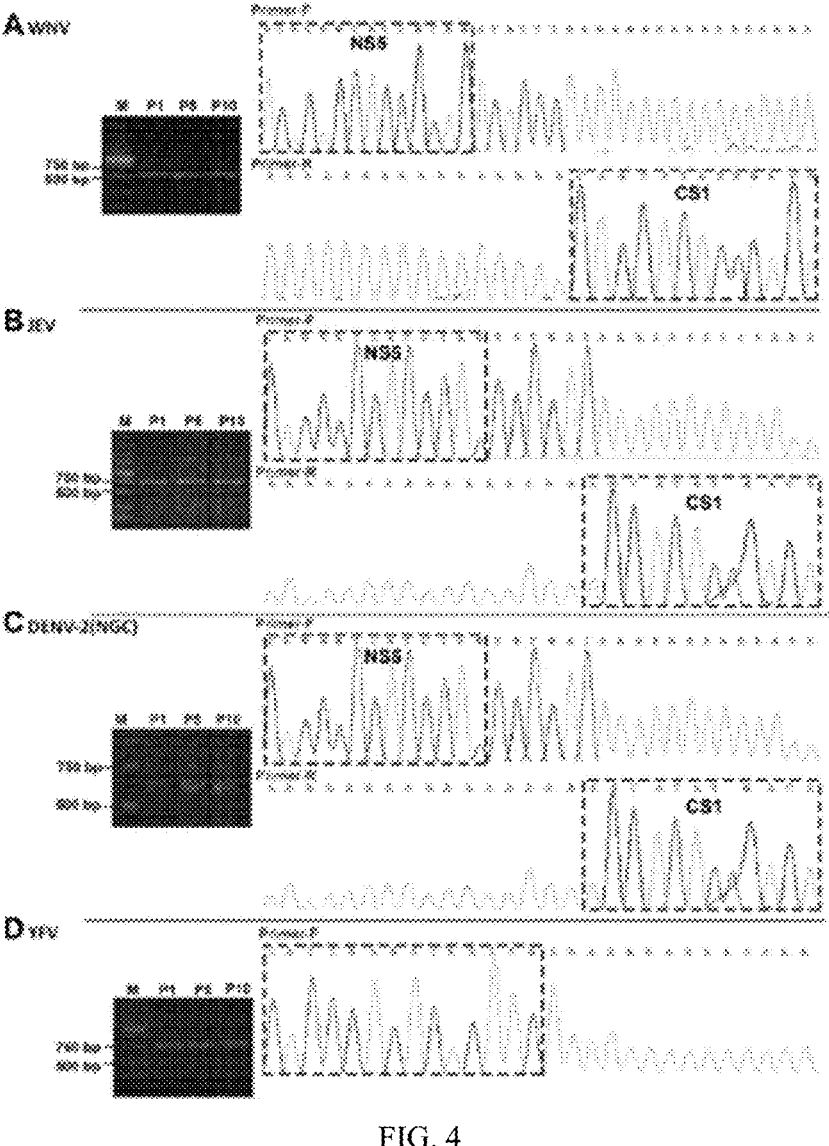
FIG. 4 shows genetic stability verifications of attenuated flavivirus strains in which 3'UTR is replaced with a poly(A) sequence, wherein: A: a genetic stability verification of an attenuated WNV-poly(A) strain; B: a genetic stability verification of an attenuated JEV-poly(A) strain; C: a genetic stability verification of an attenuated DENV-2(NGC)-poly (A) strain; and D: a genetic stability verification of an attenuated YFV-poly(A) strain.

Example 4: Verification of Genetic Stability of Attenuated Flavivirus Strains 1. The poly(A) P0-generation virus of the attenuated flavivirus obtained by rescue in Example 1 is used to infect Vero cells, and after 3 days, the cytopathic effect (CPE) is obvious; a cellular supernatant (P1 generation) is collected, and three virus strains are passaged in parallel in each generation, and blindly passaged for 10 consecutive passages; and an RNA of the virus is extracted from virus-infected cell samples collected in the P1, P5, and P10 generations according to the instructions of a Trizol kit, and stored at −80° C. for later use. RT-PCR is performed with PrimeScript One Step RT-PCR Kit to detect changes in 3'UTR, followed by sequencing. The sequencing results show that WNV-poly(A), JEV-poly(A), DENV-2(NGC)-poly(A), and YFV-poly(A) are continuously passaged for 10 generations, while polyA insertion locations and number remained essentially unchanged, about 130-150 A (FIG. 4).

2. The virus supernatant collected by P1 and P10 generations is taken for comparison of the growth curves in Vero cells according to the multiplicity of injection MOI of 0.1 (the method is the same as Example 2); and the results are shown in poly(A)-P10 markers in FIG. 4, indicating that the growth curves of WNV-poly(A), JEV-poly(A), DENV-2 (NGC)-poly(A) and YFV-poly(A) virus strains in respective P1 and P10 generations are similar, further indicating that the above poly(A) virus has good genetic stability.

Example 5: Pathogenicity of Attenuated West Nile Virus

This example investigates the pathogenicity of attenuated West Nile virus (WNV) strain WNV-poly(A) on C57BL/6.

Six groups of 4-week-old female C57BL/6 mice (5 mice/group) are taken and infected intraperitoneally with $10^4$ PFU, $10^5$ PFU, $10^6$ PFU or $10^7$ PFU of P1-generation attenuated WNV-poly(A) strain obtained in Example 3 and $10^4$ PFU of corresponding wild-type West Nile virus (WT WNV), and mice injected with equal volume of PBS are used as controls. On Days 1, 2, and 3 after infection, blood toxicity determination is performed by detecting the virus titers in the serum of mice. The specific method includes: collecting about 100 μl of blood from the orbit of each mouse and putting it in a 1.5 ml EP tube, standing at 4° C. for 3 h, then collecting the serum by centrifugation at 5000 rpm for 5 min for virus titer determination. The determination regimen is the same as the virus titer determination in Example 1. The mice are weighed for 14 consecutive days after simultaneous infection and the survival statuses of the mice are observed within 21 days.

The results show that the mice inoculated with the attenuated WNV-poly(A) strain all survive (FIG. 5A), and no viremia is detected in other doses except for the mice inoculated with $10^7$ PFU of attenuated WNV-poly(A) strain being detected to have slight viremia on the first day (B in FIG. 5); and the changes in body weight are consistent with the changes in a PBS immune group (C in FIG. 5) and no other pathogenesis is observed. However, the mice inoculated with $10^4$ PFU of WT WNV manifest hyper viremia (B in FIG. 5), with significant weight loss from Day 5 (C in FIG. 5), and all die on Day 8 (A in FIG. 5). It is shown that the attenuated WNV-poly(A) strain has sufficiently reduced virulence, does not cause a disease in the C57BL/6 mice, has high safety, and can be used as a potential live attenuated vaccine.

Example 6: Humoral Immunity and Challenge Protection Effects of Attenuated West Nile Virus in Mouse Model This example investigates the humoral immunity and challenge protection effects of an attenuated WNV-poly(A) strain in a C57BL/6 mouse model.
1. The Humoral Immunity of the Attenuated WNV-Poly(A) Strain in a C57BL/6 Mouse Model Six groups of 4-week-old female C57BL/6 mice (5 mice/group) are taken and infected intraperitoneally with $10^4$ PFU, $10^5$ PFU, $10^6$ PFU or $10^7$ PFU of attenuated P1-generation WNV-poly(A) strain obtained in Example 3, and mice in a Mock group which are immunized with equal volume of PBS and the mice in the Mock group which are not treated are used as controls. On Days 14 and 28 after immunization, blood is collected according to an orbital blood collection method in Example 4, and serum is collected by centrifugation after standing at 4° C. for 3 h, inactivated at 56° C. for 30 min, and frozen at −20° C. for later use.

IgG antibody titers are detected by ELISA and neutralizing antibody titers are detected by PRNT50, respectively:
1) Detection of IgG Antibody Titers by ELISA A 96-well plate is coated with an attenuated WNV-poly (A) strain and blocked with 5% skim milk prepared from PBS; serum is subjected to 4-fold serial dilution from 1:50 and then incubated with the coated 96-well plate at 37° C. for 2 h; after the plate is washed with PBST for three times, an HRP sheep anti-mouse antibody is incubated at 37° C. for 1 h, and developed with a two-component chromogenic kit (Proteintech); after the addition of 1 M $H_2SO_4$ for termination, an absorbance value at 450 nm is detected with a multifunctional microplate reader; and the IgG antibody titer is the highest dilution when the serum absorbance value of immunized mice is 2 times the serum absorbance value of unimmunized mice.
2) Detection of Neutralizing Antibody Titers by PRNT50

$2\times10^5$ BHK-21 cells are inoculated in each well of a 12-well cell culture plate, respectively; when the cell confluency reaches 90%, the serum is first subjected to 2-fold serial dilution; 100 l of diluted antibody and an equal volume of 100 PFU of WT-WNV are well mixed and incubated at 37° C. for 1 h; the medium in the wells is discarded, and the incubated serum-virus mixture is added to the corresponding wells, adsorbed at 37° C. for 1 h, and shaken well every 15 min; after adsorption, the virus solution in each well is discarded by suction, 1 mL of covering containing 2% methylcellulose is added, incubated in an 37° C., 5% $CO_2$ incubator for 72 h, stained with a staining solution containing 1% crystal violet and 3.7% formaldehyde after the formation of plaques, and treated at room temperature for 30 min; the staining solution is removed from the wells and the bottoms of the wells are rinsed with running water, and after drying, the virus titers after serum neutralization can be counted at each dilution; and the neutralizing antibody titer (PRNT50) in serum is the highest dilution of serum when the virus titer is neutralized by 50%.

Figures 5, 6:
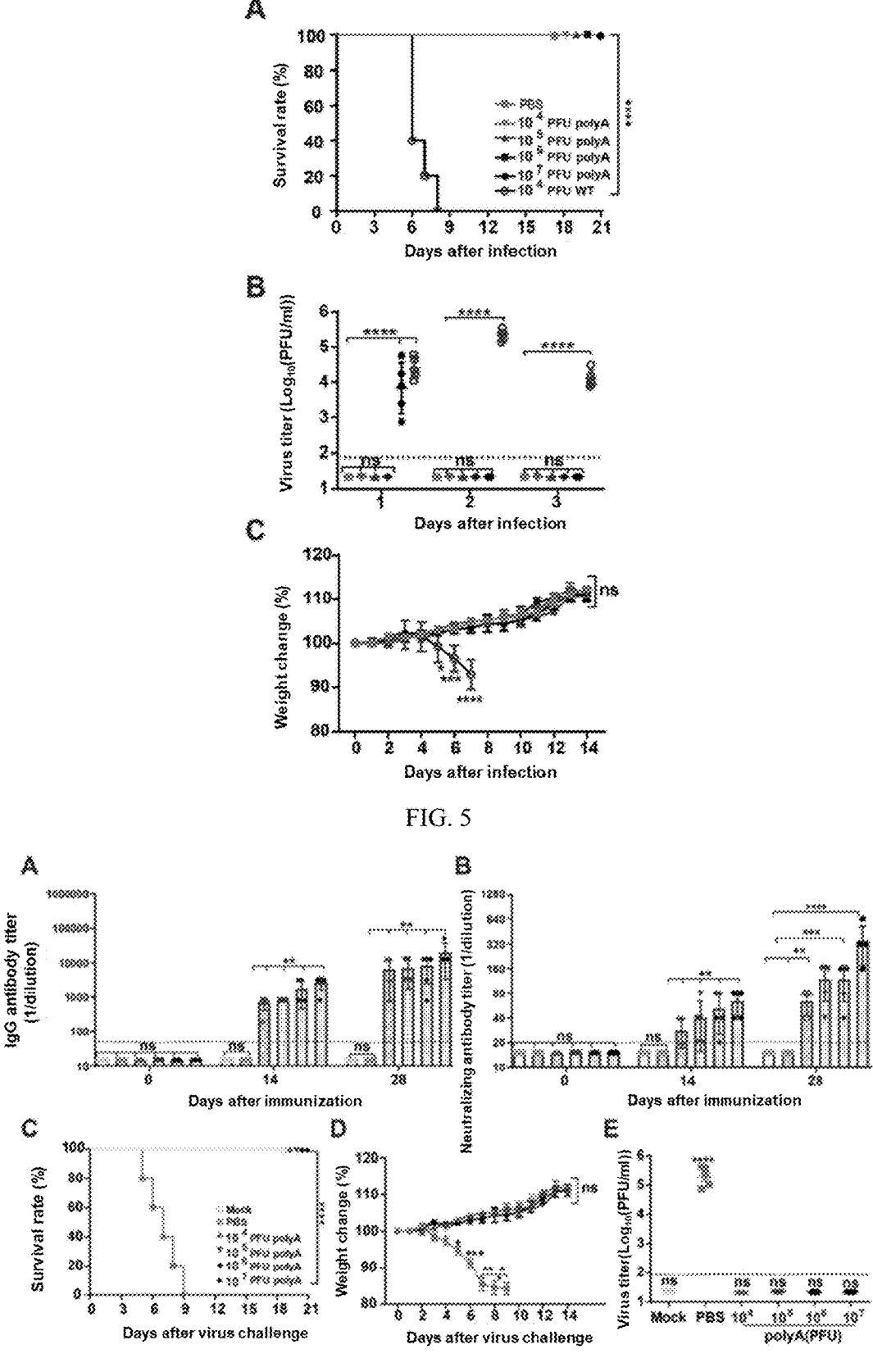
FIG. 5 shows pathogenicity detection of WNV-poly(A) on C57BL/6, wherein: A: a survival rate of mice immunized with an attenuated WNV-poly(A) strain; B: a blood toxicity status of the mice immunized with the attenuated WNV-poly(A) strain; and C: body weights of the mice immunized with the attenuated WNV-poly(A) strain.
FIG. 6 shows an immunoprotective experiment of WNV-poly(A) on a C57BL/6 mouse model, wherein: A: IgG antibody titers produced by mice immunized singly with an attenuated WNV-poly(A) strain in different dosages; B: neutralizing antibody titers produced by mice immunized singly with the attenuated WNV-poly(A) strain in different dosages; C: survival statuses of mice immunized with singly with the attenuated WNV-poly(A) strain in different dosages after virus challenge; D: body weights of the mice immunized with singly with the attenuated WNV-poly(A) strain in different dosages after virus challenge; and E: blood toxicity statuses of the mice immunized with singly with the attenuated WNV-poly(A) strain in different dosages after virus challenge.

The results show that C57BL/6 mice immunized with different doses of attenuated WNV-poly(A) strains produce a strong antibody response after 14 days, and the IgG antibody titer and neutralizing antibody titer are increased at Day 28 after immunization. The mice immunized with different doses produce specific IgG antibody titers without significant dose-dependence, and IgG antibody titers are all around 1:12800 at Day 28 after immunization (FIG. 6A). Neutralizing antibody levels increase with increasing immunization dose, wherein the neutralizing antibody titer of mice immunized with $10^4$ PFU of attenuated WNV-poly(A) strain after 28 days is 1:40-1:80, and the antibody titer of mice immunized with $10^7$ PFU of attenuated WNV-poly(A) strain is 1:160-1:640 (B in FIG. 6). It is demonstrated that the attenuated WNV-poly(A) strain can produce a strong antibody response against WNV after immunizing the C57BL/6 mice.
2. Challenge Protection Effects of Attenuated WNV-Poly(A) Strain in C57BL/6 Mouse Model On Day 30 after immunization, except for the Mock group which is not subjected to any treatment, the remaining five groups of mice are subjected to intraperitoneal challenge with $10^7$ PFU of WT WNV The mice are recorded for the survival status daily and weighed, and the blood toxicity is determined in accordance with the method in Example 4 on Day 2 after challenge. The results show that the control group mice immunized with PBS begin to lose weight significantly on Day 5 after the challenge (D in FIG. 6), and high blood toxicity levels are detected on Day 2 after challenge (E in FIG. 6), showing symptoms such as hair frizzy, hindlimb paralysis, etc., and all died on Day 9 (C in FIG. 6). The mice that are immunized with the attenuated WNV-poly(A) strain all survive, which is similar to the mice in the Mock group without any treatment, so there are no any onset symptoms and any blood toxicity are detected. The above experiments prove that the attenuated WNV-poly(A) strain can provide good immune protection against C57BL/6 mice as an attenuated vaccine.

Figure 7:
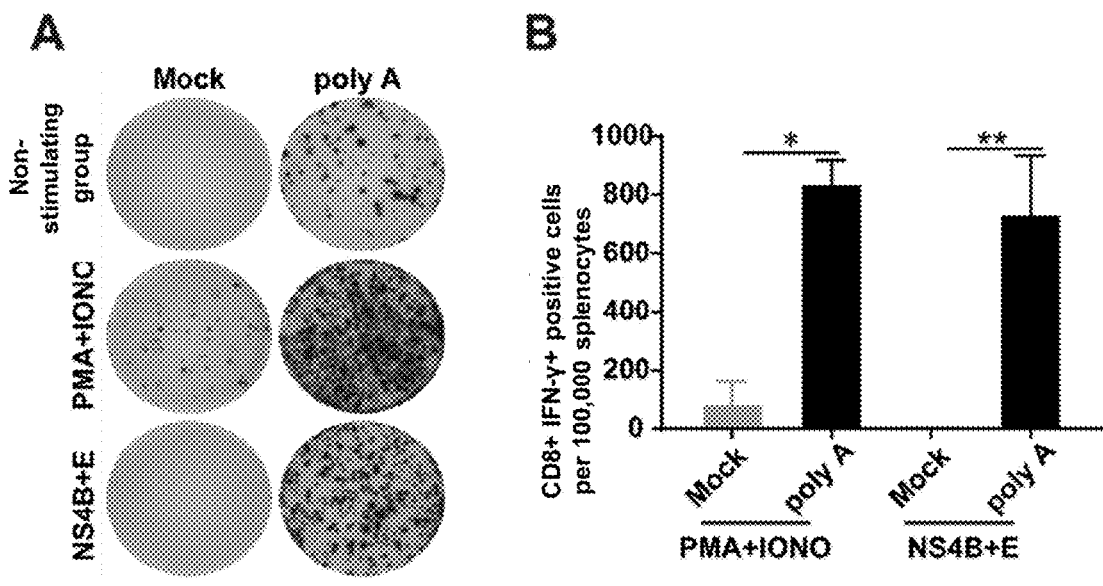
FIG. 7 shows a cellular immunity evaluation of an attenuated WNV-poly(A) strain on a C57BL/6 mouse model, wherein: A: a 7 d CD8$^+$ IFN-$\gamma^+$ T cell ELISpot detection map of a mouse immunized with singly with the attenuated WNV-poly(A) strain; and B: a 7 d CD8$^+$ IFN-$\gamma^+$ T cell percentage of the mouse immunized with singly with the attenuated WNV-poly(A) strain.

Example 7: CD8$^+$ T Cell Response of Attenuated West Nile Virus in Mouse Model This example investigates a CD8$^+$ T cell response of an attenuated WNV-poly (A) strain in a C57BL/6 mouse model, The CD8$^+$ T cell response plays an important role against a West Nile virus (WNV) infection. In order to detect whether the attenuated WNV-poly(A) strain can induce a CD8$^+$ T cell response after immunizing mice, two groups of 6- to 8-week-old female C57BL/6 mice (3 mice/group) are taken, wherein the mice in one group are intraperitoneally immunized with 10$^7$ PFU of attenuated WNV-poly(A) strain, while the mice in the other group are immunized with an equal volume of PBS as a control. The spleen of each mouse is harvested on Day 7 after immunization and subjected to in vitro stimulation with specific polypeptides (WNV E protein and NS4B protein), while the spleen of a mouse subjected to in vitro stimulation with non-specific stimulants (phorbol myristate acetate (PMA) and ionomycin (IONO)) is used as a positive control; and the proliferation of CD8$^+$ IFN-$\gamma^+$ T cells is detected by an ELISPOT method. The results are shown in FIG. 7. The CD8$^+$ IFN-$\gamma^+$ T cells of the mice immunized with the attenuated WNV-poly(A) strain show significant activation under the specific peptides and the non-specific stimulants, while the mice in the Mock group do not have any CD8$^+$ IFN-$\gamma^+$ T cell activation under specific peptide stimulation. The above results show that the attenuated WNV-poly(A) strain rescued by the present disclosure can produce a strong CD8$^+$ IFN-$\gamma^+$ T cell response against WNV E protein and NS4B epitope properties after immunizing with C57BL/6 mice.

Example 8: Long-Term Immune Protection Effects of Attenuated West Nile Virus in Mouse Model This example investigates the long-term immune protection effects of an attenuated WNV-poly(A) strain on C57BL/6.

Figure 8:
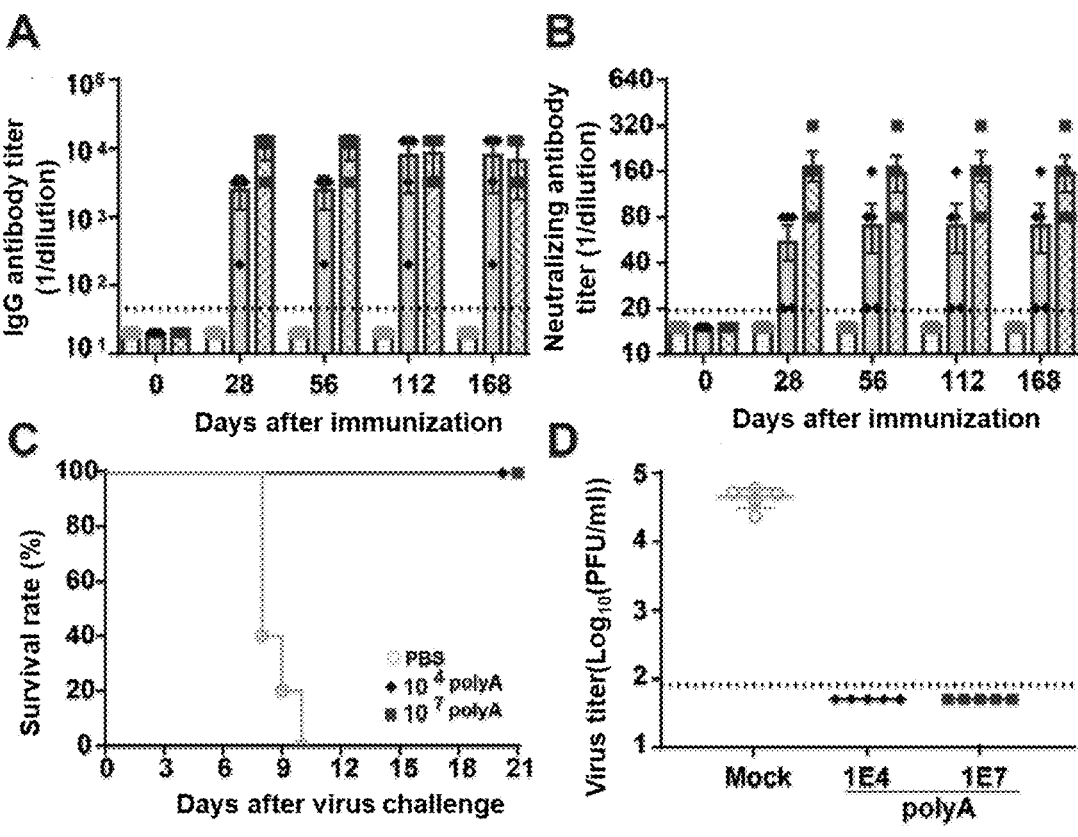
FIG. 8 shows a long-term immune protection experiment of an attenuated WNV-poly(A) strain on a C57BL/6 mouse model, wherein: A: a long-term maintained IgG antibody titer produced by a mouse immunized singly with the attenuated WNV-poly(A) strain; B: a long-term maintained neutralizing antibody production status produced by the mouse immunized singly with the attenuated WNV-poly(A) strain; C: a long-term survival status of the mouse immunized with singly with the attenuated WNV-poly(A) strain after virus challenge; and D: a long-term blood toxicity status of the mouse immunized with singly with the attenuated WNV-poly(A) strain after virus challenge.

Three groups of 4-week-old female C57BL/6 mice (5 mice/group) are taken and infected intraperitoneally with 10$^4$ PFU and 10$^7$ PFU of attenuated WNV-poly(A) strain respectively, and mice immunized with PBS are used as controls. After immunization, orbital blood is collected at Day 28, Day 56, Day 112 and Day 168, and specific IgG and neutralizing antibody titers are detected according to the method in Example 5. On Day 170 after immunization, the mice are infected intraperitoneally with 10$^7$ PFU of WN WNV for a challenge experiment, and on Day 2 after the challenge, the blood toxicity is determined according to the method in Example 4 and the survival rate of mice is determined. The results show that the specific IgG antibody and neutralizing antibody titers caused by mice immunized with 10$^4$ PFU and 10$^7$ PFU of attenuated WNV-poly(A) strain remain basically stable within 168 days (A and B in FIG. 8), the survival rate of the mice after challenge is 100%, and no blood toxicity is detected on Day 2 after challenge (C and D in FIG. 8). The above experiment proves that the attenuated WNV-poly(A) strain can provide long-term immune protection for the mice.

Example 9: Pathogenicity of Attenuated Dengue Virus

This example investigates the pathogenicity of attenuated dengue virus (DENV) strain DENV-poly(A) on AG129.

Five groups of 4-week-old female AG129/6 mice (5 mice/group) are taken and infected intraperitoneally with 10$^1$ PFU, 10$^4$ PFU or 10$^5$ PFU of attenuated DENV-poly(A) strain and 10$^4$ PFU of WT DENV, and mice injected with equal volume of PBS are used as controls. On Days 2, and 3 after infection, blood toxicity determination is performed by detecting the virus titers in the serum of mice. The specific method includes: collecting about 100 μl of blood from the orbit of each mouse and putting it in a 1.5 ml EP tube, standing at 4° C. for 3 h, then collecting the serum by centrifugation at 5000 rpm for 5 min for virus titer determination. The determination scheme is the same as the virus titer determination in Example 1. The mice are weighed for 27 consecutive days after simultaneous infection and the survival statuses of the mice are observed within 27 days.

Figures 9, 10:
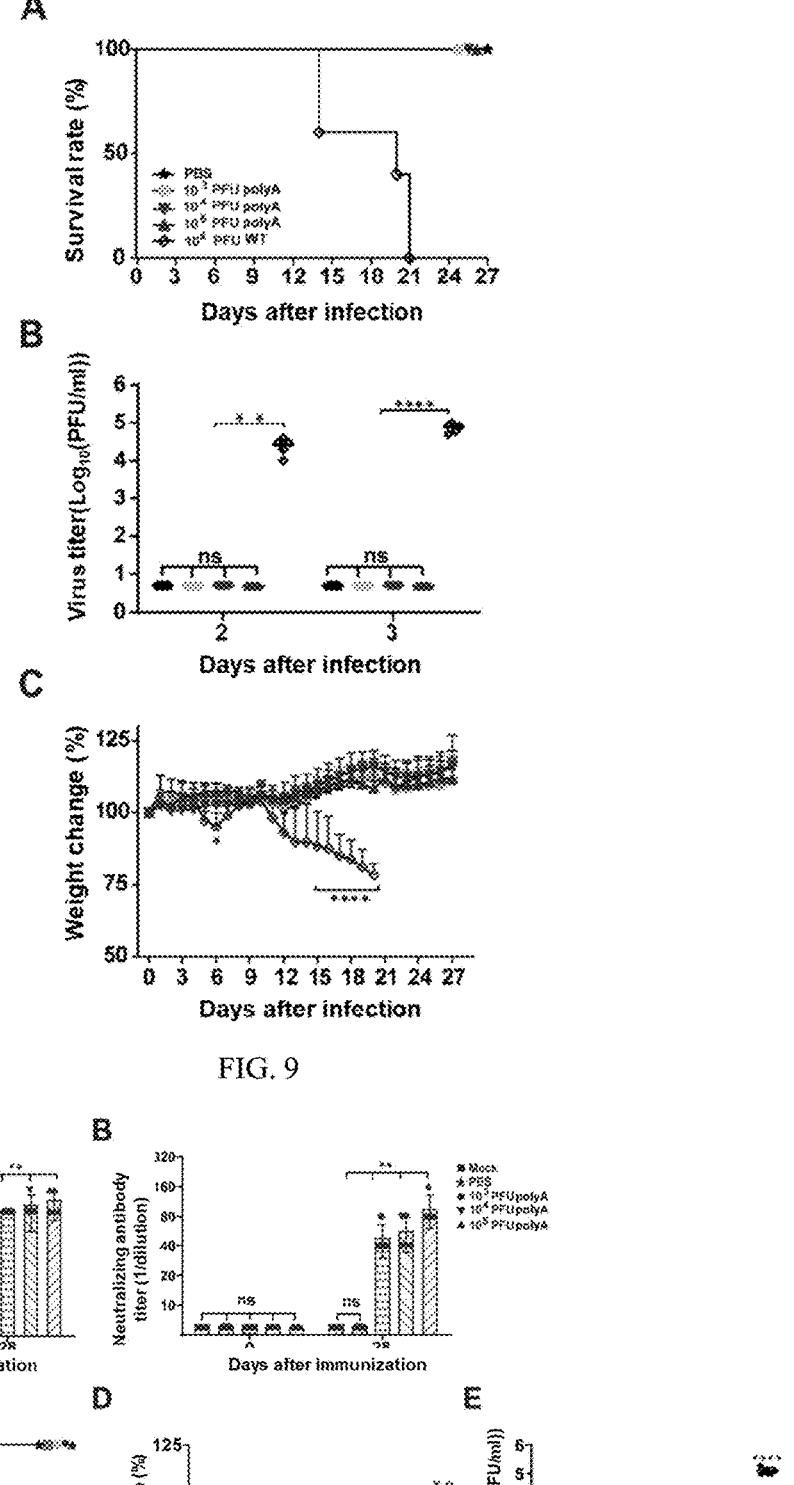
FIG. 9 shows pathogenicity detection of DENV-poly(A) on AG129, wherein: A: a survival rate of mice immunized with an attenuated DENV-poly(A) strain; B: blood toxicity statuses of the mice immunized with the attenuated DENV-poly(A) strain; and C: body weights of the mice immunized with the attenuated DENV-poly(A) strain.
FIG. 10 shows an immune protection experiment of DENV-poly(A) on an AG129/6 mouse model, wherein: A: IgG antibody titers produced by mice immunized singly with an attenuated DENV-poly(A) strain in different dosages; B: neutralizing antibody titers produced by the mice immunized singly with the attenuated DENV-poly(A) strain in different dosages; C: survival statuses of the mice immunized with singly with the attenuated DENV-poly(A) strain in different dosages after virus challenge; D: body weights of the mice immunized with singly with the attenuated DENV-poly(A) strain in different dosages after virus challenge; and E: blood toxicity statuses of the mice immunized with singly with the attenuated DENV-poly(A) strain in different dosages after virus challenge.

The results show that the mice inoculated with the attenuated DENV-poly(A) strain all survive (A in FIG. 9), and no viremia is detected in other doses (B in FIG. 9); and the changes in body weight are consistent with the changes in a PBS immune group (C in FIG. 9) and no other pathogenesis is observed. However, the mice inoculated with 10$^4$ PFU of WT DENV manifest hyper viremia (B in FIG. 9), with significant weight loss from Day 10 (C in FIG. 9), and all die on Day 21 (A in FIG. 9). It is shown that the attenuated DENV-poly(A) strain has sufficiently reduced virulence, does not cause a disease in the AG129 mice, has high safety, and can be used as a potential live attenuated vaccine.

Example 10: Humoral Immunity and Challenge Protection Effects of Attenuated Dengue Virus in Mouse Model This example investigates the humoral immunity and challenge protection effects of an attenuated DENV-poly(A) strain in a AG129 mouse model.
1. The Humoral Immunity of Attenuated DENV-Poly(A) Strain in AG129 Mouse Model
Five groups of 4-week-old female AG129 mice (5 mice/group) are taken and infected intraperitoneally with 10 PFU, 10$^4$ PFU or 10$^5$ PFU of attenuated P1-generation DENV-poly(A) strain obtained in Example 3, and mice in a Mock group which are immunized with equal volume of PBS and the mice in the Mock group which are not treated are used as controls. On Days 28 after immunization, blood is collected according to an orbital blood collection method in Example 4, and serum is collected by centrifugation after standing at 4° C. for 3 h, inactivated at 56° C. for 30 min, and frozen at −20° C. for later use.

IgG antibody titers are detected by ELISA and neutralizing antibody titers are detected by PRNT50, respectively:

1) Detection of IgG Antibody Titers by ELISA

A 96-well plate is coated with an attenuated DENV-poly (A) strain and blocked with 5% skim milk prepared from PBS; serum is subjected to 4-fold serial dilution from 1:50 and then incubated with the coated 96-well plate at 37° C. for 2 h; after the plate is washed with PBST for three times, an HRP sheep anti-mouse antibody is incubated at 37° C. for 1 h, and developed with a two-component chromogenic kit (Proteintech); after the addition of 1 M $H_2SO_4$ for termination, an absorbance value at 450 nm is detected with a multifunctional microplate reader; and the IgG antibody titer is the highest dilution when the serum absorbance value of immunized mice is 2 times the serum absorbance value of unimmunized mice.

2) Detection of Neutralizing Antibody Titers by PRNT50

$2\times10^5$ BHK-21 cells are inoculated in each well of a 12-well cell culture plate, respectively; when the cell confluency reaches 90%, the serum is first subjected to 2-fold serial dilution; 100 µl of diluted antibody and an equal volume of 100 PFU of WT-DENV are well mixed and incubated at 37° C. for 1 h; the medium in the wells is discarded, and the incubated serum-virus mixture is added to the corresponding wells, adsorbed at 37° C. for 1 h, and shaken well every 15 min; after adsorption, the virus solution in each well is discarded by suction, 1 mL of covering containing 2% methylcellulose is added, incubated in an 37° C., 5% $CO_2$ incubator for 72 h, stained with a staining solution containing 1% crystal violet and 3.7% formaldehyde after the formation of plaques, and treated at room temperature for 30 min; the staining solution is removed from the wells and the bottoms of the wells are rinsed with running water, and after drying, the virus titers after serum neutralization can be counted at each dilution; and the neutralizing antibody titer (PRNT50) in serum is the highest dilution of serum when the virus titer is neutralized by 50%.

The results show that AG129 mice immunized with different doses of attenuated DENV-poly(A) strains in single immunization produce a strong antibody response after 28 days. The IgG antibody titers are all around 1:3200-1:12800 (A in FIG. 10). Neutralizing antibody levels increase with increasing immunization dose, wherein the neutralizing antibody titer of mice immunized with 10 PFU of attenuated WNV-poly(A) strain after 28 days is 1:40-1:80, and the neutralizing antibody titer of mice immunized with $10^5$ PFU of attenuated WNV-poly(A) strain is 1:80-1:160 (B in FIG. 6). It is demonstrated that the attenuated DENV-poly(A) strain can produce a strong antibody response against DENV after immunizing the AG129 mice.

2. Challenge Protection Effects of Attenuated DENV-Poly (A) Strain in AG129 Mouse Model On Day 30 after immunization, except for the Mock group which is not subjected to any treatment, the remaining four groups of mice are subjected to intraperitoneal challenge with $10^6$ PFU of WT DENV. The mice is recorded for the survival daily and weighed, and the toxic blood is determined in accordance with the method in Example 4 on Day 3 after challenge. The results show that the control group mice immunized with PBS begin to lose weight significantly on Day 4 after the challenge (D in FIG. 10), and high blood toxicity levels are detected on Day 3 after challenge (E in FIG. 10), showing symptoms such as dorsal hair standing up, and all die on Day 16 (C in FIG. 10). The mice that are immunized with the attenuated DENV-poly(A) strain all survive, which is similar to the mice in the Mock group without any treatment, so no any onset symptoms and any blood toxicity are detected. The above experiment proves that the attenuated DENV-poly(A) strain can provide good immune protection against AG129 mice as an attenuated vaccine.

25

What is claimed is:

1. An attenuated flavivirus virus, comprising a polyadenylic acid (poly(A)) sequence, wherein the polyadenylic acid (poly(A)) sequence is used for replacing a part of nucleotide sequence of a 3' untranslated region (3'UTR) of the flavivirus virus, so that the 3' untranslated region (3'UTR) of the attenuated flavivirus virus obtained in response to the part of the nucleotide sequence of the flavivirus virus being replaced at least retains a 3'-end stem loop region (3'SL), the flavivirus virus is West Nile virus (WNV) or dengue virus (DENV).

2. The attenuated flavivirus virus according to claim 1, wherein the part of nucleotide sequence comprises all or a part of a nucleotide sequence of a 5'-end stem loop region (5'SL), all or a part of a nucleotide sequence of a cyclization sequence region (CS), and/or all or a part of a nucleotide sequence of a dumbbell region (DB) in a 3' untranslated region (3'UTR);

optionally, after the part of nucleotide sequence is replaced by the polyadenylic acid (poly(A)) sequence, the 3' untranslated region (3'UTR) of the attenuated flavivirus virus retains at least a cyclization sequence region 1 (CS1) and a short hairpin 3' stem loop region (sHP-3'SL) behind the cyclization sequence region 1 in the 3' untranslated region;

optionally, the 5'-end stem loop region (5'SL) in the 3' untranslated region (3'UTR) is selected from a stem loop region I (SLI), a stem loop region II (SLII), a stem loop region III (SLIII) and a stem loop region IV (SLIV);

optionally, the cyclization sequence region (CS) is selected from a cyclization sequence region 2 (CS2), a cyclization sequence region 3 (CS3), a repetitive cyclization sequence region 2 (RCS2) and a repetitive cyclization sequence region 3 (RCS3);

optionally, the dumbbell region (DB) is selected from a dumbbell region 1 (DB1) and a dumbbell region 2 (DB2).

3. The attenuated flavivirus virus according to claim 1, wherein the polyadenylic acid (poly(A)) sequence comprises 10-200 adenylates;

optionally, the polyadenylic acid (poly(A)) sequence comprises 50-180, 100-160 adenylates;

optionally, the polyadenylic acid (poly(A)) sequence comprises 130-150 adenylates, optionally, the polyadenylic acid (poly(Ab) sequence comprises 130 or 150 adenylates.

4. A DNA, which can be transcribed to produce an RNA genome of the attenuated flavivirus virus according to claim 1 optionally, the DNA is an infectious clone of an attenuated strain of the flavivirus virus;

optionally, the infectious clone is a plasmid.

5. A cell, comprising the attenuated flavivirus virus according to claim 1 or a DNA that can be transcribed to produce an RNA genome of the attenuated flavivirus virus.

6. A vaccine, comprising the attenuated flavivirus virus according to claim 1, a DNA that can be transcribed to produce an RNA genome of the attenuated flavivirus virus, and/or a cell comprising the attenuated flavivirus virus or the DNA.

7. A pharmaceutical composition, comprising the attenuated flavivirus virus according to claim 1, a DNA that can be transcribed to produce an RNA genome of the attenuated flavivirus virus, a cell comprising the attenuated flavivirus virus or the DNA and/or a vaccine comprising the attenuated flavivirus virus, the DNA, and/or the cell, and a pharmaceutically acceptable vector.

8. A method for preparing the attenuated flavivirus virus according to claim 1, the method comprising substituting a part of nucleotide sequence of a 3' untranslated region (3'UTR) of a wild-type virus with a polyadenylic acid (poly(A)) sequence, wherein optionally, the attenuated flavivirus virus is obtained by means of rescue on baby hamster kidney cells BHK-21 and/or amplification on African green monkey kidney Vero cells.

9. A method of stimulating an immune response to a flavivirus virus, comprising immunologically administering to the individual an effective mount of an attenuated flavivirus virus vaccine, wherein the attenuated flavivirus virus vaccine comprises: the attenuated flavivirus virus according to claim 1, a DNA that can be transcribed to produce an RNA genome of the attenuated flavivirus virus and a cell comprising the attenuated flavivirus virus or the DNA.

10. A method of treating or preventing diseases caused by flavivirus virus, comprising administering to an individual an effective mount of a medicament, wherein the medicament comprises: the attenuated flavivirus virus according to claim 1, a DNA that can be transcribed to produce an RNA genome of the attenuated flavivirus virus, a cell comprising the attenuated flavivirus virus or the DNA, a vaccine comprising the attenuated flavivirus virus, the DNA, and/or the cell and/or the pharmaceutical composition comprising the attenuated flavivirus virus, the DNA, the cell and/or the vaccine.

11. The attenuated flavivirus virus according to claim 1, the attenuated flavivirus virus has a plaque titer of $5\times10^4$–$5\times10^6$ PFU/ml.

12. The attenuated flavivirus virus according to claim 1, the attenuated flavivirus virus is 10-100 times less virulent than a parent wild-type virus.

13. The attenuated flavivirus virus according to claim 1, the attenuated flavivirus virus is obtained by means of rescue on baby hamster kidney cells BHK-21 and/or amplification on African green monkey kidney Vero cells.

14. The attenuated flavivirus virus according to claim 1, the dengue virus is selected from 1-type, 2-type, 3-type and 4-type dengue viruses.

15. The attenuated flavivirus virus according to claim 1, the attenuated West Nile virus comprises a nucleotide sequence having 80% or more identity with a nucleotide sequence shown in SEQ ID NO. 1;

optionally, the attenuated West Nile virus comprises a nucleotide sequence having more than 85% identity with the nucleotide sequence shown in SEQ ID NO. 1;

optionally, the attenuated West Nile virus comprises a nucleotide sequence having more than 90% identity with the nucleotide sequence shown in SEQ ID NO. 1;

optionally, the attenuated West Nile virus comprises a nucleotide sequence having more than 95% identity with the nucleotide sequence shown in SEQ ID NO. 1;

optionally, the attenuated West Nile virus comprises a nucleotide sequence having more than 96% identity with the nucleotide sequence shown in SEQ ID NO. 1;

optionally, the attenuated West Nile virus comprises a nucleotide sequence having more than 97% identity with the nucleotide sequence shown in SEQ ID NO. 1;

optionally, the attenuated West Nile virus comprises a nucleotide sequence having more than 98% identity with the nucleotide sequence shown in SEQ ID NO. 1;

optionally, the attenuated West Nile virus comprises a nucleotide sequence having more than 99% identity with the nucleotide sequence shown in SEQ ID NO. 1;

optionally, the nucleotide sequence of the attenuated West Nile virus is SEQ ID NO. 1.

16. The attenuated flavivirus virus according to claim 1, the attenuated dengue virus comprises a nucleotide sequence having 80% or more identity with a nucleotide sequence shown in SEQ ID NO. 3;

optionally, the attenuated dengue virus comprises a nucleotide sequence having more than 85% identity with the nucleotide sequence shown in SEQ ID NO. 3;

optionally, the attenuated dengue virus comprises a nucleotide sequence having more than 90% identity with the nucleotide sequence shown in SEQ ID NO. 3;

optionally, the attenuated dengue virus comprises a nucleotide sequence having more than 95% identity with the nucleotide sequence shown in SEQ ID NO. 3;

optionally, the attenuated dengue virus comprises a nucleotide sequence having more than 96% identity with the nucleotide sequence shown in SEQ ID NO. 3;

optionally, the attenuated dengue virus comprises a nucleotide sequence having more than 97% identity with the nucleotide sequence shown in SEQ ID NO. 3;

optionally, the attenuated dengue virus comprises a nucleotide sequence having more than 98% identity with the nucleotide sequence shown in SEQ ID NO. 3;

optionally, the attenuated dengue virus comprises a nucleotide sequence having more than 99% identity with the nucleotide sequence shown in SEQ ID NO. 3;

optionally, the nucleotide sequence of the attenuated dengue virus is SEQ ID NO. 3.

17. The attenuated flavivirus virus according to claim 1, the part of nucleotide sequence comprises a 5'-end stem loop region I (SLI), a stem loop region II (SLII), a repetitive cyclization sequence region 3 (RCS3), a stem loop region III (SLIII), a stem loop region IV (SLIV), a cyclization sequence region 3 (CS3), a dumbbell region 1 (DB1), a repetitive cyclization sequence region 2 (RCS2), a dumbbell region 2 (DB2), and a cyclization sequence region 2 (CS2), and after the part of nucleotide sequence is replaced by the polyadenylic acid (poly(A)) sequence, the 3' untranslated region (3'UTR) of the attenuated flavivirus virus retains a cyclization sequence region 1 (CS1) and a short hairpin 3' stem loop region (sHP-3'SL) behind the cyclization sequence region 1 in the 3' untranslated region.

18. The attenuated flavivirus virus according to claim 1, the part of nucleotide sequence comprises a 5'-end stem loop region II (SLII), a repetitive cyclization sequence region 3 (RCS3), a stem loop region IV (SLIV), a cyclization sequence region 3 (CS3), a dumbbell region 1 (DB1), a repetitive cyclization sequence region 2 (RCS2), a dumbbell region 2 (DB2), and a cyclization sequence region 2 (CS2), and after the part of nucleotide sequence is replaced by the polyadenylic acid (poly(A)) sequence, the 3' untranslated region (3'UTR) of the attenuated flavivirus virus retains a cyclization sequence region 1 (CS1) and a short hairpin 3' stem loop region (sHP-3'SL) behind the cyclization sequence region 1 in the 3' untranslated region.

19. The method according to claim 9, the attenuated flavivirus virus vaccine is an attenuated West Nile virus vaccine;

optionally, the attenuated flavivirus virus vaccine is an attenuated dengue virus vaccine.

20. The method according to claim 10, the method is used for treating or preventing diseases caused by the West Nile virus;

optionally, the method is used for treating or preventing diseases caused by the dengue virus.

\* \* \* \* \*

SEQUENCE LISTING

```
<160> NUMBER OF SEQ ID NOS: 6

<210> SEQ ID NO 1
<211> LENGTH: 10642
<212> TYPE: DNA
<213> ORGANISM: West Nile virus

<400> SEQUENCE: 1
agtagttcgc ctgtgtgagc tgacaaactt agtagtgttt gtgaggatta acaacaatta      60
acacagtgcg agctgtttct tagcacgaag atctcgatgt ctaagaaacc aggagggccc     120
ggcaagagcc gggctgtcaa tatgctaaaa cgcggaatgc cccgcgtgtt gtccttgatt     180
ggactgaaga gggctatgtt gagcctgatc gacggcaagg ggccaatacg atttgtgttg     240
gctctcttgg cgttcttcag gttcacagca attgctccga cccgagcagt gctggatcga     300
tggagaggtg tgaacaaaca aacagcgatg aaacaccttc tgagttttaa gaaggaacta     360
gggaccttga ccagtgctat caatcggcgg agctcaaaac aaaagaaaag aggaggaaag     420
accggaattg cagtcatgat tggcctgatc gccagcgtag gagcagttac cctctctaac     480
ttccaaggga aggtgatgat gacggtaaat gctactgacg tcacagatgt catcacgatt     540
ccaacagctg ctggaaagaa cctatgcatt gtcagagcaa tggatgtggg atacatgtgc     600
gatgatacta tcacttatga atgcccagtg ctgtcggctg gtaatgatcc agaagacatc     660
gactgttggt gcacaaagtc agcagtctac gtcaggtatg gaagatgcac caagacacgc     720
```

-continued

```
cactcaagac gcagtcggag gtcactgaca gtgcagacac acggagaaag cactctagcg   780
aacaagaagg gggcttggat ggacagcacc aaggccacaa ggtatttggt aaaaacagaa   840
tcatggatct tgaggaaccc tggatatgcc ctggtggcag ccgtcattgg ttggatgctt   900
gggagcaaca ccatgcagag agttgtgttt gtcgtgctat tgcttttggt ggccccagct   960
tacagcttca actgccttgg aatgagcaac agagacttct tggaaggagt gtctggagca  1020
acatgggtgg atttggttct cgaaggcgac agctgcgtga ctatcatgtc taaggacaag  1080
cctaccatcg atgtgaagat gatgaatatg gaggcggcca acctggcaga ggtccgcagt  1140
tattgctatt tggctaccgt cagcgatctc tccaccaaag ctgcgtgccc gaccatggga  1200
gaagctcaca atgacaaacg tgctgaccca gcttttgtgt gcagacaagg agtggtggac  1260
aggggctggg gcaacggctg cggactattt ggcaaaggaa gcattgacac atgcgccaaa  1320
tttgcctgct ctaccaaggc aataggaaga accatcttga aagagaatat caagtacgaa  1380
gtggccattt ttgtccatgg accaactact gtggagtcgc acggaaacta ctccacacag  1440
gttggagcca ctcaggcagg gagattcagc atcactcctg cggcgccttc atacacacta  1500
aagcttggag aatatggaga ggtgacagtg gactgtgaac cacggtcagg gattgacacc  1560
aatgcatact acgtgatgac tgttggaaca aagacgttct tggtccatcg tgagtggttc  1620
atggacctca acctcccttg gagcagtgct ggaagtactg tgtggaggaa cagagagacg  1680
ttaatggagt ttgaggaacc acacgccacg aagcagtctg tgatagcatt gggctcacaa  1740
gagggagctc tgcatcaagc tttggctgga gccattcctg tggaattttc aagcaacact  1800
gtcaagttga cgtcgggtca tttgaagtgt agagtgaaga tggaaaaatt gcagttgaag  1860
ggaacaacct atggcgtctg ttcaaaggct ttcaagtttc ttgggactcc cgcagacaca  1920
ggtcacggca ctgtggtgtt ggaattgcag tacactggca cggatggacc ttgtaaagtt  1980
cctatctcgt cagtggcttc attgaacgac ctaacgccag tgggcagatt ggtcactgtc  2040
aacccttttg tttcagtggc cacggccaac gctaaggtcc tgattgaatt ggaaccaccc  2100
tttggagact catacatagt ggtgggcaga ggagaacaac agatcaatca ccattggcac  2160
aagtctggaa gcagcattgg caaagccttt acaaccaccc tcaaaggagc gcagagacta  2220
gccgctctag agacacagc ttgggacttt ggatcagttg gaggggtgtt cacctcagtt  2280
gggaaggctg tccatcaagt gttcggagga gcattccgct tactgttcgg aggcatgtcc  2340
tggataacgc aaggattgct gggggctctc ctgttgtgga tgggcatcaa tgctcgtgat  2400
aggtccatag ctctcacgtt tctcgcagtt ggaggagttc tgctcttcct ctccgtgaac  2460
gtgcacgctg acactgggtg tgccatagac atcagccggc aagagctgag atgtggaagt  2520
ggagtgttca tacacaatga tgtggaggct tggatggacc gatacaagta ttaccctgaa  2580
acgccacaag gcctagccaa gatcattcag aaagctcata aggaaggagt gtgcggtcta  2640
cgatcagttt ccagactgga gcatcaaatg tgggaagcag tgaaggacga gctgaacact  2700
cttttgaagg agaatggtgt ggaccttagt gtcgtggttg agaaacagga gggaatgtac  2760
aagtcagcac ctaaacgcct caccgccacc acggaaaaat tggaaattgg ctggaaggcc  2820
tggggaaaga gtatttttat tgcaccagaa ctcgccaaca acacctttgt ggttgatggt  2880
ccggagacca aggaatgtcc gactcagaat cgcgcttgga atagcttaga agtggaggat  2940
tttggatttg gtctcaccag cactcggatg ttcctgaagg tcagagagag caacacaact  3000
gaatgtgact cgaagatcat tggaacggct gtcaagaaca acttggcgat ccacagtgac  3060
ctgtcctatt ggattgaaag caggctcaat gatacgtgga agcttgaaag ggcagttctg  3120
```

-continued

```
ggtgaagtca aatcatgtac gtggcctgag acgcatacct tgtgggcga tggaatcctt    3180 gagagtgact tgataatacc agtcacactg gcgggaccac gaagcaatca caatcggaga    3240
cctgggtaca agacacaaaa ccagggccca tgggacgaag gccgggtaga gattgacttc    3300
gattactgcc caggaactac ggtcaccctg agtgagagct cgggacaccg tggacctgcc    3360
actcgcacca ccacagagag cggaaagttg ataacagatt ggtgctgcag gagctgcacc    3420
ttaccaccac tgcgctacca aactgacagc ggctgttggt atggtatgga gatcagacca    3480
cagagacatg atgaaaagac cctcgtgcag tcacaagtga atgcttataa tgctgatatg    3540 attgacccctt ttcagttggg ccttctggtc gtgttcttgg ccacccagga ggtccttcgc    3600
aagaggtgga cagccaagat cagcatgcca gctatactga ttgctctgct agtcctggtg    3660
tttgggggca ttacttacac tgatgtgtta cgctatgtca tcttggtggg ggcagctttc    3720
gcagaatcta attcgggagg agacgtggta cacttggcgc tcatggcgac cttcaagata    3780
caaccagtgt ttatggtggc atcgtttctc aaagcgagat ggaccaacca ggagaacatc    3840
ttgttgatgt tggcggctgt tttctttcaa atggcttatc acgatgcccg ccaaattctg    3900
ctctgggaga tccctgatgt gttgaattca ctggcggtag cttggatgat actgagagcc    3960
ataacattca caacgacatc aaacgtggtt gttccgctgc tagccctgct aacacccggg    4020
ctgagatgct tgaatctgga tgtgtacagg atactgctgt tgatggtcgg aataggcagc    4080
ttgatcaggg agaagaggag tgcagctgca aaaaagaaag gagcaagtct gctatgcttg    4140
gctctagcct caacaggact tttcaacccc atgatccttg ctgctggact gattacatgt    4200
gatcccaacc gtaaacgcgg atggcccgca actgaagtga tgacagctgt cggcctgatg    4260
tttgccatcg tcggagggct ggcagagctt gacattgact ccatggccat tccaatgact    4320
atcgcggggc tcatgtttgc tgctttcgtg atttctggga aatcaacaga tatgtggatt    4380
gagagaacgg cggacatttc ctgggaaagt gatgcagaaa ttacaggctc gagcgaaaga    4440
gttgatgtgc ggcttgatga tgatggaaac ttccagctca tgaatgatcc aggagcacct    4500
tggaagatat ggatgctcag aatggtctgt ctcgcgatta gtgcgtacac cccctgggca    4560
atcttgccct cagtagttgg attttggata actctccaat acacaaagag aggaggcgtg    4620
ttgtgggaca ctccctcacc aaaggagtac aaaaaggggg acacgaccac cggcgtctac    4680
aggatcatga ctcgtgggct gctcggcagt tatcaagcag gagcgggcgt gatggttgaa    4740
ggtgttttcc acaccctttg gcatacaaca aaaggagccg ctttgatgag cggagagggc    4800
cgcctggacc catactgggg cagtgtcaag gaggatcgac tttgttacgg aggaccctgg    4860
aaattgcagc acaagtggaa cgggcaggat gaggtgcaga tgattgtggt ggaacctggc    4920
aagaacgtta agaacgtcca gacgaaacca ggggtgttca aaacacctga aggagaaatc    4980
ggggccgtga ctttggactt ccccactgga acatcaggct caccaatagt ggacaaaaac    5040
ggtgatgtga ttgggcttta tggcaatgga gtcataatgc ccaacggctc atacataagc    5100
gcgatagtgc agggtgaaag gatggatgag ccaatcccag ccggattcga acctgagatg    5160
ctgaggaaaa aacagatcac tgtactggat ctccatcccg gcgccggtaa aacaaggagg    5220
attctgccac agatcatcaa agaggccata aacagaagac tgagaacagc cgtgctagca    5280
ccaaccaggg ttgtggctgc tgagatggct gaagcactga gaggactgcc catccggtac    5340
cagacatccg cagtgcccag agaacataat ggaaatgaga ttgttgatgt catgtgtcat    5400 gctacccctca cccacaggct gatgtctcct cacagggtgc cgaactacaa cctgttcgtg    5460
```

```
atggatgagg ctcatttcac cgacccagct agcattgcag caagaggtta catttccaca   5520
aaggtcgagc taggggaggc ggcggcaata ttcatgacag ccacccacc aggcacttca     5580 gatccattcc cagagtccaa ttcaccaatt tccgacttac agactgagat cccggatcga     5640
gcttggaact ctggatacga atggatcaca gaatacaccg ggaagacggt ttggtttgtg     5700
cctagtgtca agatggggaa tgagattgcc cttttgcctac aacgtgctgg aaagaaagta    5760
gtccaattga acagaaagtc gtacgagacg gagtacccaa aatgtaagaa cgatgattgg     5820
gactttgtta tcacaacaga catatctgaa atgggggcta actttaaggc gagcagggtg     5880
attgacagcc ggaagagtgt gaaaccaacc atcataacag aaggagaagg gagagtgatc      5940
ctgggagaac catctgcagt gacagcagct agtgccgccc agagacgtgg acgtatcggt     6000
agaaatccgt cgcaagttgg tgatgagtac tgttatgggg ggcacacgaa tgaagacgac     6060
tcgaacttcg cccattggac tgaggcacga atcatgctgg acaacatcaa catgccaaac     6120
ggactgatcg ctcaattcta ccaaccagag cgtgagaagg tatataccat ggatggggaa     6180
taccggctca gaggagaaga gagaaaaaac tttctggaac tgttgaggac tgcagatctg     6240
ccagtttggc tggcttacaa ggttgcagcg gctggagtgt cataccacga ccggaggtgg     6300
tgctttgatg gtcctaggac aaaacacaat ttagaagaca caacgaagt ggaagtcatc      6360 acgaagcttg gtgaaaggaa gattctgagg ccgcgctgga ttgacgccag ggtgtactcg     6420
gatcaccagc cactaaaggc gttcaaggac ttcgcctcgg gaaaacgttc tcagataggg     6480
ctcattgagg ttctgggaaa gatgcctgag cacttcatgg ggaagacatg ggaagcactt      6540
gacaccatgt acgttgtggc cactgcagag aaaggaggaa gagctcacag aatggccctg     6600
gaggaactgc cagatgctct tcagacaatt gccttgattg ccttattgag tgtgatgacc     6660
atgggagtat tcttcctcct catgcagcgg aagggcattg gaaagatagg tttgggaggc     6720
gctgtcttgg gagtcgcgac ctttttctgt tggatggctg aagttccagg aacgaagatc     6780 gccgaatgt tgctgctctc ccttctcttg atgattgtgc taattcctga gccagagaag       6840
caacgttcgc agacagacaa ccagctagcc gtgttcctga tttgtgtcat gacccttgtg     6900
agcgcagtgc cagccaacga gatgggttgg ctagataaga ccaagagtga cataagcagt     6960
ttgtttgggc aaagaattga ggtcaaggag aatttcagca tgggagagtt tcttttggac     7020
ttgaggccgg caacagcctg gtcactgtac gctgtgacaa cagcggtcct cactccactg     7080
ctaaagcatt tgatcacgtc agattacatc aacacctcat tgacctcaat aaacgttcag     7140
gcaagtgcac tattcacact cgcgcgaggc ttccccttcg tcgatgttgg agtgtcggct     7200
ctcctgctag cagccggatg ctgggggacaa gtcaccctca ccgttacggt aacagcggca     7260
acactccttt tttgccacta tgcctacatg gttcccggtt ggcaagctga ggcaatgcgc     7320
tcagcccagc ggcggacagc ggccggaatc atgaagaacg ctgtagtgga tggcatcgtg     7380 gccacgacg tcccagaatt agagcgcacc acacccatca tgcagaagaa agttggacag      7440
atcatgctga tcttggtgtc tctagctgca gtagtagtga acccgtctgt gaagacagta     7500
cgagaagccg gaattttgat cacggccgca gcggtgacgc tttgggagaa tggagcaagc     7560
tctgtttgga acgcaacaac tgccatcgga ctctgccaca tcatgcgtgg gggttggttg     7620
tcatgtctat ccataacatg gacactcata aagaacatgg aaaaaccagg actaaaaaga     7680
ggtggggcaa aaggacgcac cttgggagag gtttggaaag aaagactcaa ccagatgaca     7740
aaagaagagt tcactaggta ccgcaaagag gccatcatcg aagtcgatcg ctcagcagca     7800
aaacacgcca ggaaagaagg caatgccact ggagggcatc cagtctctag gggcacagca     7860
```

-continued

```
aaactgagat ggctggtcga acggaggttt ctcgaaccgg tcggaaaagt gattgacctt    7920
ggatgtggaa gaggcggttg gtgttactat atggcaaccc aaaaaagagt ccaagaagtc    7980
agagggtaca caaagggcgg tcccggacat gaagagcccc aactagtgca aagttatgga    8040
tggaacattg tcaccatgaa gagtggagtg gatgtgttct acagaccttc tgagtgttgt    8100
gacaccctcc tttgtgacat cggagagtcc tcgtcaagtg ctgaggttga agagcatagg    8160
acgattcggg tccttgaaat ggttgaggac tggctgcacc gagggccaag ggaattttgc    8220
gtgaaggtgc tctgccccta catgccgaaa gtcatagaga agatggagct gctccaacgc    8280
cggtatgggg ggggactggt cagaaaccca ctctcacgga attccacgca cgagatgtat    8340
tgggtgagtc gagcttcagg caatgtggta cattcagtga atatgaccag ccaggtgctc    8400
ctaggaagaa tggaaaaaag gacctggaag ggaccccaat acgaggaaga tgtaaacttg    8460
ggaagtggaa ccagggcggt gggaaaaccc ctgctcaact cagacaccag taaaatcaag    8520
aacaggattg aacgactcag gcgtgagtac agttcgacgt ggcaccacga tgagaaccac    8580
ccatatagaa cctggaacta tcacggcagt tatgatgtga agcccacagg ctccgccagt    8640
tcgctggtca atggagtggt caggctcctc tcaaaaccat gggacaccat cacgaatgtt    8700
accaccatgg ccatgactga cactactccc ttcgggcagc agcgagtgtt caaagagaag    8760
gtggacacga aagctcctga accgccagaa ggagtgaagt acgtgctcaa cgagaccacc    8820
aactggttgt gggcgttttt ggccagagaa aaacgtccaa ggatgtgctc tcgagaggag    8880
ttcataagaa aggtcaacag caatgcagct ttgggtgcca tgtttgaaga gcagaatcaa    8940
tggaggagcg ccagagaggc agttgaagat ccaaaatttt gggagatggt ggatgaggag    9000
cgcgaggcac atctgcgggg ggaatgtcac acttgcattt acaacatgat gggaaagaga    9060
gagaaaaaac ccggagagtt cggaaaggcc aagggaagca gagccatttg gttcatgtgg    9120
cttggagctc gctttctgga gttcgaggct ctgggttttc tcaatgaaga ccactggctt    9180
ggaagaaaga actcaggagg aggtgtcgag ggcttgggcc tccaaaaact gggttacatc    9240
ctgcgtgaag ttggcacccg gcctgggggc aagatctatg ctgatgacac agctggctgg    9300
gacacccgca tcacgagagc tgacttggaa aatgaagcta aggtgcttga gctgcttgat    9360
ggggaacatc ggcgtcttgc cagggccatc attgagctca cctatcgtca caagttgtg    9420 aaagtgatgc gcccggctgc tgatggaaga accgtcatgg atgttatctc cagagaagat    9480
cagaggggga gtggacaagt tgtcacctac gccctaaaca ctttcaccaa cctggccgtc    9540
cagctggtga ggatgatgga aggggaagga gtgattggcc cagatgatgt ggagaaactc    9600
acaaaaggga aaggacccaa agtcaggacc tggctgtttg agaatgggga agaaagactc    9660
agccgcatgc tgtcagtggg agatgactgt gtggtaaagc ccctggacga tcgctttgcc    9720
acctcgctcc acttcctcaa tgctatgtca aaggttcgca agacatccag agtggaaa     9780 ccgtcaactg gatggtatga ttggcagcag gttccatttt gctcaaacca tttcactgaa    9840
ttgatcatga agatggaag aacactggtg gttccatgcc gaggacagga tgaattggta    9900
ggcagagctc gcatatctcc aggggccgga tggaacgtcc gcgacactgc ttgtctggct    9960
aagtcttatg cccagatgtg gctgcttctg tacttccaca agagagacct gcggctcatg    10020
gccaacgcca tttgctccgc tgtccctgtg aattgggtcc ctaccggaag aaccacgtgg    10080
tccatccatg caggaggaga gtggatgaca acagaggaca tgttggaggt ctggaaccgt    10140
gtttggatag aggagaatga atggatggaa gacaaaaccc cagtggagaa atggagtgac    10200
```

```
gtcccatatt caggaaaacg agaggacatc tggtgtggca gcctgattgg cacaagagcc    10260
cgagccacgt gggcagaaaa catccaggtg gctatcaacc aagtcagagc aatcatcgga    10320
gatgagaagt atgtggatta catgagttca ctaaagagat atgaagacac aactttggtt    10380
gaggacacag tactgtagat atttaaaaaa aaaaaaaaaa aaaaaaaaaa aaaaaaaaaa    10440
aaaaaaaaaa aaaaaaaaaa aaaaaaaaaa aaaaaaaaaa aaaaaaaaaa aaaaaaaaaa    10500
aaaaaaaaaa aaaaaaaaaa aaaaaaaaaa aaaacagcat attgacacct gggatagact    10560
aggagatctt ctgctctgca caaccagcca cacggcacag tgcgccgaca atggtggctg    10620
gtggtgcgag aacacaggat ct                                            10642
```

<210> SEQ ID NO 2
<211> LENGTH: 10663
<212> TYPE: DNA
<213> ORGANISM: Japanese encephalitis virus

<400> SEQUENCE: 2

```
agaagtttat ctgtgtgaac ttcttggctt agtatcgttg agaagaatcg agagattagt      60
gcagtttaaa cagttttttta gaacggaaga taaccatgac taaaaaacca ggagggcccg     120
gtaaaaaccg ggctatcaat atgctgaaac gcggcctacc ccgcgtattc ccactagtgg     180
gagtgaagag ggtagtaatg agcttgttgg acggcagagg gccagtacgt ttcgtgctgg     240
ctcttatcac gttcttcaag tttacagcat tagccccgac caaggcgctt ttaggccgat     300
ggaaagcagt ggaaaagagt gtggcaatga aacatcttac tagtttcaaa cgagaacttg     360
gaacactcat tgacgccgtg aacaagcggg gcagaaagca aaacaaaaga ggaggaaatg     420
aaggctcaat catgtggctc gcgagcttgg cagttgtcat agcttgtgca ggagccatga     480
agttgtcgaa tttccagggg aagcttttga tgaccatcaa caacacggac attgcagacg     540
ttatcgtgat tcccacctca aaaggagaga acagatgctg ggtccgggca atcgacgtcg     600
gctacatgtg tgaggacact atcacgtacg aatgtcctaa gcttaccatg ggcaatgatc     660
cagaggatgt ggattgctgg tgtgacaacc aagaagtcta cgtccaatat ggacggtgca     720
cgcggaccag gcattccaag cgaagcagga gatccgtgtc ggtccaaaca catgggggaga    780 gttcactagt gaataaaaaa gaggcttggc tggattcaac gaaagccaca cgatatctca     840
tgaaaactga gaactggatc ataaggaatc ctggctatgc tttcctggcg gcggtacttg     900
gctggatgct tggcagtaac aacggtcaac gcgtggtatt taccatcctc ctgctgttgg     960
tcgctccggc ttacagtttt aattgtctgg gaatgggcaa tcgcgacttc atagaaggag    1020
ccagtggagc cacttgggtg gacttggtgc tggaaggaga tagctgcttg acaatcatgg    1080
caaacgacaa accaacattg gacgtccgca tgattaacat cgaagctagc caacttgctg    1140
aggtcagaag ttactgctat catgcttcag tcactgacat ctcgacggtg gctcggtgcc    1200
ccacgactgg agaagcccac aacgagaagc gagctgatag tagctatgtg tgcaaacaag    1260
gcttcactga ccgtgggtgg ggcaacggat gtggactttt cgggaaggga agcattgaca    1320
catgtgcaaa attctcctgc accagtaaag cgattgggag aacaatccag ccagaaaaca    1380
tcaaatacga agttggcatt tttgtgcatg gaaccaccac ttcggaaaac catgggaatt    1440
attcagcgca agttggggcg tcccaggcgg caaagtttac agtaacaccc aatgctcctt    1500
cgataaccct caaacttggt gactacggag aagtcacact ggactgtgag ccaaggagtg    1560
gactgaacac tgaagcgttt tacgtcatga ccgtgggggtc aaagtcattt ctggtccata    1620
gggagtggtt tcatgacctc gctctcccct ggacgtcccc ttcgagcaca gcgtggagaa    1680
```

-continued

```
acagagaact cctcatggaa tttgaagagg cgcacgccac aaaacagtcc gttgttgctc      1740
ttgggtcaca ggaaggaggc ctccatcagg cgttggcagg agccatcgtg gtggagtact      1800
caagctcagt gaagttaaca tcaggccacc tgaaatgtag gctgaaaatg gacaaactgg      1860
ctctgaaagg cacaacctat ggcatgtgta cagaaaaatt ctcgttcgcg aaaaatccgg      1920
cggacactgg tcacggaaca gttgtcattg aactctccta ctctgggagt gatggcccct      1980
gcaaaattcc gattgtttcc gttgcgagcc tcaatgacat gacccccgtt gggcggctgg      2040
tgacagtgaa ccccttcgtc gcgacttcca gtgccaactc aaaggtgctg gtcgagatgg      2100
aacccccctt cggagactcc tacatcgtag ttggaagggg agacaagcag atcaaccacc      2160
attggcacaa agctggaagc acgctgggca aggccttttc aacaactttg aagggagctc      2220
aaagactggc agcgttgggc gacacagcct gggactttgg ctctattgga ggggtcttca      2280
actccatagg aaaagccgtt caccaagtgt ttggtggtgc cttcagaaca ctctttgggg      2340
gaatgtcttg gatcacacaa gggctaatgg gtgccctact gctctggatg ggcgtcaacg      2400
cacgagaccg atcaattgct ttggccttct tagccacagg gggtgtgctc gtgttcttag      2460
cgaccaatgt gcatgctgac actggatgtg ccattgacat cacaagaaaa gagatgagat      2520
gtggaagtgg catcttcgtg cacaacgacg tggaagcctg ggtggatagg tataaatatt      2580
tgccagaaac gcccagatcc ctagcgaaga tcgtccacaa agcgcacaag gaaggcgtgt      2640
gcggagtcag atctgtcact agactggagc accaaatgtg ggaagccgta agggacgaat      2700
tgaacgtcct gctcaaagag aatgcagtgg acctcagtgt ggttgtgaac aagcccgtgg      2760
gaagatatcg ctcagcccct aaacgcctat ccatgacgca agagaagttt gaaatgggct      2820
ggaaagcatg gggaaaaagc atcctctttg ccccggaatt ggctaactcc acatttgtcg      2880
tagatggacc tgagacaaag gaatgccctg atgagcacag agcttggaac agcatgcaaa      2940
tcgaagactt cggctttggc atcacatcaa cccgtgtgtg gctgaaaatt agagaggaga      3000
gcactgacga gtgtgatgga gcgatcatag gcacggctgt caaaggacat gtggcagtcc      3060
atagtgactt gtcgtactgg attgagagtc gctacaacga cacatggaaa cttgagaggg      3120
cagtctttgg agaggtcaaa tcttgcactt ggccagagac acacacccctt tggggagatg      3180 atgttgagga aagtgaactc atcattccgc acaccatagc cggaccaaaa agcaagcaca      3240
atcggaggga agggtataag acacaaaacc agggaccttg ggatgagaat ggcatagtct      3300
tggactttga ttattgccca gggacaaaag tcaccattac agaggattgt agcaagagag      3360
gcccttcggt cagaaccact actgacagtg gaaagttgat cactgactgg tgctgtcgca      3420
gttgctccct tccgccccta cgattccgga cagaaaatgg ctgctggtac ggaatggaaa      3480
tcagacctgt taggcatgat gaaacaacac tcgtcagatc acaggttgat gctttcaatg      3540
gtgaaatggt tgaccctttt cagctgggcc ttctggtgat gtttctggcc acccaggagg      3600
tccttcgcaa gaggtggacg gccagattga ccattcctgc ggttttgggg ccctacttg       3660 tgctgatgct tggggggcatc acttacactg atttggcgag gtatgtggtg ctagtcgctg      3720
ctgctttcgc agaggccaac agtggaggag acgtcctgca ccttgctttg attgccgttt      3780
ttaagatcca accagcattt ctagtgatga acatgcttag cacgagatgg acgaaccaag      3840
aaaacgtggt tctggtccta ggggctgcct tttcccaatt ggcctcagta gatctgcaaa      3900
taggagtcca cggaatcctg aatgccgccg ctatagcatg gatgattgtc cgagcgatca      3960
ccttccccac aacctcctcc gtcaccatgc cagtcttagc gcttctaact ccgggggatga      4020
```

-continued

```
gggctctata cctagacact tacagaatca tcctcctcgt catagggatt tgctccctgc   4080
tgcacgagag gaaaaagacc atggcaaaaa agaaaggagc tgtactcttg ggcttagcgc   4140
tcacatccac tggatggttc tcgcccacca ctatagctgc cggactaatg gtctgcaacc   4200
caaacaagaa gagagggtgg ccagctactg agtttttgtc ggcagttgga ttgatgtttg   4260
ccatcgtagg tggtttggcc gagttggata ttgaatccat gtcaataccc ttcatgctgg   4320
caggtctcat ggcagtgtcc tacgtggtgt caggaaaagc aacagatatg tggcttgaac   4380
gggccgccga catcagctgg gagatggatg ctgcaatcac aggaagcagt cggaggctgg   4440
atgtgaaact ggatgatgac ggagattttc acttgattga tgatcccggt gttccatgga   4500
aggtctgggt cctgcgcatg tcttgcattg gcttagccgc cctcacgcct tgggccatcg   4560
ttcccgccgc tttcggttat tggctcactt taaaaacaac aaaaagaggg ggcgtgtttt   4620
gggacacgcc atccccaaaa ccttgctcaa aaggagacac cactacagga gtctaccgaa   4680
ttatggctag agggattctt ggcacttacc aggccggcgt cggagtcatg tacgagaatg   4740
ttttccacac actatggcac acaactagag gagcagccat tatgagtgga gaaggaaaat   4800
tgacgccata ctggggtagt gtgagagaag accgcatagc ttacggaggc ccatggaggt   4860
ttgaccgaaa atggaatgga acagatgacg tgcaagtgat cgtggtagaa ccggggaagg   4920
ctgcagtaaa catccagaca aaaccaggag tgtttcggac tcccttcggg gaggttgggg   4980
ctgttagtct ggattacccg cgaggaacat ccggctcacc cattctggat tccaatggag   5040
acattatagg cctatacggc aatggagttg agcttggcga tggctcatac gtcagcgcca   5100
tcgtgcaggg tgaccgtcag gaggaaccag tcccagaagc ttacacccca aacatgttga   5160
gaaagagaca gatgactgtg ctagatttgc accctggttc agggaaaacc aggaaaattc   5220
tgccacaaat aattaaggac gccatccagc agcgcctaag aacagctgtg ttggcaccga   5280
cgcgggtggt agcagcagaa atggcagaag ctttgagagg gctcccagta cgatatcaaa   5340
cttcagcagt gcagagagag caccaaggga atgaaatagt ggatgtgatg tgccacgcca   5400
ctctgacccA tagactgatg tcaccgaaca gagtgcccaa ctacaaccta tttgtcatgg   5460
atgaagctca tttcaccgac ccagccagta tagccgcacg aggatacatt gctaccaagg   5520
tggaattagg ggaggcagca gccatcttta tgacagcgac cccgcctgga accacggatc   5580
cttttcctga ctcaaatgcc ccaatccatg atttgcaaga tgagatacca gacagggcat   5640
ggagcagtgg atacgaatgg atcacagaat atgcgggtaa aaccgtgtgg tttgtggcga   5700
gcgtaaaaat ggggaatgag attgcaatgt gcctccaaag agcgggggaaa aaggtcatcc   5760 aactcaaccg caagtcctat gacacagaat acccaaaatg taagaatgga gactgggatt   5820
ttgtcattac caccgacatc tctgaaatgg gggccaactt cggtgcgagc agggtcatcg   5880
actgtagaaa gagcgtgaaa cccaccatct tagaagaggg agaaggcaga gtcatcctcg   5940
gaaacccatc tcccataacc agtgcaagcg cagctcaacg gagggcaga gtaggcagaa    6000 accccaacca agttggagat gaataccact atggggggc taccagtgaa gatgacagta    6060
acctagccca ttggacagag gcaaagatca tgttagacaa catacacatg cccaatggac    6120
tggtggccca gctctatgga ccagagaggg aaaaggcttt cacaatggat ggcgaatacc    6180
gtctcagagg tgaagaaaag aaaaacttct tagagctgct taggacggct gacctcccgg    6240
tgtggctggc ctacaaggtg gcgtccaatg gcattcagta caccgacaga aagtggtgtt    6300
ttgatgggcc gcgtacgaat gccatactgg aggacaacac cgaggtagag atagtcaccc    6360
ggatgggtga gaggaaaatc ctcaagccga gatggcttga tgcaagagtt tatgcagatc    6420
```

```
accaagccct caagtggttc aaagactttg cagcagggaa gagatcagcc gttagcttca   6480
tagaggtgct cggtcgcatg cctgagcatt tcatgggaaa gacgcgggaa gctttagaca   6540
ccatgtactt ggttgcaacg gctgagaaag gtgggaaagc acaccgaatg gctctcgaag   6600
agctgccaga tgcactggaa accatcacac ttattgtcgc cattactgtg atgacaggag   6660
gattcttcct actaatgatg cagcgaaagg gtatagggaa gatgggtctt ggagctctag   6720
tgctcacgct agctaccttc ttcctgtggg cggcagaggt tcctggaacc aaaatagcag   6780
ggaccctgct gatcgccctg ctgctgatgg tggttctcat cccagaaccg gaaaaacaga   6840
ggtcacagac agataaccaa ctggcggtgt ttctcatctg tgtcttgacc gtggttggag   6900
tggtggcagc aaacgagtac gggatgctag aaaaaaccaa agcagatctc aagagcatgt   6960
ttggcggaaa gacgcaggca tcaggactga ctggattgcc aagcatggca ctggacctgc   7020
gtccagccac agcctgggca ctgtatgggg ggagcacagt cgtgctaacc cctcttctga   7080
agcacctgat cacgtcggaa tacgtcacca catcgctagc ctcaattaac tcacaagctg   7140
gctcattatt cgtcttgcca cgaggcgtgc cttttaccga cctagacttg accgttggcc   7200
tcgtcttcct tggctgttgg ggtcaaatca ccctcacaac gtttctgaca gccatggttc   7260
tggcgacact tcactatggg tacatgctcc ctggatggca agcagaagca ctcagggctg   7320
cccagagaag gacagcggct ggaataatga agaatgccgt tgttgacgga atggtcgcca   7380
ctgatgtgcc tgaactggaa aggactactc ctctgatgca aaagaaagtc ggacaggtgc   7440
tcctcatagg ggtaagcgtg gcagcgttcc tcgtcaaccc taatgtcacc actgtgagag   7500
aagcaggggt gttggtgacg gcggctacgc ttactttgtg ggacaatgga gccagtgccg   7560
tttggaattc caccacagcc acgggactct gccatgtcat gcgaggtagc tacctggctg   7620
gaggctccat tgcttggact ctcatcaaga acgctgataa gccctccttg aaaaggggaa   7680
ggcctggggg caggacgcta ggggagcagt ggaaggaaaa actaaatgcc atgagcagag   7740
aagagttttt taaataccgg agagaggcca taatcgaggt ggaccgcact gaagcacgca   7800
gggccagacg tgaaaataac atagtgggag gacatccggt ttcgcgaggc tcagcaaaac   7860
tccgttggct cgtggagaaa ggatttgtct cgccaatagg aaaagtcatt gatctagggt   7920
gtgggcgtgg aggatggagc tactacgcag caaccctgaa gaaggtccag gaagtcagag   7980
gatacacgaa aggtggggcg ggacatgaag aaccgatgct catgcagagc tacggctgga   8040
acctggtctc cctgaagagt gggagtggac gtgttttacaa accttcagag cccagtgaca   8100
ccctgttctg tgacataggg gaatcctccc caagtccaga agtagaagaa caacgcacac   8160
tacgcgtcct agagatgaca tctgactggt tgcaccgagg acctagagag ttctgcatta   8220
aagttctctg cccttacatg cccaaggtta tagaaaaaat ggaagttctg cagcgccgct   8280
tcggaggtgg gctagtgcgt ctccccctgt cccgaaactc caatcacgag atgtattggg   8340
ttagtggagc cgctggcaat gtggtgcacg ctgtgaacat gaccagccag gtactactgg   8400
ggcgaatgga tcgcacagtg tggagagggc caaagtatga ggaagatgtc aacctaggga   8460
gcggaacaag agccgtggga aagggagaag tccatagcaa tcaggagaaa atcaagaaga   8520
gaatccagaa gcttaaagaa gaattcgcca caacgtggca caaagaccct gagcatccat   8580
accgcacttg gacataccac ggaagctatg aagtgaaggc tactggctca gccagctctc   8640
tcgtcaacgg agtggtgaag ctcatgagca aaccttggga cgccattgcc aacgtcacca   8700
ccatggccat gactgacacc accccttttg gacagcaaag agtttttcaag gagaaagttg   8760
```

```
acacgaaggc tcctgagcca ccagctggag ccaaggaagt gctcaacgag accaccaact      8820
ggctgtgggc ccacttgtca cgggaaaaaa gaccccgctt gtgcaccaag gaagaattca      8880
taaagaaagt caacagcaac gcggctcttg gagcagtgtt cgctgaacag aatcaatgga      8940
gcacggcgcg tgaggctgtg gatgacccgc ggttttggga gatggttgat gaagagaggg      9000
aaaaccatct gcgaggagag tgtcacacat gtatctacaa catgatggga aaaagagaga      9060
agaagcctgg agagtttgga aaagctaaag gaagcagggc catttggttc atgtggcttg      9120
gagcacggta tctagagttt gaagctttgg ggttcctgaa tgaagaccat tggctgagcc      9180
gagagaattc aggaggtgga gtggaaggct caggcgtcca aaagctggga tacatcctcc      9240
gtgacatagc aggaaagcaa ggagggaaaa tgtacgctga tgataccgcc gggtgggaca      9300
ctagaattac cagaactgat ttagaaaatg aagctaaggt actggagctc ctagacggtg      9360
aacaccgcat gctcgcccga gccataattg aactgactta caggcacaaa gtggtcaagg      9420
tcatgagacc tgcagcagaa ggaaagaccg tgatggacgt gatatcaaga gaagatcaaa      9480
gggggagtgg acaggtggtc acttatgctc ttaacacttt cacgaacatc gctgtccagc      9540
tcgtcaggct gatggaggct gaggggggtca ttggaccaca acacttggaa cagctaccta      9600
ggaaaaacaa gatagctgtc aggacctggc tctttgagaa tggagaggag agagtgacca      9660
ggatggcgat cagcggagac gactgtgtcg tcaagccgct ggacgacaga ttcgccacag      9720
ccctccactt cctcaacgca atgtcaaagg tcagaaaaga catccaggaa tggaagcctt      9780
cgcatggctg gcacgattgg cagcaagttc ccttctgctc taaccatttt caggagattg      9840
tgatgaaaga tggaaggagt atagttgtcc cgtgcagagg acaggatgag ctgataggca      9900
gggctcgcat ctctccagga gctggatgga atgtgaagga cacagcttgc ctggccaaag      9960
catatgcaca gatgtggcta ctcctatact tccatcgcag ggacttgcgt ctcatggcaa     10020
atgcgatttg ctcagcagtg ccagtggatt gggtgcccac aggcaggaca tcctggtcaa     10080
tacactcgaa aggagagtgg atgaccacyg aagacatgct gcaggtctgg aacagagtct     10140
ggattgaaga aaatgaatgg atgatggaca agactccaat cacaagctgg acagacgttc     10200
cgtatgtggg aaagcgtgag gacatctggt gtggcagcct catcggaacg cgatccagag     10260
caacctgggc tgagaacatc tatgcggcga taaaccaggt tagagctgtc attgggaaag     10320
aaaattatgt tgactacatg acctcactca ggagatacga agacgtcttg atccaggaag     10380
acagggtcat ctagtgtgat aaaaaaaaaa aaaaaaaaaa aaaaaaaaaa aaaaaaaaaa     10440
aaaaaaaaaa aaaaaaaaaa aaaaaaaaaa aaaaaaaaaa aaaaaaaaaa aaaaaaaaaa     10500
aaaaaaaaaa aaaaaaaaaa aaaaaaaaaa aaaaaaaaaa aaaaaaaaaa agcatattga     10560
cacctgggaa tagactggga gatcttctgc tctatctcaa catcagctac taggcacaga     10620
gcgccgaagt atgtagctgg tagtgaggaa gaacacagga tct                      10663
```

```
<210> SEQ ID NO 3
<211> LENGTH: 10523
<212> TYPE: DNA
<213> ORGANISM: Dengue virus type 2

<400> SEQUENCE: 3
agttgttagt ctacgtggac cgacaaagac agattctttg agggagctaa gctcaacgta       60
gttctaacag ttttttaatt agagagcaga tctctgatga ataaccaacg aaaaaaggcg      120
agaaatacgc ctttcaatat gctgaaacgc gagagaaacc gcgtgtcgac tgtacaacag      180
ctgacaaaga gattctcact tggaatgctg cagggacgag gaccattaaa actgttcatg      240
```

```
gccctggtgg cgttccttcg tttcctaaca atcccaccaa cagcagggat actgaagaga       300
tggggaacaa ttaaaaaatc aaaagccatt aatgttttga gagggttcag gaaagagatt       360
ggaaggatgc tgaacatctt gaacaggaga cgcagaactg caggcatgat cattatgctg       420
attccaacag tgatggcgtt ccatttaacc acacgtaacg gagaaccaca catgatcgtc       480
agtagacaag agaaagggaa aagtcttctg tttaaaacag aggatggtgt gaacatgtgt       540
accctcatgg ccatggacct tggtgaattg tgtgaagata caatcacgta caagtgtcct       600
tttctcaggc agaatgaacc agaagacata gattgttggt gcaactctac gtccacatgg       660
gtaacttatg ggacgtgtac caccacagga gaacacagaa gagaaaaaag atcagtggca       720
ctcgttccac atgtgggaat gggactggag acacgaactg aaacatggat gtcatcagaa       780
ggggcctgga acatgcccca gagaattgaa acttggatct tgagacatcc aggctttacc       840
ataatggcag caatcctggc atacaccata ggaacgacac atttccaaag agccctgatt       900
ttcatcttac tgacagctgt cgctccttca atgacaatgc gttgcatagg aatatcaaat       960
agagactttg tagaaggggt ttcaggagga agctgggttg acatagtctt agaacatgga      1020
agctgtgtga cgacgatggc aaaaaacaaa ccaacattgg attttgaact gataaaaaca      1080
gaagccaaac aacctgccac tctaaggaag tactgtatag aggcaaagct gaccaacaca      1140
acaacagatt ctcgctgccc aacacaagga gaacccagcc taaatgaaga gcaggacaaa      1200
aggttcgtct gcaaacactc catggtggac agaggatggg gaaatggatg tggattattt      1260
ggaaaaggag gcattgtgac ctgtgctatg ttcacatgca aaaagaacat gaaaggaaaa      1320
gtcgtgcaac agaaaacttt ggaatacacc attgtgataa cacctcactc aggggaagag      1380
catgcagtcg gaaatgacac aggaaaacat ggcaaggaaa tcaaaataac accacagagt      1440
tccatcacag aagcagagtt gacaggctat ggcactgtca cgatggagtg ctctccgaga      1500
acgggcctcg acttcaatga gatggtgttg ctgcaaatgg aaaataaagc ttggctggtg      1560
cacaggcaat ggttcctaga cctgccgttg ccatggctgc ccggagcgga cacacaagga      1620
tcaaattgga tacagaaaga gacattggtc actttcaaaa atccccatgc gaagaaacag      1680
gatgttgttg tttttgggatc ccaagaaggg gccatgcaca cagcactcac aggggccaca      1740
gaaatccaga tgtcatcagg aaacttactg ttcacaggac atctcaagtg caggctgagg      1800
atggacaaac tacagctcaa aggaatgtca tactctatgt gcacaggaaa gtttaaagtt      1860
gtgaaggaaa tagcagaaac acaacatgga acaatagtta tcagagtaca atatgaaggg      1920
gacggttctc catgtaagat ccctttttgag ataatggatt ggaaaaaag acatgtttta      1980 ggtcgcctga ttacagtcaa cccaatcgta acagaaaaag atagcccagt caacatagaa      2040
gcagaacctc cattcggaga cagctacatc atcataggag tagagccggg acaattgaag      2100
ctcaactggt ttaagaaagg aagttctatc ggccaaatga ttgagacaac aatgagggga      2160
gcgaagagaa tggccatttt aggtgacaca gcttgggatt ttggatccct gggaggagtg      2220
tttacatcta taggaaaggc tctccaccaa gttttcggag caatctatgg ggctgccttc      2280
agtggggtct catggactat gaaaatactc ataggagtca ttatcacatg gataggaatg      2340
aattcacgca gcacctcact gtctgtgtca ctagtattgg tgggagtcgt gacgctgtat      2400
ttgggagtta tggtgcaggc cgatagtggt tgcgttgtga gctggaaaaa caaagaactg      2460
aagtgtggca gtgggatttt catcacagac aacgtgcaca catggacaga acaatacaag      2520
ttccaaccag aatcccttc aaagctagct tcagctatcc agaaagctca tgaagagggc      2580
```

-continued

```
atttgtggaa tccgctcagt aacaagactg gaaaatctga tgtggaaaca aataacacca    2640
gaattgaatc acattctatc agaaaatgag gtgaagttga ctattatgac aggagacatc    2700
aaaggaatca tgcaggcagg aaaacgatct ctgcagcccc agcccactga gctgaagtat    2760
tcatggaaaa catggggcaa agcgaaaatg ctctctacag agtctcataa ccagaccttt    2820
ctcattgatg gccccgaaac agcagaatgc cccaacacaa acagagcttg gaattcgctg    2880
gaagttgaag actatggctt tggagtattc accaccaata tatggctaaa gttgagagaa    2940
aagcaggatg tattctgcga ctcaaaactc atgtcagcgg ccataaaaga caacagagcc    3000
gtccatgccg atatgggtta ttggatagaa agtgcactca atgacacatg gaagatagag    3060
aaagcctctt tcatcgaagt taaaagctgc cactggccaa agtcacacac cctctggagt    3120
aatggagtgt tagaaagtga gatgataatt ccaaagaatt tcgctggacc agtgtcacaa    3180
cacaactaca gaccaggcta ccatacacaa acagcaggac catggcatct aggtaagctt    3240
gagatggact ttgatttctg cgaaggaacc acagtggtgg tgactgagga ctgtggaaat    3300
agaggaccct ctttaagaac aactactgcc tctggaaaac tcataacaga atggtgctgc    3360
cgatcttgca cattaccacc gctaagatac agaggtgagg acggatgctg gtacgggatg    3420
gaaatcagac cattgaaaga gaaagaagag aatttggtca actccttggt cacagccgga    3480
catgggcaga ttgacaactt ttcactagga gtcttgggaa tggcattgtt cctggaagaa    3540
atgctcagga cccgagtagg aacgaaacat gcaatactac tagttgcagt ttctttttgtg    3600 acattgatca cagggaacat gtcctttaga gacctgggaa gagtgatggt tatggtgggc    3660
gctactatga cggatgacat aggtatgggc gtgacttatc ttgccctact agcagccttc    3720
aaagtcagac caactttttgc agctggacta ctcttgagaa agttgaccte caaggaattg    3780 atgatgacta ccataggaat cgtactcctc tcccagagca ccataccaga gaccattctt    3840
gaactgactg atgcgttagc cttgggcatg atggtcctta aaatggtgag aaaaatggaa    3900
aagtatcaat tggcagtgac tatcatggct atcttgtgcg tcccaaatgc agtgatatta    3960
caaaacgcat ggaaagtgag ttgcacaata ttggcagtgg tgtccgtttc cccactgttc    4020
ttaacatcct cacagcagaa agcggattgg ataccattag cattgacgat caagggtctc    4080
aatccaacag ctatttttct aacaaccctt tcaagaacca acaagaaaag gagctggcca    4140
ctaaatgagg ctatcatggc agtcgggatg gtgagcattt tggccagttc actcctaaag    4200
aatgacattc ccatgacagg accattagtg gctggagggc tcctcactgt gtgctacgtg    4260
ctcactggac gatcggccga tttggaactg gagagagccg ccgatgtcaa atgggaagat    4320
caggcagaga tatcagggag ctctccaatc ctgtcaataa caatatcaga agatggtagc    4380
atgtcgataa aaaacgaaga ggaagaacaa acactgacca tactcattag aacaggattg    4440
ctggtgatct caggacttttt tcctgtatca ataccaatca cggcagcagc atggtacctg    4500
tgggaagtga agaacaacg ggctggagta ttgtgggatg tcccttcacc cccaccccgtg    4560 ggaaaggctg aactggaaga tggagcctat agaatcaagc aaaaagggat tcttggatat    4620
tcccagatcg gagccggagt ttacaaagaa ggaacattcc atacaatgtg gcatgtcaca    4680
cgcggcgctg ttctaatgca taaaggaaag aggattgaac catcatgggc ggacgttaag    4740
aaagacctaa tatcatatgg aggaggctgg aagctagaag gagaatggaa ggaaggagaa    4800
gaagtccagg tcttggcatt ggagcctgga aaaaatccaa gagccgtcca aacaaaacct    4860
ggtcttttca aaaccaacgc cggaaccata ggtgccgtat ctctggactt ttctcctgga    4920
acctcaggat ctccaatcat cgacaaaaaa ggaaaagttg tgggtcttta tggtaatggt    4980
```

```
gttgttacaa ggagtggagc atatgtgagt gctatagccc agactgaaaa aagtattgaa    5040
gacaatccag agatcgaaga tgatattttt cgaaagagaa aattgaccat catggacctc    5100
cacccaggag cgggaaagac gaagagatac cttccggcca tagtcagaga ggctataaaa    5160
cggggcctga ggacattaat cctggccccc actagagtcg tggcagctga aatggaggaa    5220
gccctaagag gacttccaat aagataccaa accccagcca tcagagctga gcacaccggg    5280
cgggagattg tggacctaat gtgtcatgcc acattcacta tgaggctgct atcaccagtt    5340
agagtgccaa attacaacct gatcatcatg gacgaagccc atttcacaga cccagcaagt    5400
atagcggcta gaggatacat ctcaactcga gtagagatgg gtgaggcagc tgggattttc    5460
atgacagcca ctcctccggg aagcagagac ccattccctc agagcaatgc accaatcatg    5520
gatgaagaaa gagaaatccc tgaacgttcg tggagttctg gacatgagtg ggtcacggat    5580
tttaaaggga agactgtttg gttcgttcca agtataaaag caggaaatga tatagcagct    5640
tgcctgagaa aaaatggaaa gaaagtgata caactcagta ggaagacctt tgattctgag    5700
tatgtcaaga ctagaaccaa tgattgggac ttcgtggtca caactgacat ttcagaaatg    5760
ggtgccaact tcaaggctga gagggttata dacccccagac gctgcatgaa accagttata    5820
ctaacagatg gtgaagagcg ggtgatcctg gcaggaccta tgccagtgac ccactctagt    5880
gcagcacaaa aagagggggag aataggaaga aatccaaaaa atgaaaatga ccagtacata    5940
tacatggggg aacctctgga aaatgatgaa gactgtgcac actggaaaga agctaaaatg    6000
ctcctagata acatcaacac acctgaagga atcattccta gcatgttcga accagagcgt    6060
gaaaaggtgg atgccattga tggtgaatac cgcttgagag gagaagcaag gaaaaccttt    6120
gtggacctaa tgagaagagg agacctacca gtctggttgg cctacagagt ggcagctgaa    6180
ggcatcaact acgcagacag aaggtggtgt tttgatggaa ttaagaacaa ccaaatcttg    6240
gaagaaaatg tggaggtgga aatctggaca aaagaagggg aaaggaagaa attaaaaccc    6300
agatggttgg atgccaggat ctactctgac ccactgacgc taaaggaatt caaggagttt    6360
gcagctggaa gaaagtccct gaccctgaac ctaatcacag aaatgggtag gcttccaact    6420
ttcatgactc agaaggcaag agacgcactg gacaacttag cagtgctgca cacggctgaa    6480
gcaggtggaa gggcgtacaa tcatgctctc agtgaactgc cggagaccct ggagacattg    6540
cttttactga cacttctggc tacagtcaca ggaggaatct ttttattctt gatgtccgga    6600
aggggtatag ggaagatgac cctgggaatg tgctgcataa tcacggccag tattctccta    6660
tggtacgcac aaatacagcc acactggata gcagcttcaa taatactgga gttttttctc    6720
atagttttgc ttattccaga accagaaaag cagagaacac cccaagataa ccaattgacc    6780
tacgttgtca tagccatcct cacagtggtg gccgcaacca tggcaaacga gatgggtttc    6840
ctggaaaaaa cgaagaaaga tctcggattg ggaagcatta caacccagca acccgagagc    6900
aacatcctgg acatagatct acgtcccgca tcagcatgga cgctgtatgc tgtggccaca    6960
acatttgtca caccaatgtt gagacacagc attgaaaatt cctcagtgaa cgtgtcccta    7020
acagctattg ccaaccaagc cacagtgtta atgggtcttg ggaaaggatg gccattgtca    7080
aagatggaca tcggagttcc ccttctcgcc attggatgct actcacaagt caaccccata    7140
actctcacag cagctctttt cttactggta gcacattatg ccatcatagg gccaggactc    7200
caagcaaaag caaccaggga agctcagaaa agagcagcag cgggcatcat gaaaaaccca    7260
actgtcgatg ga ataacagt gattgaccta gatccaatac cctatgatcc aaagtttgaa    7320
```

-continued

```
aagcagttgg gacaagtaat gctcctagtc ctctgcgtga ctcaagtgtt gatgatgagg   7380
actacatggg ctctgtgtga ggcgttaacc ttagcgaccg ggcctatctc cacattgtgg   7440
gaaggaaatc cagggaggtt ttggaacact accattgcag tgtcaatggc taacattttt   7500
agagggagtt acttggccgg agctggactt ctctttttcca tcatgaagaa cacaaccaac   7560
acgagaaggg gaaccggtaa cataggagag acgcttggag agaaatggaa aagccgattg   7620
aacgcattgg ggaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgtcgag agaaatatgg tcacaccaga agggaaagta   7800
gtggacctcg gttgcggcag aggaggctgg tcatactatt gtgggggact aaagaatgta   7860
agagaagtca aaggcctgac aaaaggagga ccaggacatg aagaacccat ccccatgtca   7920
acatatgggt ggaatctagt acgtcttcaa agtggagttg acgttttctt cactccgcca   7980
gaaaagtgtg acacattgtt gtgtgacata ggggagtcgt caccaaatcc cacggtagaa   8040
gcaggacgaa cactcagagt ccttaactta gtggaaaatt ggttgaacaa caacacccaa   8100
ttttgcataa aggttctcaa cccatacatg ccctcagtca tagaaaaaat ggaagcacta   8160
caaaggaaat atggaggagc cttagtgagg aatccactct cacgaaactc cacacatgag   8220
atgtactggg tatccaatgc ctccgggaac atagtgtcat cagtgaacat gatttcaagg   8280
atgttgatca acagattcac aatgagacac aagaaagcca cttacgagcc agatgtagac   8340
ctcggaagcg gaacccgcaa catcggaatt gaaagtgaga taccaaacct agacataatc   8400
gggaaaagaa tagaaaaaat aaaacaagag catgaaacat catggcacta tgaccaagac   8460
cacccataca aaacgtgggc ttaccatggc agctatgaaa caaaacaaac tggatcagca   8520
tcatccatgg tgaacggagt ggtcagactg ctgacaaaac cttgggacgt cgtccccatg   8580
gtgacacaga tggcaatgac agacacgact ccatttggac aacagcgcgt ttttaaagaa   8640
aaagtggaca cgagaaccca agaaccgaaa gaaggcacaa agaaactaat gaaaatcacg   8700
gcagagtggc tttggaaaga actagggaag aaaaagacac ctaggatgtg cactagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtataacat gatgggaaaa   8940
agagagaaga agctagggga gttcggcaag gcaaaaggca gcagagccat atggtacatg   9000
tggcttggag cacgcttctt agagtttgaa gccctaggat tcttgaatga agatcactgg   9060
ttctccagag agaactcctt gagtggagtg gaaggagaag ggctgcacaa gctaggttac   9120
attttaagag acgtgagcaa gaaagaggga ggagcaatgt atgccgatga caccgcagga   9180
tgggacacaa gaatcacact agaagaccta aaaaatgaag aaatggtaac aaaccacatg   9240
gaaggagaac acaagaaact agccgaggcc attttcaaat taacgtacca aaacaaggtg   9300
gtgcgtgtgc aaagaccaac accaagaggc acagtaatgg atatcatatc gagaagagac   9360
caaagaggta gtggacaagt tggtacctat ggactcaata cttttcaccaa tatggaagcc   9420 caactaatca gacagatgga gggagaagga gtcttcaaaa gcattcagca cctgacagtc   9480
acagaagaaa tcgccgtgca aaactggtta gcaagagtag ggcgcgaaag gttatcaaga   9540
atggccatca gtggagatga ttgtgttgtg aaacctttag atgacaggtt cgcaagcgct   9600
ttaacagctc taaatgacat gggaaaggtt aggaaagaca tacaacaatg gaaccttca   9660 agaggatgga acgattggac acaagtgccc ttctgttcac accatttcca tgagttaatc   9720
```

-continued

```
atgaaagacg gacgcgtact tgtagttcca tgcagaaacc aagatgaact gattggtaga        9780
gcccgaattt cccaaggagc tgggtggtct ttgcgagaga cggcctgttt ggggaagtcc        9840
tacgcccaaa tgtggagctt gatgtacttc cacagacgtg acctcaggct ggcggctaat        9900
gctatttgct cggcagtccc atcacattgg gttccaacaa gtagaacaac ctggtccata        9960
cacgccaaac atgaatggat gacaacggaa gacatgctga cagtctggaa cagggtgtgg       10020
attcaagaaa acccatggat ggaagacaaa actccagtgg aatcatggga ggaaatccca       10080
tacttgggga aaagagaaga ccaatggtgc ggctcattga ttgggctaac aagcagggcc       10140
acctgggcaa agaacatcca aacagcaata aatcaagtta gatcccttat aggcaatgag       10200
gaatacacag attacatgcc atccatgaaa agattcagaa gagaagagga agaggcagga       10260
gtcctgtggt agaaggcaaa aaaaaaaaaa aaaaaaaaaa aaaaaaaaaa aaaaaaaaaa       10320
aaaaaaaaaa aaaaaaaaaa aaaaaaaaaa aaaaaaaaaa aaaaaaaaaa aaaaaaaaaa       10380
aaaaaaaaaa aaaaaaaaaa aaaaaaaaaa aaaaaacag catattgacg ctgggaaaga       10440
ccagagatcc tgctgtctcc tcagcatcat tccaggcaca gaacgccaga aaatggaatg       10500
gtgctgttga atcaacaggt tct                                               10523
```

<210> SEQ ID NO 4
<211> LENGTH: 10775
<212> TYPE: DNA
<213> ORGANISM: Yellow fever virus

<400> SEQUENCE: 4

```
agtaaatcct gtgtgctaat tgaggtgcat tggtctgcaa atcgagttgc taggcaataa          60
acacatttgg attaatttta atcgttcgtt gagcgattag cagagaactg accagaacat         120
gtctggtcgt aaagctcagg gaaaaaccct gggcgtcaat atggtacgac gaggagttcg         180
ctccttgtca aacaaaataa aacaaaaaac aaaacaaatt ggaaacagac ctggaccttc         240
aagaggtgtt caaggattta tcttttttctt tttgttcaac attttgactg gaaaaaagat         300
cacagcccac ctaaagaggt tgtggaaaat gctggaccca agacaaggct tggctgttct         360
aaggaaagtc aagagagtgg tggccagttt gatgagagga ttgtcctcaa ggaaacgccg         420
ttcccatgat gttctgactg tgcaattcct aattttggga atgctgttga tgacgggtgg         480
agtgaccttg gtgcggaaaa acagatggtt gctcctaaat gtgacatctg aggacctcgg         540
gaaaacattc tctgtgggca caggcaactg cacaacaaac attttggaag ccaagtactg         600
gtgcccagac tcaatggaat acaactgtcc caatctcagt ccaagagagg agccagatga         660
cattgattgc tggtgctatg gggtggaaaa cgttagagtc gcatatggta agtgtgactc         720
agcaggcagg tctaggaggt caagaagggc cattgacttg cctacgcatg aaaaccatgg         780
tttgaagacc cggcaagaaa aatggatgac tggaagaatg ggtgaaaggc aactccaaaa         840
gattgagaga tggttcgtga ggaacccctt ttttgcagtg acggctctga ccattgccta         900
ccttgtggga agcaacatga cgcaacgagt cgtgattgcc ctactggtct tggctgttgg         960
tccggcctac tcagctcact gcattggaat tactgacagg gatttcattg aggggggtgca       1020 tggaggaact tgggtttcag ctaccctgga gcaagacaag tgtgtcactg ttatggcccc       1080
tgacaagcct tcattggaca tctcactaga gacagtagcc attgatagac ctgctgaggt       1140
gaggaaagtg tgttacaatg cagttctcac tcatgtgaag attaatgaca gtgccccag       1200 cactggagag gcccacctag ctgaagagaa cgaaggggac aatgcgtgca gcgcactta       1260
```

-continued

```
ttctgataga ggctggggca atggctgtgg cctatttggg aaagggagca ttgtggcatg    1320
cgccaaattc acttgtgcca aatccatgag tttgtttgag gttgatcaga ccaaaattca    1380
gtatgtcatc agagcacaat tgcatgtagg ggccaagcag gaaaattgga ataccgacat    1440
taagactctc aagtttgatg ccctgtcagg ctcccaggaa gtcgagttca ttgggtatgg    1500
aaaagctaca ctggaatgcc aggtgcaaac tgcggtggac tttggtaaca gttacatcgc    1560
tgagatggaa acagagagct ggatagtgga cagacagtgg gcccaggact tgaccctgcc    1620
atggcagagt ggaagtggcg gggtgtggag agagatgcat catcttgtcg aatttgaacc    1680
tccgcatgcc gccactatca gagtactggc cctgggaaac caggaaggct ccttgaaaac    1740
agctcttact ggcgcaatga gggttacaaa ggacacaaat gacaacaacc tttacaaact    1800
acatggtgga catgtttctt gcagagtgaa attgtcagct ttgacactca aggggacatc    1860
ctacaaaata tgcactgaca aaatgttttt tgtcaagaac ccaactgaca ctggccatgg    1920
cactgttgtg atgcaggtga aagtgtcaaa aggagccccc tgcaggattc cagtgatagt    1980
agctgatgat cttacagcgg caatcaataa aggcattttg gttacagtta accccatcgc    2040
ctcaaccaat gatgatgaag tgctgattga ggtgaaccca ccttttggag acagctacat    2100
tatcgttggg agaggagatt cacgtctcac ttaccagtgg cacaaagagg gaagctcaat    2160
aggaaagttg ttcactcaga ccatgaaagg cgtggaacgc ctggccgtca tgggagacac    2220
cgcctgggat ttcagctccg ctggagggtt cttcacttcg gttgggaaag gaattcatac    2280
ggtgtttggc tctgcctttc aggggctatt tggcggcttg aactggataa caaaggtcat    2340
catgggggcg gtacttatat gggttggcat caacacaaga aacatgacaa tgtccatgag    2400
catgatcttg gtaggagtga tcatgatgtt tttgtctcta ggagttgggg cggatcaagg    2460
atgcgccatc aactttggca agagagagct caagtgcgga gatggtatct tcatatttag    2520
agactctgat gactggctga acaagtactc atactatcca gaagatcctg tgaagcttgc    2580
atcaatagtg aaagcctctt ttgaagaagg gaagtgtggc ctaaattcag ttgactccct    2640
tgagcatgag atgtggagaa gcagggcaga tgagatcaat gccatttttg aggaaaacga    2700
ggtggacatt tctgttgtcg tgcaggatcc aaagaatgtt taccagagag gaactcatcc    2760
attttccaga attcgggatg gtctgcagta tggttggaag acttgggggta agaaccttgt    2820 gttctcccca gggaggaaga atggaagctt catcatagat ggaaagtcca ggaaagaatg    2880 cccgtttttca aaccgggtct ggaattcttt ccagatagag gagtttggga cgggagtgtt    2940
caccacacgc gtgtacatgg acgcagtctt tgaatacacc atagactgcg atggatctat    3000
cttgggtgca gcggtgaacg gaaaaaagag tgcccatggc tctccaacat tttggatggg    3060
aagtcatgaa gtaaatggga catggatgat ccacaccttg gaggcattag attacaagga    3120
gtgtgagtgg ccactgacac atacgattgg aacatcagtt gaagagagtg aaatgttcat    3180
gccgagatca atcggaggcc cagttagctc tcacaatcat atccctggat acaaggttca    3240
gacgaacgga ccttggatgc aggtaccact agaagtgaag agagaagctt gcccagggac    3300
tagcgtgatc attgatggca actgtgatgg acggggaaaa tcaaccagat ccaccacgga    3360
tagcgggaaa gttattcctg aatggtgttg ccgctcctgc acaatgccgc ctgtgagctt    3420
ccatggtagt gatgggtgtt ggtatcccat ggaaattagg ccaaggaaaa cgcatgaaag    3480
ccatctggtg cgctcctggg ttacagctgg agaaatacat gctgtccctt ttggtttggt    3540
gagcatgatg atagcaatgg aagtggtcct aaggaaaaga cagggaccaa agcaaatgtt    3600
ggttggagga gtagtgctct tgggagcaat gctggtcggg caagtaactc tccttgattt    3660
```

-continued

```
gctgaaactc acagtggctg tgggattgca tttccatgag atgaacaatg gaggagacgc    3720
catgtatatg gcgttgattg ctgccttttc aatcagacca gggctgctca tcggctttgg    3780
gctcaggacc ctatggagcc ctcgggaacg ccttgtgctg accctaggag cagccatggt    3840
ggagattgcc ttgggtggcg tgatgggcgg cctgtggaag tatctaaatg cagtttctct    3900
ctgcatcctg acaataaatg ctgttgcttc taggaaagca tcaaatacca tcttgcccct    3960
catggctctg ttgacacctg tcactatggc tgaggtgaga cttgccgcaa tgttcttttg    4020
tgccgtggtt atcatagggg tccttcacca gaatttcaag gacacctcca tgcagaagac    4080
tatacctctg gtggccctca cactcacatc ttacctgggc ttgacacaac cttttttggg    4140
cctgtgtgca tttctggcaa cccgcatatt tgggcgaagg agtatcccag tgaatgaggc    4200
actcgcagca gctggtctag tgggagtgct ggcaggactg gcttttcagg agatggagaa    4260
cttccttggt ccgattgcag ttggaggact cctgatgatg ctggttagcg tggctgggag    4320
ggtggatggg ctagagctca agaagcttgg tgaagtttca tgggaagagg aggcggagat    4380
cagcgggagt tccgcccgct atgatgtggc actcagtgaa caaggggagt tcaagctgct    4440
ttctgaagag aaagtgccat gggaccaggt tgtgatgacc tcgctggcct tggttggggc    4500
tgccctccat ccatttgctc ttctgctggt ccttgctggg tggctgtttc atgtcagggg    4560
agctaggaga agtggggatg tcttgtggga tattcccact cctaagatca tcgaggaatg    4620
tgaacatctg gaggatggga tttatggcat attccagtca accttcttgg gggcctccca    4680
gcgaggagtg ggagtggcac agggaggggg gttccacaca atgtggcatg tcacaagagg    4740
agctttcctt gtcaggaatg gcaagaagtt gattccatct tgggcttcag taaaggaaga    4800
ccttgtcgcc tatggtggct catggaagtt ggaaggcaga tgggatggag aggaagaggt    4860
ccagttgatc gcggctgttc aggaaagaa cgtggtcaac gtccagacaa aaccgagctt    4920
gttcaaagtg aggaatgggg gagaaatcgg ggctgtcgct cttgactatc cgagtggcac    4980
ttcaggatct cctattgtta acaggaacgg agaggtgatt gggctgtacg gcaatggcat    5040
ccttgtcggt gacaactcct tcgtgtccgc catatcccag actgaggtga aggaagaagg    5100
aaaggaggag ctccaagaga tcccgacaat gctaaagaaa ggaatgacaa ctgtccttga    5160
ttttcatcct ggagctggga agacaagacg tttcctccca cagatcttgg ccgagtgcgc    5220
acggagacgc ttgcgcactc ttgtgttggc ccccaccagg gttgttcttt ctgaaatgaa    5280
ggaggctttt cacggcctgg acgtgaaatt ccacacacag gctttttccg ctcacggcag    5340
cgggagagaa gtcattgatg ccatgtgcca tgccacccta acttacagga tgttggaacc    5400
aactagggtt gttaactggg aagtgatcat tatggatgaa gcccattttt tggatccagc    5460
tagcatagcc gctagaggtt gggcagcgca cagagctagg gcaaatgaaa gtgcaacaat    5520
cttgatgaca gccacaccgc ctgggactag tgatgaattt ccacattcaa atggtgaaat    5580
agaagatgtt caaacggaca tacccagtga gccctggaac acaggcatg  actggatcct    5640 agctgacaaa aggcccacgg catggttcct tccatccatc agagctgcaa atgtcatggc    5700
tgcctctttg cgtaaggctg gaaagagtgt ggtggtcctg aacaggaaaa cctttgagag    5760 agaataccc  acgataaagc agaagaaacc tgactttata ttggccactg acatagctga    5820
aatgggagcc aacctttgcg tggagcgagt gctggattgc aggacggctt ttaagcctgt    5880
gcttgtggat gaagggagga aggtggcaat aaaagggcca cttcgtatct ccgcatcctc    5940
tgctgctcaa aggagggggc gcattgggag aaatcccaac agagatggag actcatacta    6000
```

-continued

```
ctattctgag cctacaagtg aaaataatgc ccaccacgtc tgctggttgg aggcctcaat    6060
gctcttggac aacatggagg tgaggggtgg aatggtcgcc ccactctatg gcgttgaagg    6120
aactaaaaca ccagtttccc ctggtgaaat gagactgagg gatgaccaga ggaaagtctt    6180
cagagaacta gtgaggaatt gtgacctgcc cgtttggctt tcgtggcaag tggccaaggc    6240
tggtttgaag acgaatgatc gtaagtggtg ttttgaaggc cctgaggaac atgagatctt    6300
gaatgacagc ggtgaaacag tgaagtgcag ggctcctgga ggagcaaaga agcctctgcg    6360
cccaaggtgg tgtgatgaaa gggtgtcatc tgaccagagt gcgctgtctg aatttattaa    6420
gtttgctgaa ggtaggaggg gagctgctga agtgctagtt gtgctgagtg aactccctga    6480
tttcctggct aaaaaaggtg gagaggcaat ggataccatc agtgtgttcc tccactctga    6540
ggaaggctct agggcttacc gcaatgcact atcaatgatg cctgaggcaa tgacaatagt    6600
catgctgttt atactggctg gactactgac atcgggaatg gtcatctttt tcatgtctcc    6660
caaaggcatc agtagaatgt ctatggcgat gggcacaatg gccggctgtg gatatctcat    6720
gttccttgga ggcgtcaaac ccactcacat ctcctatgtc atgctcatat tctttgtcct    6780
gatggtggtt gtgatccccg agccagggca acaaaggtcc atccaagaca accaagtggc    6840
atacctcatt attggcatcc tgacgctggt ttcagcggtg gcagccaacg agctaggcat    6900
gctggagaaa accaaagagg acctctttgg gaagaagaac ttaattccat ctagtgcttc    6960
accctggagt tggccggatc ttgacctgaa gccaggagct gcctggacag tgtacgttgg    7020
cattgttaca atgctctctc caatgttgca ccactggatc aaagtcgaat atggcaacct    7080
gtctctgtct ggaatagccc agtcagcctc agtcctttct ttcatggaca aggggatacc    7140
attcatgaag atgaatatct cggtcataat gctgctggtc agtggctgga attcaataac    7200
agtgatgcct ctgctctgtg gcataggggtg cgccatgctc cactggtctc tcattttacc    7260
tggaatcaaa gcgcagcagt caaagcttgc acagagaagg gtgttccatg gcgttgccaa    7320
gaaccctgtg gttgatggga atccaacagt tgacattgag gaagctcctg aaatgcctgc    7380 ccttttatgag aagaaactgg ctctatatct ccttcttgct ctcagcctag cttctgttgc    7440
catgtgcaga acgcccttttt cattggctga aggcattgtc ctagcatcag ctgccttagg    7500
gccgctcata gagggaaaca ccagccttct ttggaatgga cccatggctg tctccatgac    7560
aggagtcatg agggggaatc actatgcttt tgtgggagtc atgtacaatc tatggaagat    7620
gaaaactgga cgccggggga gcgcgaatgg aaaaactttg ggtgaagtct ggaagaggga    7680
actgaatctg ttggacaagc gacagtttga gttgtataaa aggaccgaca ttgtggaggt    7740
ggatcgtgat acggcacgca ggcatttggc cgaagggaag gtggacaccg gggtggcggt    7800
ctccaggggg accgcaaagt taaggtggtt ccatgagcgt ggctatgtca agctggaagg    7860
tagggtgatt gacctggggt gtggccgcgg aggctggtgt tactacgctg ctgcgcaaaa    7920
ggaagtgagt ggggtcaaag gatttactct tggaagagac ggccatgaga aacccatgaa    7980
tgtgcaaagt ctgggatgga acatcatcac cttcaaggac aaaactgata tccaccgcct    8040
agaaccagtg aaatgtgaca cccttttgtg tgacattgga gagtcatcat cgtcatcggt    8100
cacagagggg gaaaggaccg tgagagttct tgatactgta gaaaaatggc tggcttgtgg    8160
ggttgacaac ttctgtgtga aggtgttagc tccatacatg ccagatgttc tcgagaaact    8220
ggaattgctc caaaggaggt ttggcggaac agtgatcagg aaccctctct ccaggaattc    8280
cactcatgaa atgtactacg tgtctggagc ccgcagcaat gtcacattta ctgtgaacca    8340
aacatcccgc ctcctgatga ggagaatgag gcgtccaact ggaaaagtga ccctggaggc    8400
```

-continued

```
tgacgtcatc ctcccaattg ggacacgcag tgttgagaca gacaagggac ccctggacaa    8460
agaggccata gaagaaaggg ttgagaggat aaaatctgag tacatgacct cttggtttta    8520
tgacaatgac aacccctaca ggacctggca ctactgtggc tcctatgtca caaaaacctc    8580
aggaagtgcg gcgagcatgg taaatggtgt tattaaaatt ctgacatatc catgggacag    8640
gatagaggag gtcacaagaa tggcaatgac tgacacaacc ccttttggac agcaaagagt    8700
gtttaaagaa aaagttgaca ccagagcaaa ggatccacca gcgggaacta ggaagatcat    8760
gaaagttgtc aacaggtggc tgttccgcca cctggccaga gaaaagaacc ccagactgtg    8820
cacaaaggaa gaatttattg caaaagtccg aagtcatgca gccattggag cttacctgga    8880
agaacaagaa cagtggaaga ctgccaatga ggctgtccaa gacccaaagt tctgggaact    8940
ggtggatgaa gaaaggaagc tgcaccaaca aggcaggtgt cggacttgtg tgtacaacat    9000
gatggggaaa agagagaaga agctgtcaga gtttgggaaa gcaaagggaa gccgtgccat    9060
atggtatatg tggctgggag cgcggtatct tgagtttgag gccctgggat tcctgaatga    9120
ggaccattgg gcttccaggg aaaactcagg aggaggagtg gaaggcattg gcttacaata    9180
cctaggatat gtgatcagag acctggctgc aatggatggt ggtggattct acgcggatga    9240
caccgctgga tgggacacgc gcatcacaga ggcagacctt gatgatgaac aggagatctt    9300
gaactacatg agcccacatc acaaaaaact ggcacaagca gtgatggaaa tgacatacaa    9360
gaacaaagtg gtgaaagtgt tgagaccagc cccaggaggg aaagcctaca tggatgtcat    9420
aagtcgacga gaccagagag gatccgggca ggtagtgact tatgctctga acaccatcac    9480
caacttgaaa gtccaattga tcagaatggc agaagcagag atggtgatac atcaccaaca    9540
tgttcaagat tgtgatgaat cagttctgac caggctggag gcatggctca ctgagcacgg    9600
atgtgacaga ctgaagagga tggcggtgag tggagacgac tgtgtggtcc ggcccatcga    9660
tgacaggttc ggcctggccc tgtcccatct caacgccatg tccaaggtta gaaaggacat    9720
atctgaatgg cagccatcaa aagggtggaa tgattgggag aatgtgccct tctgttccca    9780
ccacttccat gaactacagc tgaaggatgg caggaggatt gtggtgcctt gccgagaaca    9840
ggacgagctc attgggagag gaagggtgtc tccaggaaac ggctggatga tcaaggaaac    9900
agcttgcctc agcaaagcct atgccaacat gtggtcactg atgtattttc acaaaaggga    9960
catgaggcta ctgtcattgg ctgtttcctc agctgttccc acctcatggg ttccacaagg    10020
acgcacaaca tggtcgattc atgggaaagg ggagtggatg accacggaag acatgcttga    10080
ggtgtggaac agagtatgga taaccaacaa cccacacatg caggacaaga caatggtgaa    10140
aaaatggaga gatgtccctt atctaaccaa gagacaagac aagctgtgcg gatcactgat    10200
tggaatgacc aataggggcca cctgggcctc ccacatccat ttagtcatcc atcgtatccg    10260
aacgctgatt ggacaggaga aatacactga ctacctaaca gtcatggaca ggtattctgt    10320
ggatgctgac ctgcaactgg gtgagcttat ctgaaacacc atctaacagg aataaccggg    10380
atacaaacca cgggtggaga accggactcc ccacaacctg aaaccgggat ataaaccacg    10440
gctggagaac cggactccgc acttaaaatg aaacagaaac cgggataaaa actacggatg    10500
gagaaccgga ctccacacat tgagacagaa gaaaaaaaaa aaaaaaaaaa aaaaaaaaaa    10560
aaaaaaaaaa aaaaaaaaaa aaaaaaaaaa aaaaaaaaaa aaaaaaaaaa aaaaaaaaaa    10620
aaaaaaaaaa aaaaaaaaaa aaaaaaaaaa aaaaaaaaaa aaaccatatt gacgccaggg    10680
aaagaccgga gtggttctct gctttttcctc cagaggtctg tgagcacagt ttgctcaaga    10740
```

```
ataagcagac ctttggatga caaacacaaa accac                              10775

<210> SEQ ID NO 5
<211> LENGTH: 10625
<212> TYPE: DNA
<213> ORGANISM: zika virus

<400> SEQUENCE: 5
agttgttgat ctgtgtgagt cagactgcga cagttcgagt ttgaagcgaa agctagcaac      60
agtatcaaca ggtttttattt tggatttgga aacgagagtt tctggtcatg aaaaacccaa     120
aaaagaaatc cggaggattc cggattgtca atatgctaaa acgcggagta gcccgtgtga     180
gcccctttgg gggcttgaag aggctgccag ccggacttct gctgggtcat gggcccatca     240
ggatggtctt ggcgattcta gccttcttga gattcacggc aatcaagcca tcactgggtc     300
tcatcaatag atgggggttca gtggggaaaa aagaggctat ggaaataata aagaagttca     360
agaaagatct ggctgccatg ctgagaataa tcaatgctag gaaggagaag aagagacgag     420
gcgcagatac taatgtcgga attgttggcc tcctgctgac cacagctatg gcagcggagg     480
tcactagacg tgggagtgca tactatatgt acttggacag aaacgatgct ggggaggcca     540 tatctttttcc aaccacattg gggatgaata agtgttatat acagatcatg gatcttggac     600
acatgtgtga tgccaccatg agctatgaat gccctatgct ggatgagggg gtggaaccag     660
atgacgtcga ttgttggtgc aacacgacgt caacttgggt tgtgtacgga acctgccatc     720
acaaaaaagg tgaagcacgg agatctagaa gagctgtgac gctcccctcc cattccacta     780
ggaagctgca aacgcggtcg caaacttggt tggaatcaag agaatacaca aagcacttga     840
ttagagtcga aaattggata ttcaggaacc ctggcttcgc gttagcagca gctgccatcg     900
cttggctttt gggaagctca acgagccaaa aagtcatata cttggtcatg atactgctga     960 ttgcccggc atacagcatc aggtgcatag gagtcagcaa tagggacttt gtggaaggta    1020
tgtcaggtgg gacttgggtt gatgttgtct ggaacatgg aggttgtgtc accgtaatgg    1080
cacaggacaa accgactgtc gacatagagc tggttacaac aacagtcagc aacatggcgg    1140
aggtaagatc ctactgctat gaggcatcaa tatcggacat ggcttcggac agccgctgcc    1200
caacacaagg tgaagcctac cttgacaagc aatcagacac tcaatatgtc tgcaaaagaa    1260
cgttagtgga cagaggctgg ggaaatggat gtggactttt tggcaaaggg agcctggtga    1320
catgcgctaa gttttgcatgc tccaagaaaa tgaccgggaa gagcatccag ccagagaatc    1380
tggagtaccg gataatgctg tcagttcatg gctcccagca cagtgggatg atcgttaatg    1440
acacaggaca tgaaactgat gagaatagag cgaaggttga gataacgccc aattccaccaa    1500 gagccgaagc caccctgggg ggttttggaa gcctaggact tgattgtgaa ccgaggacag    1560
gccttgactt ttcagatttg tattacttga ctatgaataa caagcactgg ttggttcaca    1620
aggagtggtt ccacgacatt ccattacctt ggcacgctgg ggcagacacc ggaactccac    1680
actggaacaa caaagaagca ctggtagagt tcaaggacgc acatgccaaa aggcaaactg    1740
tcgtggttct agggagtcaa gaaggagcag ttcacacggc ccttgctgga gctctggagg    1800
ctgagatgga tggtgcaaag ggaaggctgt cctctggcca cttgaaatgt cgcctgaaaa    1860 tggataaaact tagattgaag ggcgtgtcat actccttgtg taccgcagcg ttcacattca    1920
ccaagatccc ggctgaaaca ctgcacgggga cagtcacagt ggaggtacag tacgcaggga    1980
cagatggacc ttgcaaggtt ccagctcaga tggcggtgga catgcaaact ctgacccag    2040 ttgggaggct gataaccgct aaccccgtaa tcactgaaag cactgagaac tccaagatga    2100
```

```
tgctggaact tgatccacca tttggggact cttacattgt cataggagtc ggggagaaga    2160
agatcaccca ccactggcac aggagtggca gcaccattgg aaaagcattt gaagccactg    2220
tgagaggtgc caggagaatg gcagtcttgg gagacacagc ctgggacttt ggatcagttg    2280
gaggcgctct caactcattg ggcaagggca tccatcaaat ttttggagca gctttcaaat    2340
cattgtttgg aggaatgtcc tggttctcac aaattctcat tggaacgttg ctgatgtggt    2400
tgggtctgaa cacaaagaat ggatctattt cccttatgtg cttggcctta gggggagtgt    2460
tgatcttctt atccacagcc gtctctgctg atgtgggggtg ctcggtggac ttctcaaaga    2520
aggagacgag atgcggtaca ggggtgttcg tctataacga cgttgaagcc tggagggaca    2580
ggtacaagta ccatcctgac tcccccgta gattggcagc agcagtcaag caagcctggg    2640
aagatggtat ctgtgggatc tcctctgttt caagaatgga aaacatcatg tggagatcag    2700 tagaaggga gctcaacgca atcctggaag agaatggagt tcaactgacg gtcgttgtgg    2760
gatctgtaaa aaacccatg tggagaggtc cacagagatt gcccgtgcct gtgaacgagc    2820
tgccccacgg ctggaaggct tgggggaaat cgtacttcgt cagagcagca aagacaaata    2880
acagctttgt cgtggatggt gacacactga aggaatgccc actcaaacat agagcatgga    2940
acagctttct tgtggaggat catgggttcg gggtatttca cactagtgtc tggctcaagg    3000
ttagagaaga ttattcatta gagtgtgatc cagccgttat tggaacagct gttaagggaa    3060
aggaggctgt acacagtgat ctaggctact ggattgagag tgagaagaat gacacatgga    3120
ggctgaagag ggcccatctg atcgagataa aaacatgtga atggccaaag tcccacacat    3180
tgtggacaga tggaatagaa gagagtgatc tgatcatacc caagtcttta gctgggccac    3240
tcagccatca caataccaga gagggctaca ggacccaaat gaaagggcca tggcacagtg    3300
aagagcttga aattcggttt gaggaatgcc caggcaccaa ggtccacgtg gaggaaacat    3360
gtggaacaag aggaccatct ctgagatcaa ccactgcaag cggaagggtg atcgaggaat    3420
ggtgctgcag ggagtgcaca atgcccccac tgtcgttcca ggctaaagat ggctgttggt    3480
atggaatgga gataaggccc aggaaagaac cagaaagtaa cttagtaagg tcaatggtga    3540
ctgcaggatc aactgatcac atggatcact tctcccttgg agtgcttgtg attctgctca    3600
tggtgcagga agggctgaag aagagaatga ccacaaagat catcataagc acatcaatgg    3660
cagtgctggt agctatgatc ctgggaggat tttcaatgag tgacctggct aagcttgcaa    3720
ttttgatggg tgccaccttc gcggaaatga acactggagg agatgtagct catctggcgc    3780
tgatagcggc attcaaagtc agaccagcgt tgctggtatc tttcatcttc agagctaatt    3840
ggacaccccg tgaaagcatg ctgctggcct tggcctcgtg tcttttgcaa actgcgatct    3900
ccgccttgga aggcgacctg atggttctca tcaatggttt tgctttggcc tggttggcaa    3960
tacgagcgat ggttgttcca cgcactgata acatcacctt ggcaatcctg ctgctctga    4020 caccactggc ccggggcaca ctgcttgtgg cgtggagagc aggccttgct acttgcgggg    4080
ggtttatgct cctctctctg aagggaaaag gcagtgtgaa gaagaactta ccatttgtca    4140
tggcccctgg actaaccgct gtgaggctgg tcgacccccat caacgtggtg ggactgctgt    4200
tgctcacaag gagtgggaag cggagctggc ccccctagcga agtactcaca gctgttggcc    4260
tgatatgcgc attggctgga gggttcgcca aggcagatat agagatggct gggcccattg    4320
ccgcggtcgg tctgctaatt gtcagttacg tggtctcagg aaagagtgtg gacatgtaca    4380
ttgaaagagc aggtgacatc acatgggaaa aagatgcgga agtcactgga aacagtcccc    4440
```

```
ggcttgatgt ggcgctagat gagagtggtg atttctccct ggtggaggat gacggtcccc   4500
ccatgagaga gatcatactc aaggtggtcc tgatgaccat ctgtggcatg aacccaatag   4560
ccataccctt tgcagctgga gcgtggtacg tatacgtgaa gactggaaaa aggagtggag   4620
ctctatggga tgtgcctgct cccaaggaag taaaaaaggg ggagaccaca gatggagtgt   4680
acagagtgat gactcgtaga ctgctaggtt caacacaagt tggagtggga gttatgcaag   4740
agggggtctt tcacaccatg tggcacgtca caaaaggatc cgcgctgaga agcggtgaag   4800
ggagacttga tccatactgg ggagatgtca agcaggatct ggtgtcatac tgtggtccat   4860
ggaagctaga tgccgcctgg gacgggcaca gcgaggtgca gctcttggcc gtgccccccg   4920
gagagagagc gaggaacatc cagactctgc ccggaatatt taagacaaag gatggggaca   4980
ttggagcggt tgcgctggat tacccagcag gaacttcagg atctccaatc ctagacaagt   5040
gtgggagagt gataggactt tatggcaatg gggtcgtgat caaaaatggg agttatgtta   5100
gtgccatcac ccaagggagg agggaggaag agactcctgt tgagtgcttc gagccttcga   5160
tgctgaagaa gaagcagcta actgtcttag acttgcatcc tggagctggg aaaaccagga   5220
gagttcttcc tgaaatagtc cgtgaagcca taaaaacaag actccgtact gtgatcttag   5280
ctccaaccag ggttgtcgct gccgaaatgg aggaagccct tagagggctt ccagtgcgtt   5340
atatgacaac agcagtcaat gtcacccact ctggaacaga aatcgtcgac ttaatgtgcc   5400
atgccacctt cacttcacgt ctactacagc caatcagagt ccccaactat aatctgtata   5460
ttatggatga ggcccacttc acagatccct caagtatagc agcaagagga tacatttcaa   5520
caagggttga gatgggcgag gcggctgcca tcttcatgac cgccacgcca ccaggaaccc   5580
gtgacgcatt tccggactcc aactcaccaa ttatggacac cgaagtggaa gtcccagaga   5640
gagcctggag ctcaggcttt gattgggtga cggatcattc tggaaaaaca gtctggtttg   5700
ttccaagcgt gaggaacggc aatgagatcg cagcttgtct gacaaaggct ggaaaacggg   5760
tcatacagct cagcagaaag actttttgaga cagagttcca gaaaacaaaa catcaagagt   5820
gggactttgt cgtgacaact gacatttcag agatgggcgc caactttaaa gctgaccgtg   5880
tcatagattc caggagatgc ctaaagccgg tcatacttga tggcgagaga gtcattctgg   5940
ctggacccat gcctgtcaca catgccagcg ctgcccagag gagggggcgc ataggcagga   6000
atcccaacaa acctggagat gagtatctgt atggaggtgg gtgcgcagag actgacgaag   6060
accatgcaca ctggcttgaa gcaagaatgc tccttgacaa tatttacctc caagatggcc   6120
tcatagcctc gctctatcga cctgaggccg acaaagtagc agccattgag ggagagttca   6180
agcttaggac ggagcaaagg aagacctttg tggaactcat gaaaagagga gatcttcctg   6240
tttggctggc ctatcaggtt gcatctgccg gaataaccta cacagataga agatggtgct   6300
ttgatggcac gaccaacaac accataatgg aagacagtgt gccggcagag gtgtggacca   6360
gacacggaga gaaagagtg ctcaaaccga ggtggatgga cgccagagtt tgttcagatc   6420
acgcggccct gaagtcattc aaggagtttg ccgctgggaa aagaggagcg cttttggag   6480 tgatggaagc cttgggaaca ctgccaggac acatgacaga gagattccag gaagccattg   6540
acaacctcgc tgtgctcatg cgggcagaga ctggaagcag gccttacaaa gccgcggcgg   6600
cccaattgcc ggagacccta gagaccatta tgcttttggg gttgctggga acagtctcgc   6660
tgggaatctt tttcgtcttg atgaggaaca agggcatagg gaagatgggc tttggaatgg   6720
tgactcttgg ggccagcgca tggctcatgt ggctctcgga aattgagcca gccagaattg   6780
catgtgtcct cattgttgtg ttcctattgc tggtggtgct catacctgag ccagaaaagc   6840
```

-continued

```
aaagatctcc ccaggacaac caaatggcaa tcatcatcat ggtagcagta ggtcttctgg   6900
gcttgattac cgccaatgaa ctcggatggt tggagagaac aaagagtgac ctaagccatc   6960
taatgggaag gagagaggag ggggcaacca taggattctc aatggacatt gacctgcggc   7020
cagcctcagc ttgggccatc tacgctgcct tgacaacttt cattacccca gccgtccaac   7080
atgcagtgac cacttcatac aacaactact ccttaatggc gatggccacg caagctggag   7140
tgttgtttgg tatgggcaaa gggatgccat tctacgcatg ggactttgga gtcccgctgc   7200
taatgatagg ttgctactca caattaacac ccctgaccct aatagtagcc atcattttgc   7260
tcgtggcgca ctacatgtac ttgatcccag ggctgcaggc agcagctgcg cgtgctgccc   7320
agaagagaac ggcagctggc atcatgaaga accctgttgt ggatggaata gtggtgactg   7380
acattgacac aatgacaatt gaccccccaag tggagaaaaa gatgggacag gtgctactca   7440
tagcagtagc cgtctccagc gccatactgt cgcggaccgc ctgggggtgg ggggaggctg   7500
gggccctgat cacagctgca acttccactt tgtgggaagg ctctccgaac aagtactgga   7560
actcctctac agccacttca ctgtgtaaca ttttaggg aagttacttg gctggagctt   7620
ctctaatcta cacagtaaca agaaacgctg gcttggtcaa gagacgtggg ggtggaacag   7680
gagagaccct gggagagaaa tggaaggccc gcttgaacca gatgtcggcc ctggagttct   7740
actcctacaa aaagtcaggc atcaccgagg tgtgcagaga agaggcccgc cgcgccctca   7800
aggacggtgt ggcaacggga ggccatgctg tgtcccgagg aagtgcaaag ctgagatggt   7860
tggtggagcg gggatacctg cagccctatg gaaaggtcat tgatcttgga gtgtggcagag  7920 ggggctggag ttactacgcc gccaccatcc gcaaagttca agaagtgaaa ggatacacaa   7980
aaggaggccc tggtcatgaa gaacccatgt tggtgcaaag ctatgggtgg aacatagtcc   8040
gtcttaagag tggggtggac gtctttcata tggcggctga gccgtgtgac acgttgctgt   8100
gtgacatagg tgagtcatca tctagtcctg aagtggaaga agcacggacg ctcagagtcc   8160
tttccatggt gggggattgg cttgaaaaaa gaccaggagc cttttgtata aaagtgttgt   8220
gcccatacac cagcactatg atggaaaccc tggagcgact gcagcgtagg tatgggggag   8280
gactggtcag agtgccactc tcccgcaact ctacacatga gatgtactgg gtctctggag   8340
cgaaaagcaa caccataaaa agtgtgtcca ccacgagcca gctcctcttg gggcgcatgg   8400
acgggcccag gaggccagtg aaatatgagg aggatgtgaa tctcggctct ggcacgcggg   8460
ctgtggtaag ctgcgctgaa gctcccaaca tgaagatcat tggtaaccgc attgaaagga   8520
tccgcagtga gcacgcggaa acgtggttct ttgacgagaa ccacccatat aggacatggg   8580
cttaccatgg aagctatgag gcccccacac aagggtcagc gtcctctcta ataaacgggg   8640
ttgtcaggct cctgtcaaaa ccctgggatg tggtgactgg agtcacagga atagccatga   8700
ccgacaccac accgtatggt cagcaaagag ttttcaagga aaaagtggac actagggtgc   8760
cagatcccca agaaggcact cgtcaggtta tgagcatggt ctcttcctgg ttgtggaaag   8820
agctaggcaa acacaaacgg ccacgagtct gtaccaaaga agagttcatc aacaaggttc   8880
gtagcaatgc agcattaggg gcaatatttg aagaggaaaa agagtggaag actgcagtgg   8940
aagctgtgaa cgatccaagg ttctgggctc tagtggacaa ggaaagagag caccacctga   9000
gaggagagtg ccagagttgt gtgtacaaca tgatgggaaa aagagaaaag aaacaagggg   9060
aatttggaaa ggccaaggg agccgcgcca tctggtatat gtggctaggg ctagatttc   9120 tagagttcga agcccttgga ttcttgaacg aggatcactg gatggggaga gagaactcag   9180
```

```
gaggtggtgt tgaagggctg ggattacaaa gactcggata tgtcctagaa gagatgagtc    9240
gcataccagg aggaaggatg tatgcagatg acactgctgg ctgggacacc cgcatcagca    9300
ggtttgatct ggagaatgaa gctctaatca ccaaccaaat ggagaaaggg cacagggcct    9360
tggcattggc cataatcaag tacacatacc aaaacaaagt ggtaaaggtc cttagaccag    9420
ctgaaaaagg gaagacagtt atggacatta tttcgagaca agaccaaagg gggagcggac    9480
aagttgtcac ttacgctctt aacacatta ccaacctagt ggtgcaactc attcggagta    9540
tggaggctga ggaagttcta gagatgcaag acttgtggct gctgcggagg tcagagaaag    9600
tgaccaactg gctgcagagc aacgatgggg ataggctcaa acgaatggca gtcagtggag    9660
atgattgcgt tgtgaggcca attgatgata ggtttgcaca tgccctcagg ttcttgaatg    9720
atatggggaa agttaggaag gacacacaag agtggaaacc ctcaactgga tgggacaact    9780
gggaggaagt tccgtttttgc tcccaccact tcaacaagct ccatctcaag gacgggaggt    9840
ccattgtggt tccctgccgc caccaagatg aactgattgg ccgggcccgc gtctctccag    9900
gggcgggatg gagcatccgg gagactgctt gcctagcaaa atcatatgcg caaatgtggc    9960 agctcctttta tttccacaga agggacctcc gactgatggc caatgccatt tgttcatctg    10020
tgccagttga ctgggttcca actgggagaa ctacctggtc aatccatgga aagggagaat    10080
ggatgaccac tgaagacatg cttgtggtgt ggaacagagt gtggattgag gagaacgacc    10140
acatggaaga caagaccca gttacgaaat ggacagacat tccctatttg ggaaaaaggg    10200
aagacttgtg gtgtggatct ctcatagggc acagaccgcg caccacctgg gctgagaaca    10260
ttaaaaacac agtcaacatg gtgcgcagga tcataggtga tgaagaaaag tacatggact    10320
acctatccac ccaagttcgc tacttgggtg aagaagggtc tacacctgga gtgctgtaag    10380
caccaaaaaa aaaaaaaaaa aaaaaaaaaa aaaaaaaaaa aaaaaaaaaa aaaaaaaaaa    10440
aaaaaaaaaa aaaaaaaaaa aaaaaaaaaa aaaaaaaaaa aaaaaaaaaa aaaaaaaaaa    10500
aaaaaaaaaa aaaacagcat attgacgctg ggaaagacca gagactccat gagtttccac    10560
cacgctggcc gccaggcaca gatcgccgaa tagcggcggc cggtgtgggg aaatccatgg    10620
tttct                                                                10625
```

```
<210> SEQ ID NO 6
<211> LENGTH: 10903
<212> TYPE: DNA
<213> ORGANISM: Tick-borne encephalitis virus

<400> SEQUENCE: 6 agatttttctt gcacgtgcat gcgtttgctt cggacagcat tagcagcggt tggtttgaaa    60
gagatattct tttgtttcta ccagtcgtga acgtgttgag aaaaagacag cttaggagaa    120
caagagctgg ggatggtcaa gaaggccatc ctgaaaggta aggggggcgg tccccctcga    180
cgagtgtcga aagagaccgc aacgaagacg cgtcaaccca gagtccaaat gccaaatggg    240
cttgtgttga tgcgcatgat ggggatcttg tggcatgccg tagccggcac cgcgagaaac    300
cccgtattga aggcgttctg gaactcagtc cctctgaaac aggcaacagc agcactgcgg    360
aagatcaaaa ggacggtgag tgccctaatg gttggcttgc aaaaacgtgg gaaaaggagg    420
tcagcgacgg actggatgag ctggttgctg gtcatcactc tgttggggat gacgcttgct    480
gcaacggtga ggaaagaaag ggatggctca actgtgatca gagctgaagg aaaggatgca    540
gcaactcagg tgcgtgtgga gaatggcacc tgtgtgatcc tggctactga catggggtca    600
tggtgtgatg attcactgtc ctatgagtgt gtgaccatag atcaaggaga agagcctgtt    660
```

-continued

```
gacgtggatt gttttgccg gaacgttgat ggagtctatc tggagtacgg acgctgtggg       720
aaacaggaag gctcacggac aaggcgctca gtgctgatcc catcccatgc tcagggagag       780
ctgacgggaa ggggacacaa atggctagaa ggagactcgc tgcgaacaca ccttactaga       840
gttgagggat gggtctggaa gaacaagcta cttgccttgg caatggttac cgttgtgtgg       900
ttgaccctgg agagtgtggt gaccagggtt gccgttcttg ttgtgctcct gtgtttggca       960
ccggtttacg cttcgcgttg cacacacttg gaaaacaggg actttgtgac tggtactcag      1020
gggactacga gggtcacctt ggtgctggaa ctgggtggat gtgttactat aacagctgag      1080
gggaagcctt caatggatgt gtggcttgac gccatttacc aggagaaccc tgctaagaca      1140
cgtgagtact gtttacacgc caagttgtcg gacactaagg ttgcagccag atgcccaaca      1200
atgggaccag ccactttggc tgaagaacac caggtggca cagtgtgtaa gagagatcag       1260
agtgatcgag gctggggcaa ccactgtgga ctgtttggaa agggtagcat tgtggcctgt      1320
gtcaaggcgg cttgtgaggc aaaaaagaaa gccacaggac atgtgtacga cgccaacaaa      1380
atagtgtaca cggtcaaagt cgaaccacac acgggagact atgttgccgc aaacgagaca      1440
catagtggga ggaagacggc atccttcaca atttcttcag agaaaaccat tttgactatg      1500
ggtgagtatg gagatgtgtc tttgttgtgc agggtcgcta gtggcgttga cttggcccag      1560
accgtcatcc ttgagcttga caagacagtg gaacaccttc caacggcttg gcaggtccat      1620
agggactggt tcaatgatct ggctctgcca tggaaacatg agggagcgca aaactggaac      1680
aacgcagaaa gactggttga atttgggggt cctcacgctg tcaagatgga cgtgtacaac      1740
ctcggagacc agactggagt gttactgaag gctctcgctg gggttcctgt ggcacacatt      1800
gagggaacca agtaccacct gaagagtggc cacgtgacct cgcgaagtggg actggaaaaa       1860 ctgaagatga aaggtcttac gtacacaatg tgtgacaaaa caaagttcac atggaagaga      1920
gctccaacag acagtgggca tgatacagtg gtcatggaag tcacattctc tggaacaaag      1980
ccctgtagga tcccagtcag ggcagtggca catggatctc cagatgtgaa cgtggccatg      2040
ctgataacgc caaacccaac aattgaaaac aatggaggtg gcttcataga gatgcagctg      2100
cccccagggg ataacatcat ctatgttggg gaactgagtc atcaatggtt ccaaaaaggg      2160
agcagcatcg gaagggtttt ccaaaagacc aagaaaggca tagaaagact gacagtgata      2220
ggagagcacg cctgggactt cggttctgct ggaggctttc tgagttcaat gggaaggcg       2280 gtacatacgg tccttggtgg cgctttcaac agcatcttcg ggggagtggg gtttctacca      2340
aaacttttat taggagtggc attggcttgg ttgggcctga acatgagaaa ccctacaatg      2400
tccatgagct ttctcttggc tggaggtctg tcttggcca tgacccttgg agtgggggcg       2460
gatgttggtt gcgctgtgga cacggaacga atggagctcc gctgtggcga gggcctggtc      2520
gtgtggagag aggtctcaga atggtatgac aattatgcct actaccggga gacaccgggg      2580
gcccttgcat cagccataaa ggagacattt gaggagggaa gctgtggtgt agtcccccag      2640
aacaggctcg agatggccat gtggagaagc tcggtcacag agctgaattt ggctctggcg      2700
gaaggggagg caaatctcac agtggtggtg gacaagtttg accccactga ctaccgaggt      2760
ggtgtccctg gtttactgaa aaaaggaaag gacataaaag tctcctggaa aagctggggc      2820
cattcaatga tctggagcat tcctgaggcc ccccgtcgct tcatggtggg cacggaagga      2880
caaagtgagt gtcccctaga gagacggaag acaggtgttt tcacggtggc agaattcggg      2940
gttggcctga gaacaaaggt cttcttggat ttcagacagg aaccaacaca tgagtgtgac      3000
```

-continued

```
acaggagtga tgggagctgc agtcaagaac ggcatggcaa tccacacaga tcaaagtctc   3060
tggatgagat caatgaaaaa tgacacaggc acttacatag ttgaactttt ggtcactgac   3120
ctgaggaact gctcatggcc tgctagccac actatcgata atgctgacgt ggtggactca   3180
gagttattcc ttccggcgag cctggcagga cccagatcct ggtacaacag gatacctggc   3240
tattcagaac aggtgaaagg gccatggaag tacacgccta tccgagttat cagagaggag   3300
tgtcccggca cgaccgttac catcaacgcc aagtgtgaca aaagaggagc atctgtgagg   3360
agtaccacag agagtggcaa ggttatccca gaatggtgct gccgagcgtg cacaatgcca   3420
ccagtgacgt tccggactgg aactgattgc tggtatgcca tggaaatacg gccagtccat   3480
gaccaggggg ggcttgttcg ctcaatggtg gttgcggaca acggtgaatt acttagtgag   3540
ggaggagtcc ccggaatagt ggcattgttt gtggtccttg aatacatcat ccgtaggagg   3600
ccctccacgg gaacgacggt tgtgtggggg ggtatcgtcg ttctcgctct gcttgtcacc   3660
gggatggtca ggatagagag cctggtgcgc tatgtggtgg cagtggggat cacattccac   3720
cttgagctgg ggccagagat cgtggccttg atgctactcc aggctgtgtt tgagctgagg   3780
gtgggtttgc tcagcgcatt tgcattgcgc agaagcctca ccgtccgaga gatggtgacc   3840
acctactttc ttttgctggt cctggaattg gggctgccgg gtgcgagcct tgaggagttc   3900
tggaaatggg gtgatgcact ggccatgggg gcgctgatat tcagggcttg cacggcagaa   3960
ggaaagactg gagcggggct tttgctcatg gctctcatga cacagcagga tgtggtgact   4020
gtgcaccatg gactggtgtg cttcctaagt gtagcttcgg catgctcggt ctggaggctg   4080
ctcaagggac acagagagca gaagggattg acctgggttg tcccccctggc tgggttgctt   4140 gggggagagg gctctggaat cagactgctg gcgttttggg agttgtcagc gcacagagga   4200
agacgatctt tcagtgaacc actaactgtg gtaggagtca tgctaacact ggccagcggc   4260
atgatgcgac acacttccca ggaggctctc tgtgcactcg cagtggcctc gtttctcttg   4320
ctgatgctgg tgctggggac aagaaagatg cagctggttg ccgaatggag tggctgcgtt   4380
gaatggtatc cggaactagt gaatgagggt ggagaggtta gcctgcgggt ccggcaggac   4440
gcgatgggta actttcactt gactgagctc gagaaagaag agagaatgat ggctttttgg   4500
ctgattgccg gcttggcagc ttcggccatt cactggtcag gcattcttgg tgtgatggga   4560
ctgtggacgc tcacggaaat gctgaggtca tcccgaaggt ctgacctggt tttctctgga   4620 cagggggtc gagagcgtgg tgacagacct ttcgaggtta aggacggtgt ctacaggatt   4680
tttagccccg gcttgttctg gggtcagaac caggtgggag ttggctacgg ttccaagggt   4740
gtcttgcaca cgatgtggca cgtgacgaga ggagcggcgc tgtctattga tgacgctgtg   4800
gccggtccct actgggctga tgtgagggaa gatgtcgtgt gttacggagg agcctggagc   4860
ctggaggaaa aatggaaagg tgaaacagta caggtccatg ccttcccacc ggggagggcg   4920
catgaggtgc atcagtgcca gcctggggag ttgatccttg acaccggaag aaagcttggg   4980
gcaataccaa ttgatttggt gaaaggaaca tcaggcagcc ccattctcaa cgcccaggga   5040
gtggttgtgg ggctatacgg aaatggccta aaaactaatg agacctacgt cagcagcatt   5100
gctcaaggga aagcggagaa gagtcgcccc aacctccac aggctgttgt gggtacgggc   5160
tggacatcaa agggtcagat cacagtgctg gacatgcacc caggctcggg gaagacccac   5220
agagtcctcc cggagctcat tcgccaatgc attgacaggc gcctgagaac gttggtgttg   5280
gctccaactc gtgtggtact caaagaaatg gagcgtgctt tgaatgggaa acgggtcagg   5340
ttccactcac cagcagtcag tgaccaacag gctggagggg caattgtcga tgtgatgtgt   5400
```

```
cacgcaacct atgtcaacag aaggctactc ccacagggaa gacaaaattg ggaggtggca    5460
atcatggatg aggcccactg gacggacccc cacagcatag ctgccagagg tcatttgtat    5520
actctggcaa aagaaaacaa gtgtgcactg gtcttgatga cagcgacacc tcctggtaag    5580
agtgaaccct ttccggagtc caatggagcc attactagtg aggaaagaca gattcctgat    5640
ggggagtggc gtgacgggtt tgactggatc actgagtatg aagggcgcac cgcctggttt    5700
gtcccttcga ttgcaaaagg tggtgctata gctcgcacct tgagacagaa ggggaaaagt    5760
gtgatttgtt tgaacagcaa aacctttgaa aaggactact ccagagtgag ggatgagaag    5820
cctgactttg tggtgacgac tgatatctcg gagatgggag ctaaccttga cgtgagccgc    5880
gtcatagatg ggaggacaaa catcaagccc gaggaggttg atgggaaagt cgagctcacc    5940
gggaccaggc gagtgaccac ggcttccgct gcccaacggc gcggaagagt tggtcggcaa    6000
gacggacgaa cagatgaata catatactct ggacagtgtg atgatgatga cagtggatta    6060
gtgcaatgga aagaggcgca aatacttctt gacaacataa caaccttgcg ggggcccgtg    6120
gccaccttct atggaccaga acaggacaag atgccggagg tggccggtca ctttcgactc    6180
actgaagaga aaagaaagca cttccgacat cttctcaccc attgtgactt cacaccgtgg    6240
ctggcatggc acgtcgcagc gaatgtatcc agcgtcacgg atcgaagctg gacatgggaa    6300
gggccggagg caaatgccgt ggatgaggcc agtggtgact tggtcacctt taggagcccg    6360
aatggggcgg agagaactct caggccggtg tggaaggacg cacgtatgtt caaagaggga    6420
cgtgacatca aagagttcgt ggcgtacgcg tctgggcgtc gcagcttcgg agatgttctg    6480
acaggaatgt cgggagttcc tgagctcctg cggcacagat gcgtcagtgc cctggatgtc    6540
ttctacacgc ttatgcatga ggaacctggc agcaggcaa tgagaatggc ggagagagat    6600
gccccagagg cctttctgac tatggttgag atgatggtgc tgggtttggc aaccctgggt    6660
gtcatctggt gcttcgtcgt ccggacttca atcagccgca tgatgctggg cacgctggtc    6720
ctgctggcct ccttgctact cttgtgggca ggtggcgtcg gctatgggaa catggctgga    6780
gtggctctca tcttttacac gttgctgacg gtgctgcagc ctgaggcggg aaaacagaga    6840
agcagtgacg acaacaaact ggcatatttc ttgctgacgc tctgcagcct tgctggactg    6900
gttgcagcca atgagatggg ctttctggag aagaccaagg cagacttgtc cacggcgctg    6960
tggagtgaac gggaggaacc ccggccatgg agtgaatgga cgaatgtgga catccagcca    7020
gcgaggtcct gggggaccta tgtgctggtg gtgtctctgt tcacaccttaa catcatccac    7080 caactgcaga ccaaaatcca acaacttgtc aacagtgccg tggcatctgg tgcacaggcc    7140
atgagagacc ttggggggagg tgcccccttc tttggtgtgg cgggacatgt catgaccctc    7200
ggggtggtgt cactgattgg ggctactccc acctcactga tggtgggcgt tggcttggcg    7260
gcactccatc tggccattgt ggtgtctggt ctggaggctg aattaacaca gagagctcat    7320
aaggtctttt tctctgcaat ggtgcgcaac cccatggtgg atgggggatgt catcaaccca    7380 ttcgggggagg gggaggcaaa acctgctcta tatgaaagga aaatgagtct ggtgttggcc    7440
acagtgttgt gcctcatgtc ggtggtcatg aaccgaacgg tggcctccat aacagaggct    7500
tcagcagtgg gactggcagc agcgggacag ctgcttagac cggaggctga cacgttgtgg    7560
acgatgccgg ttgcttgtgg catgagtggt gtggtcaggg gtagcctgtg ggggtttttg    7620
cctcttgggc atagactctg gcttcgagcc tctgggggta ggcgtggtgg ttctgaggga    7680
gacacgcttg gagatctctg gaagcggagg ctgaacaact gcacgaggga ggaattcttt    7740
```

-continued

```
gtgtacaggc gcaccggcat cctggagacg gaacgtgaca aggctagaga gttgctcaga    7800
agaggagaga ccaatgtggg attggctgtc tctcgggggca cggcaaagct tgcctggctt    7860
gaggaacgcg gatatgccac cctcaaggga gaggtggtag atcttggatg tggaaggggc    7920
ggctggtcct attatgcggc atcccgaccg gcagtcatga gtgtcagggc atataccatt    7980
ggtggaaaag ggcacgaggc tccaaagatg gtaacaagcc tgggttggaa cttgattaaa    8040
ttcagatcag gaatggacgt gttcagcatg cagccacacc gggctgacac tgtcatgtgt    8100
gacatcggag agagcagccc agatgccgct gtggagggtg agaggacaag gaaagtgata    8160
ctgctcatgg agcaatggaa aaacaggaac cccacggctg cctgtgtgtt caaggtgctg    8220
gccccatatc gcccagaagt gatagaggca ctgcacagat tccaactgca atggggggg    8280 ggtctggtga ggaccccttt ttcaaggaac tccacccatg agatgtatta ctcaacagcc    8340
gtcactggga acatagtgaa ctccgtcaat gtacagtcga ggaaacttttt ggctcggttt    8400 ggagaccaga gagggccaac caaggtgcct gaactcgacc tgggagttgg aacgaggtgt    8460
gtggtcttag ctgaggacaa ggtgaaagaa caagacgtac aagagaggat cagagcgttg    8520
cgggagcaat acagcgaaac ctggcatatg gacgaggaac acccgtaccg gacatggcag    8580
tactggggca gctaccgcac ggcaccaacc ggctcggcgg cgtcactgat caatggggtt    8640
gtgaaacttc tcagctggcc atggaacgca cgggaagatg tggtgcgcat ggctatgact    8700
gacacaacgg ctttcggaca gcagagagtg ttcaaagata aagttgacac aaaggcacag    8760
gagcctcagc ccggtacaag agtcatcatg agagctgtaa atgattggat tttggaacga    8820
ctggcgcaga aaagcaaacc gcgcatgtgc agcaggaag aattcatagc aaaagtgaaa    8880
tcaaatgcag ccttgggagc ttggtcagat gagcaaaaca gatgggcaag tgcaagagag    8940
gctgtagagg atcctgcatt ctggcgcctc gtggatgaag agagagaaag gcacctcatg    9000
gggagatgtg cgcactgcgt gtacaacatg atgggcaaga gagaaaagaa actgggagag    9060
ttcggagtgg cgaaaggaag tcgggccatt tggtacatgt ggctggggag tcgctttttg    9120
gagttcgagg ctcttggatt cttgaatgaa gaccattggg cctctagaga gtccagtgga    9180
gctggagttg agggaataag cttgaactac ctgggctggc acctcaagaa gttgtcaacc    9240
ctgaatggag gactcttcta tgcagatgac acagctggct gggacacgaa agttaccaat    9300
gcagacttag aggatgaaga acagatccta cggtacatgg agggtgagca caaacaattg    9360
gcaaccacaa taatgcaaaa agcataccat gccaaagtcg tgaaggtcgc gaggccttcc    9420
cgtgatggag gctgcatcat ggatgtcatc acaagaagag accaaagagg ttcgggtcag    9480
gttgtgacct atgcccttaa caccctcacc aacataaagg tgcaattaat ccgaatgatg    9540
gaaggggaag gggtcataga ggcagcggat gcacacaacc cgagactgct tcgagtggag    9600
cgctggctga aagaacacgg agaagagcgt cttggaagaa tgctcgtcag tggtgacgat    9660
tgtgtggtga ggcccttgga tgacagattt ggcaaagcac tttactttct gaatgacatg    9720
gccaagacca ggaaggacat tggggaatgg gagcactcag ccggctttttc aagctgggag    9780 gaggtaccct tttgttcaca ccatttccac gagctagtga tgaaggatgg acgcaccctg    9840
gtggtgccgt gccgagacca agatgaactc gttgggaggg cgcgcatctc accggggtgc    9900
ggctggagtg tccgcgagac ggcctgcctt tcaaaagcct acgggcagat gtggctgctg    9960
agctacttcc accgacgaga cctgaggacg ctcgggcttg ccattaactc agcagtgcct    10020
gccgattggg ttcctaccgg ccgcacgacg tggagcattc atgccagtgg ggcctggatg    10080
accacagaag acatgctgga cgtttggaac cgggtgtgga ttctggacaa ccctttcatg    10140
```

-continued

```
cagaacaagg aaagggtcat ggagtggagg gatgttccgt acctccctaa agctcaggac   10200
atgttatgtt cctcccttgt tgggaggaga gaaagagcag aatgggccaa gaacatctgg   10260
ggagcggtgg aaaaggtgag gaagatgata ggtcctgaaa agttcaagga ctatctctcc   10320
tgtatggacc gccatgacct gcactgggag ctcagactgg agagctcaat aatctaaacc   10380
cagaaaaaaa aaaaaaaaaa aaaaaaaaaa aaaaaaaaaa aaaaaaaaaa aaaaaaaaaa   10440
aaaaaaaaaa aaaaaaaaaa aaaaaaaaaa aaaaaaaaaa aaaaaaaaaa aaaaaaaaaa   10500
aaaaaaaaaa aaaaaaaaaa aaaaaaaaaa aaaccccctg accagcaaag ggggcagacc   10560
ggtcaggggt gaggaatgcc cccagagtgc attacggcag cacgccagtg agagtggcga   10620
cgggaaaatg gtcgatcccg acgtagggca ctctgaaaaa ttttgtgaga ccccctgcat   10680
catgataagg ccgaacatgg tgcatgaaag gggaggcccc cggaagcacg cttccgggag   10740
gagggaagag agaaattggc agctctcttc aggatttttc ctcctcctat acaaaattcc   10800
ccctcggtag aggggggggcg gttcttgttc tccctgagcc accatcaccc agacacaggt   10860
agtctgacaa ggaggtgatg tgtgactcgg aaaaacaccc gct                      10903
```